US012642960B2

(12) United States Patent (10) Patent No.: US 12,642,960 B2
Miller (45) Date of Patent: Jun. 2, 2026

(54) TRANSESOPHAGEAL VAGUS NERVE STIMULATION

(71) Applicant: Medtronic, Inc., Minneapolis, MN (US)

(72) Inventor: David J. Miller, Austin, TX (US)

(73) Assignee: Medtronic, Inc., Minneapolis, MN (US)

( * ) Notice: Subject to any disclaimer, the term of this patent is extended or adjusted under 35 U.S.C. 154(b) by 340 days.

(21) Appl. No.: 17/812,356

(22) Filed: Jul. 13, 2022

(65) Prior Publication Data

US 2023/0026849 A1     Jan. 26, 2023

Related U.S. Application Data

(60) Provisional application No. 63/364,075, filed on May 3, 2022, provisional application No. 63/224,753, filed on Jul. 22, 2021.

(51) Int. Cl.
*A61N 1/05* (2006.01)
*A61N 1/02* (2006.01)
*A61N 1/36* (2006.01)

(52) U.S. Cl.
CPC .......... *A61N 1/0509* (2013.01); *A61N 1/025* (2013.01); *A61N 1/36053* (2013.01); *A61N 1/36135* (2013.01); *A61N 1/3615* (2013.01)

(58) Field of Classification Search
CPC .. A61N 1/0509; A61N 1/025; A61N 1/36053; A61N 1/36135; A61N 1/3615; A61N 1/0517
See application file for complete search history.

(56) References Cited

U.S. PATENT DOCUMENTS 6,599,237 B1 * 7/2003 Singh ................... A61B 1/0008
600/114
6,689,056 B1     2/2004 Kilcoyne et al.
(Continued)

FOREIGN PATENT DOCUMENTS

EP         2213330 A2     8/2020
EP         3998029 B1 *  7/2024     ......... A61B 18/1206
(Continued)

OTHER PUBLICATIONS

U.S. Appl. No. 63/224,753, filed Jul. 22, 2021, naming inventors David J. Miller.
(Continued)

*Primary Examiner* — Michael W Kahelin
*Assistant Examiner* — Attiya Sayyada Hussaini
(74) *Attorney, Agent, or Firm* — Shumaker & Sieffert, P.A.

(57)     ABSTRACT

Example devices and techniques are disclosed for delivering neurostimulation therapy transesophageally. An example device includes stimulation circuitry configured to generate a transesophageal stimulation signal. The example device includes memory configured to store stimulation parameters that at least partially define the transesophageal stimulation signal and processing circuitry communicatively coupled to the memory, and the stimulation circuitry. The processing circuitry is configured to determine a maximum transesophageal stimulation amplitude value. The processing circuitry is configured to control the stimulation circuitry to generate the transesophageal stimulation signal based at least in part on at least one of the stimulation parameters or the maximum transesophageal stimulation amplitude such that an amplitude of the transesophageal stimulation signal does not exceed the maximum transesophageal stimulation amplitude.

16 Claims, 21 Drawing Sheets

(56) References Cited

U.S. PATENT DOCUMENTS

| | | | |
|---|---|---|---|
| 6,754,536 B2 | 6/2004 | Swoyer et al. | |
| 7,580,751 B2 | 8/2009 | Starkebaum | |
| 7,869,884 B2 | 1/2011 | Scott et al. | |
| 7,904,175 B2 | 3/2011 | Scott et al. | |
| 7,962,214 B2 * | 6/2011 | Byerman | A61N 1/36114 607/116 |
| 7,991,474 B2 * | 8/2011 | Aldrich | A61B 8/445 607/40 |
| 8,216,158 B2 * | 7/2012 | Johnson | A61B 17/3468 600/593 |
| 8,301,265 B2 | 10/2012 | Starkebaum | |
| 8,538,533 B2 * | 9/2013 | Knudson | A61N 1/36053 607/40 |
| 8,738,126 B2 * | 5/2014 | Craig | A61N 1/36139 607/45 |
| 9,162,062 B2 | 10/2015 | Knudson et al. | |
| 9,504,832 B2 | 11/2016 | Libbus et al. | |
| 10,335,547 B2 | 7/2019 | Ward et al. | |
| 10,398,900 B2 * | 9/2019 | Lee | A61N 1/36071 |
| 10,575,893 B2 | 3/2020 | Mayse | |
| 2008/0183254 A1 * | 7/2008 | Bly | A61N 1/0558 607/116 |
| 2012/0271382 A1 * | 10/2012 | Arcot-Krishnamurthy | A61N 1/36185 607/62 |
| 2013/0245722 A1 * | 9/2013 | Ternes | A61N 1/36114 607/62 |
| 2013/0289646 A1 * | 10/2013 | Libbus | A61N 1/0551 607/30 |
| 2014/0135886 A1 | 5/2014 | Cook et al. | |
| 2016/0250097 A9 | 9/2016 | Tracey et al. | |
| 2017/0348521 A1 | 12/2017 | Cook et al. | |
| 2018/0154156 A1 * | 6/2018 | Clark | A61N 1/36175 |
| 2018/0311497 A1 * | 11/2018 | Viswanathan | A61N 1/37258 |
| 2019/0099602 A1 * | 4/2019 | Esteller | A61N 1/37241 |
| 2019/0117977 A1 | 4/2019 | Puleo et al. | |
| 2019/0192855 A1 | 6/2019 | Bharmi et al. | |
| 2019/0275328 A1 | 9/2019 | Zitnik et al. | |
| 2020/0330760 A1 * | 10/2020 | Levine | A61B 5/4035 |
| 2022/0079502 A1 * | 3/2022 | Simon | G16H 20/30 |
| 2022/0079666 A1 * | 3/2022 | Ku | A61M 25/0138 |

FOREIGN PATENT DOCUMENTS

| | | | | |
|---|---|---|---|---|
| WO | WO-2018080753 A1 * | 5/2018 | | A61B 5/4836 |
| WO | 2021026606 A1 | 2/2020 | | |

OTHER PUBLICATIONS

U.S. Appl. No. 63/364,075, filed May 3, 2022, naming inventors David J. Miller.

* cited by examiner

470

MECHANICAL STIMULATION DEVICE
474

SENSOR
476

PROCESSING CIRCUITRY
473

TELEMETRY CIRCUITRY
478

MEMORY
480

STIMULATION PROGRAMS
482

PATIENT DATA
485

POWER SOURCE
486

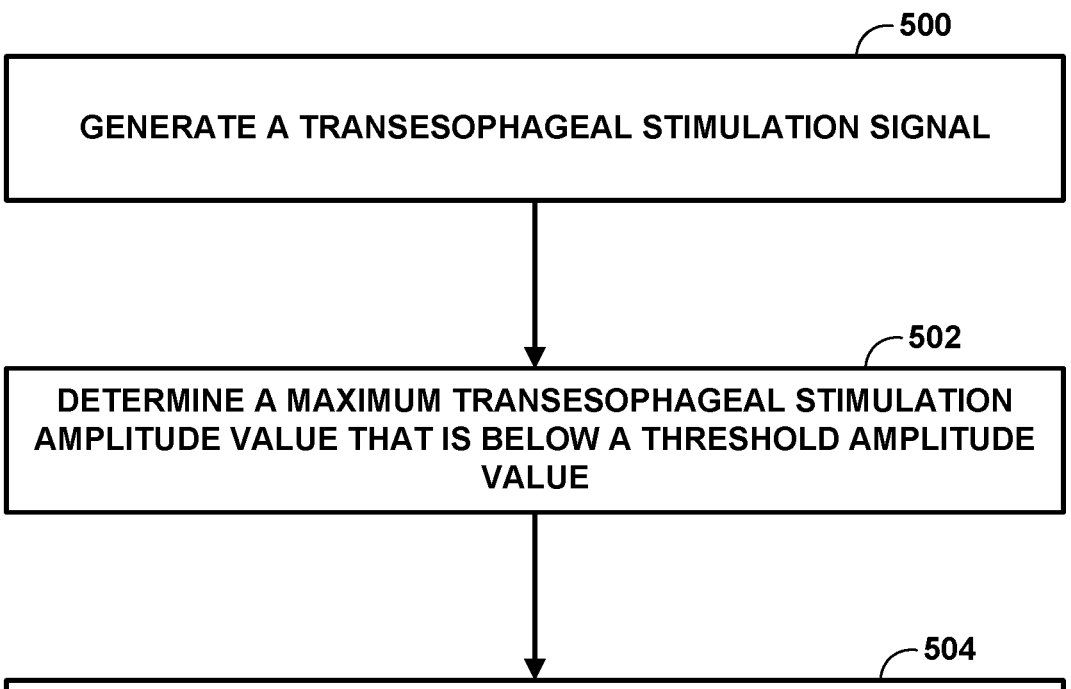

┌─ 500

GENERATE A TRANSESOPHAGEAL STIMULATION SIGNAL

┌─ 502

DETERMINE A MAXIMUM TRANSESOPHAGEAL STIMULATION AMPLITUDE VALUE THAT IS BELOW A THRESHOLD AMPLITUDE VALUE

┌─ 504

CONTROL THE STIMULATION CIRCUITRY TO GENERATE THE TRANSESOPHAGEAL STIMULATION SIGNAL BASED AT LEAST IN PART ON AT LEAST ONE OF THE STIMULATION PARAMETERS OR THE MAXIMUM TRANSESOPHAGEAL STIMULATION AMPLITUDE SUCH THAT AN AMPLITUDE OF THE TRANSESOPHAGEAL STIMULATION SIGNAL DOES NOT EXCEED THE MAXIMUM TRANSESOPHAGEAL STIMULATION AMPLITUDE

FIG. 22

TRANSESOPHAGEAL VAGUS NERVE STIMULATION

This application claims priority to U.S. Provisional Patent Application No. 63/224,753, filed Jul. 22, 2021, and U.S. Provisional Patent Application No. 63/364,075, filed May 3, 2022, the entire content of both of which is incorporated by reference.

TECHNICAL FIELD

The disclosure relates to devices and techniques for stimulating a vagus nerve of a patient transesophageally.

BACKGROUND

Neuromodulation by electrical stimulation of the cervical, thoracic, and abdominal branches of the vagus nerve has been shown to be useful for a wide range of purposes.

SUMMARY

In general, the disclosure is directed to devices, systems, and techniques for transesophageally stimulating a vagus nerve of a patient, for example, stimulating the vagus nerve of the patient from one or more electrodes disposed within the esophagus of the patient. Because the vagus nerve is located in an anatomically challenging location to access, a vagus nerve may be challenging to stimulate without an invasive surgical procedure, which may be undesirable for situations including an acute illness, a short duration of stimulation, or when reduced time to stimulation is important to patient treatment.

In one example, the disclosure is directed to a system comprising: stimulation circuitry configured to generate a transesophageal stimulation signal; memory configured to store stimulation parameters that at least partially define the transesophageal stimulation signal; and processing circuitry communicatively coupled to the memory, and the stimulation circuitry, the processing circuitry being configured to: determine a maximum transesophageal stimulation amplitude value that is below a threshold amplitude value that defines a transesophageal stimulation amplitude that elicits muscular activity in response to delivery of the stimulation signal via a combination of electrodes; and control the stimulation circuitry to generate the transesophageal stimulation signal based at least in part on at least one of the stimulation parameters or the maximum transesophageal stimulation amplitude such that an amplitude of the transesophageal stimulation signal does not exceed the maximum transesophageal stimulation amplitude.

In another example, this disclosure is directed to a method including generating, by stimulation circuitry, a transesophageal stimulation signal; determining, by processing circuitry, a maximum stimulation amplitude value that is below a threshold amplitude value that defines a transesophageal stimulation amplitude that elicits muscular activity in response to delivery of the stimulation signal via a combination of electrodes; and controlling, by the processing circuitry, the stimulation circuitry to generate the transesophageal stimulation signal based at least in part on at least one stimulation parameter or the maximum transesophageal stimulation amplitude prior to muscular activity such that an amplitude of the transesophageal stimulation signal does not exceed the maximum transesophageal stimulation amplitude.

In another example, this disclosure is directed to a non-transitory storage medium computer-readable storage medium includes instructions that, when executed, cause processing circuitry of a device to: determine a maximum transesophageal stimulation amplitude value that is below a threshold amplitude value that defines a transesophageal stimulation amplitude that elicits muscular activity in response to delivery of a stimulation signal via a combination of electrodes, the transesophageal stimulation signal being at least partially defined by stimulation parameters; and control stimulation circuitry to generate the transesophageal stimulation signal based at least in part on at least one of the stimulation parameters or the maximum transesophageal stimulation amplitude such that an amplitude of the transesophageal stimulation signal does not exceed the maximum transesophageal stimulation amplitude.

The details of one or more examples are set forth in the accompanying drawings and the description below. Other features, objects, and advantages of the disclosure will be apparent from the description and drawings, and from the claims.

The above summary is not intended to describe each illustrated example or every implementation of the present disclosure.

BRIEF DESCRIPTION OF DRAWINGS

FIG. 22 is a flow diagram illustrating additional example techniques of the present disclosure.

DETAILED DESCRIPTION

Figure 1:
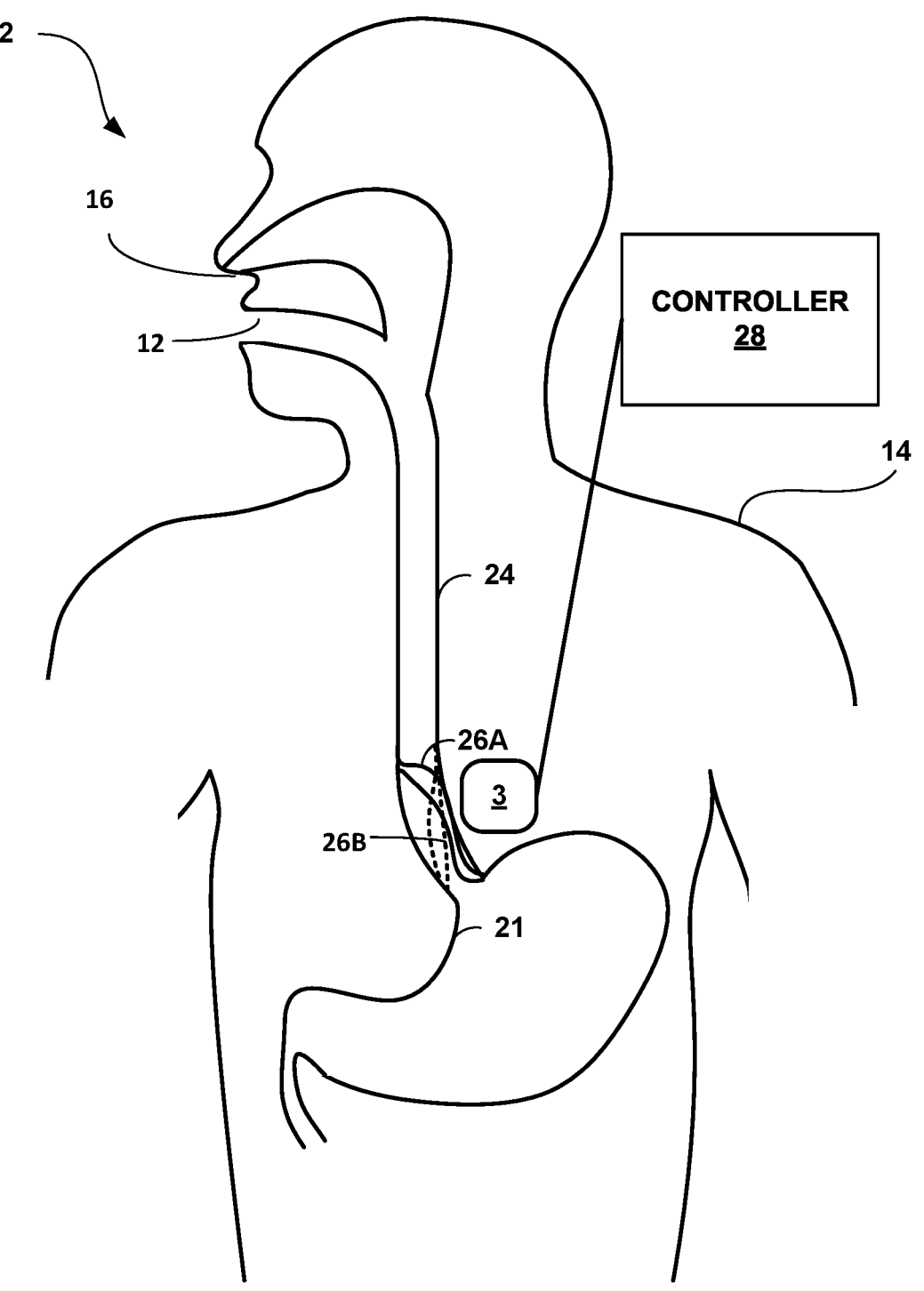
FIG. 1 is a conceptual diagram illustrating an example neurostimulation system according to the techniques of this disclosure.

The present disclosure is directed to devices, systems, and techniques for transesophageal neurostimulation of a vagus nerve of a patient. The anatomical location of the vagus nerve makes the vagus nerve difficult to stimulate without an invasive surgical procedure. In an acute situation, such as during other surgery or an abrupt illness, such as sepsis, stroke, myocardial infarction, traumatic brain injury, or when the required duration of stimulation is limited to short amount of time, it may be undesirable to undertake an invasive surgical procedure to implant a stimulation device. In other situations, transesophageal neurostimulation of the vagus nerve can be used prophylactically perioperatively to prevent acute kidney injury or postoperative ileus. Recent discoveries relating to vagus nerve stimulation have uncovered the nervous system involvement and control of the body's inflammatory response. The nervous system senses inflammation, pathogens, and tissue damage, as well as, modulates the response. One pathway of the nervous system is referred to as the cholinergic anti-inflammatory pathway (CAP). Animal and humans studies have shown the stimulating certain nerves, usually branches of the vagus nerve, can dampen the inflammatory response and associated cytokines. Stimulation has been investigated in the cervical vagus, the abdominal vagus, the auricular branch of the vagus in the ear, the sacral nerve, the tibial nerve, and others. Recent studies have shown that by varying the stimulation, inflammatory cytokines can be modulated up or down.

Implantable cervical vagus stimulators are commercially available for the treatment of epilepsy, but involve complex and invasive surgery to implant the stimulating electrode on the nerve. Other technologies attempt to stimulate the vagus transcutaneously with an external device, but those have shown limited success due to the distance from the skin surface to the vagus nerve.

A device configured to stimulate the vagus nerve without an invasive surgical procedure may be used to trigger the cholinergic anti-inflammatory pathway (CAP). CAP has been shown to reduce excessive inflammation and would be useful for treating a variety of illness including, but not limited to: surgical or non-surgical acute kidney injury; postoperative ileus; postoperative cognitive decline or postoperative delirium; asthma; sepsis; bleeding control; myocardial infarction reduction; and dysmotility and obesity. Treating any of these diseases may improve patient outcomes by shortening length of hospital stays and reducing medical costs.

Many conditions can be caused by damage to tissue from an overreaction of the inflammatory process. One such condition is ischemia-reperfusion injury (IRI). In IRI, tissue experiences ischemia due to reduced or stopped blood supply, followed by reperfusion due to medical intervention or the body's healing response. When tissue experiences an IRI, the immune system reacts to the damaged or dead cells with an intense inflammatory response causing infarcted tissue and loss of long-term function. Reducing the inflammatory response during the ischemia or reperfusion can reduce the resulting infarct volume and improve function. Examples of common conditions that may lead to IRI include myocardial infarction (the abrupt blockage of coronary arteries leading to zones of infarcted heart tissue), acute ischemic stroke and transient ischemic attack (the blockage of blood vessels in the brain or leading to the brain), or acute kidney injury (AKI) (abrupt loss of renal function due to an injury). AKI typically occurs in surgical patients and septic patients. AKI is distinct from chronic kidney disease, which is the gradual loss of kidney function. AKI can be caused by many things, but a common cause is reduced renal blood flow and/or renal blood oxygen extraction.

There are other common acute medical problems that involve an inappropriate over-reaction by the immune system. Some examples of such conditions include severe asthma attacks with may involve excessive mucus secretion and airway narrowing, sepsis (some forms of sepsis may be driven by the immune system over-reacting, which may be referred to as a "cytokine storm"), or post-operative ileus. For example, after abdominal surgeries, it is common for patients to have ileus, or the inability of the intestine (bowel) to contract normally and move waste out of the body. Ileus may be caused by an inflammatory response in the bowel due to surgical manipulation.

Other conditions manifest as an imbalance in the sympathetic/parasympathetic balance. If the imbalance is decreased parasympathetic tone, the imbalance can cause temporary cardiac arrhythmias.

All of the above conditions can be treated (e.g., reduced symptoms or improved clinical outcomes) by stimulating the vagus nerve. Vagus nerve stimulation may reduce inflammatory damage from IRI, return inflammation to a normal level and prevent the hyperinflammatory response, and/or restore a healthy, normal parasympathetic/sympathetic balance.

The inflammatory response of a patient to an acute health problem may be a major risk factor to complications during the acute health problem, such as surgery or an acute illness. It may not be desirable to engage in an invasive surgical procedure to implant a stimulation device during the time the patient is experiencing the acute health problem, as that may be a further risk factor to complications during the acute health problem. Therefore, there may be a need for devices, systems, and techniques for stimulating the cervical, thoracic, or abdominal vagus branches that is relatively easy and quick to use, such as a transesophageal stimulation system. Such devices or techniques may be used for short-term stimulation, such as during an acute health problem, such as surgery or during an abrupt illness, such as sepsis. Additionally, overstimulation of the vagus nerve may lower a heart rate of a patient, which may lead to arrhythmias. or lower a respiration rate of the patient. Therefore, it may be desirable to include closed-loop feedback techniques in any transesophageal neurostimulation system or device. This disclosure describes examples of such devices, systems, and techniques.

FIG. 1 is a conceptual diagram illustrating an example neurostimulation system 2. Neurostimulation system 2 includes controller 28 and transcutaneous neurostimulation device 3. Transcutaneous neurostimulation device 3 may include a plurality of electrodes (not shown) and be configured to provide neurostimulation to a vagus nerve of patient 14 under the control of controller 28 (described in more detail with respect to FIGS. 2 and 12). In some examples, transcutaneous neurostimulation device 3 may include a patch for applying to an outer surface of skin of patient 14, such as on near the stomach of patient 14. In some examples, the patch may include an adhesive for securing the patch to the outer surface of the skin.

Patient 14 is depicted having stomach 21 and esophagus 24. Mouth 12 and nasal cavity 16 are connected to esophagus 24 and may provide access to esophagus 24 for a transesophageal neurostimulation system (not shown). Also depicted are representations of branches of the vagus nerve, namely anterior branch 26A of the vagus nerve or posterior branch 26B of the vagus nerve. Transesophageal neurostimulation devices may deliver neurostimulation to one or more of anterior branch 26A of the vagus nerve or posterior branch 26B of the vagus nerve via one or more electrodes disposed within esophagus 24 of patient 14.

Figure 2:
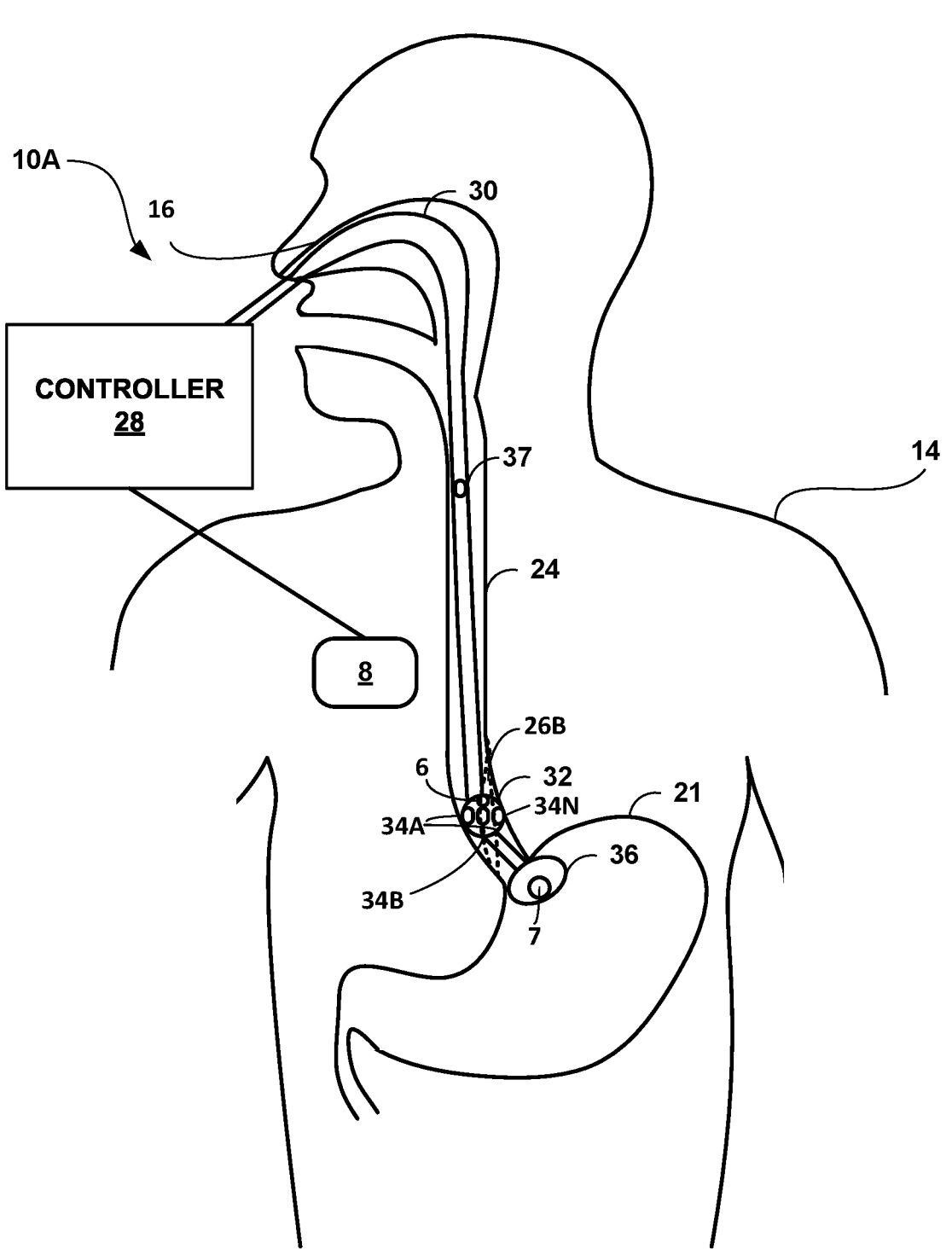
FIG. 2 is a conceptual diagram illustrating an example transesophageal neurostimulation system according to the techniques of this disclosure.

FIG. 2 is a conceptual diagram illustrating an example transesophageal neurostimulation system 10A according to the techniques of this disclosure. A distal end of transesophageal neurostimulation system 10A may be introduced into esophagus 24 through either nasal cavity 16 (as shown) or mouth 12 and stimulate the vagus nerve through the wall of esophagus 24. One possible location of the delivery of stimulus would be at or near where 24 esophagus passes through a diaphragm, or caudal from the diaphragm (not shown), of patient 14. At this location, the vagus nerve is primarily organized into anterior branch 26A and posterior branch 26B (FIG. 1) that are both attached to the outer layer of esophagus 24. Esophagus 24 may be thin, around only about 1-3 mm thick, and even thinner if esophagus 24 is distended. Thus, transesophageal neurostimulation system 10A may deliver electrical stimulation through the wall of esophagus 24 and to a portion of the vagus nerve. In some examples, transesophageal neurostimulation system 10A may be used to stimulate one or more of branches of the vagus nerve, roots of the vagus nerve, ganglia of the vagus nerve, or plexus of the vagus nerve. In some examples, transesophageal neurostimulation system 10A may be biased, such as being bent or weighted, in such a manner as to position electrodes of transesophageal neurostimulation system 10A at locations more likely to be near the vagus nerve, such as anterior branch 26A and/or posterior branch 26B. In some examples, transesophageal neurostimulation system 10A may include a steerable or deflectable device configured to indent, appose, or penetrate electrodes of transesophageal neurostimulation system 10A into an inner wall of esophagus 24. For example, the steerable or deflectable device may be flexible for insertion into patient 14, but include a bias to a shaft of the device (such as elongated member 30) and/or a direction of deflection that facilitates the positioning of the electrodes at locations more likely to be near the vagus nerve.

Esophagus 24 is located between the spinal column and the heart (neither shown in FIG. 2). The anterior of esophagus 24 is adjacent to the heart. In some examples, to reduce or avoid inadvertent heart stimulation, transesophageal neurostimulation system 10A may be configured to direct stimulation towards posterior branch 26B or posterior trunk of the vagus nerve. For example, transesophageal neurostimulation system 10A may include sensor 6 which may include an accelerometer which may be used to determine the posterior direction. For example, transesophageal neurostimulation system 10A can detect the movements due to each heartbeat and determine the posterior direction being away from the detected acceleration. In addition, or alternatively, sensing electrodes of electrodes 34 may be used to sense an EKG of patient 14 and controller 28 may determine the posterior direction based on the sensed EKG signal. For example, EKG signals sensed from electrodes facing the posterior of patient 14 may sense a lower amplitude EKG then electrodes facing the anterior of patient 14. In some examples, elongated member 30 and/or expandable member 32 may be shaped in such a manner as to automatically orient the stimulation electrode(s) posteriorly.

Transesophageal neurostimulation system 10A includes controller 28, elongated member 30, and expandable member 32. Controller 28 may be configured to control neurostimulation being delivered to the vagus nerve (not shown in FIG. 2) of patient 14. For example, controller 28 may include processing circuitry, telemetry circuitry, and memory. The telemetry circuitry may be configured for wireless or wired communication. In some examples, controller 28 may also include stimulation circuitry configured to generate a stimulation signal. In other examples, the stimulation circuitry may be located in a portion of transesophageal neurostimulation system 10A that is internal to patient 14.

Controller 28 may be an example of a computing device. In some examples, external controller 28 may include a clinician programmer or patient programmer. In some examples, controller 28 may be a device for inputting stimulation programs or stimulation parameters into transesophageal neurostimulation system 10A. In some examples, controller 28 may be a wearable communication device, with a therapy request input integrated into a key fob or a wristwatch, handheld computing device, smart phone, computer workstation, or networked computing device. Controller 28 may include a user interface that is configured to receive input from a user (e.g., patient 14, a caretaker, or a clinician). In some examples, the user interface includes, for example, a keypad and a display, which may for example, be a liquid crystal display (LCD) or light emitting diode (LED) display. In some examples, the user interface may include a turnable knob or a representation of a turnable knob. The keypad may take the form of an alphanumeric keypad or a reduced set of keys associated with particular functions. Controller 28 may additionally or alternatively include a peripheral pointing device, such as a mouse, via which a user may interact with the user interface. In some examples, a display of controller 28 may include a touch screen display, and a user may interact with controller 28 via the display.

A user, such as a clinician, a patient, or a caregiver, may also interact with controller 28 to communicate with transesophageal neurostimulation system 10A. Such a user may interact with controller 28 to retrieve physiological or diagnostic information from one or more of a sensor, processing circuitry, or memory that may be located on or in a portion of transesophageal neurostimulation system 10A that is intended to be within patient 14 during stimulation. The user may also interact with controller 28 to program transesophageal neurostimulation system 10A, e.g., select values for the stimulation parameter with which transesophageal neurostimulation system 10A generates and delivers stimulation and/or the other operational parameters of transesophageal neurostimulation system 10A, such as one or more stimulation parameters (e.g., pulse amplitude, pulse width, pulse frequency, pulse burst duration, electrode combination, etc.), user requested periods for stimulation or periods to prevent stimulation, or any other such user customization of therapy.

For example, the user may use controller 28 to retrieve information from transesophageal neurostimulation system 10A relating to a heartrate of patient 14, a heart rate variability over time, respiration rate, vagus nerve sensed activity, temperature, or the like. As another example, the user may use controller 28 to retrieve information from transesophageal neurostimulation system 10A relating to the performance or integrity of transesophageal neurostimulation system 10A. In some examples, this information may be presented to the user as an alert if a system condition that may affect the efficacy of therapy is detected.

Patient 14 or a clinician may, for example, use a keypad or touch screen of controller 28 to request transesophageal neurostimulation system 10A to deliver or terminate the electrical stimulation. For example, patient 14 may use controller 28 to provide a therapy request to control the delivery of the electrical stimulation "on demand," e.g., when patient 14 deems the second stimulation therapy desirable. This request may be a therapy trigger event used to terminate electrical stimulation.

Controller 28 may provide a notification to patient 14 or a clinician when the electrical stimulation is being delivered or notify patient 14 of the prospective termination of the electrical stimulation. In such examples, controller 28 may display a visible message, emit an audible alert signal or provide a somatosensory alert (e.g., by causing a housing of controller 28 to vibrate). In other examples, the notification may indicate when therapy is available (e.g., a countdown in minutes, or indication that therapy is ready).

As patients in a hospital environment may need magnetic resonance imagery (MRI) to be taken by an MRI device or other procedures by other devices, it may be desirable for controller 28 to be detachable or detached from elongated member 30 to facilitate the transportation of patient 14 to the device, insertion of patient 14 into the device, and operation of the device, if necessary. As such controller 28 may be detachable or separate from elongated member 30. Alternatively, the transesophageal neurostimulation system, such as transesophageal neurostimulation system 10A, may be MRI compatible such that the transesophageal neurostimulation system does not substantially interfere with the images taken by the MRI device.

In the example where controller 28 includes stimulation circuitry, elongated member 30 may include conductors configured to conduct the stimulation signal from the stimulation circuitry of controller 28 to electrodes 34A, 34B, and 34N (hereinafter referred to collectively as electrodes 34 which can include two or more electrodes). In some examples, each of electrodes 34 may not form a closed loop so as reduce the risk of entanglement with another nasogastric tube, should another nasogastric tube be introduced or be already introduced into esophagus 24. In the example where controller 28 does not include stimulation circuitry, elongated member 30 may include conductors configured to conduct communication signals from telemetry circuitry of controller 28 to telemetry circuitry located in a portion of transesophageal neurostimulation system 10A designed to be internal to patient 14 when stimulation is delivered. Elongated member 30 may also define a lumen configured to permit the removal or introduction of substances from patient 14. For example, the lumen may permit the introduction of food, drink, medication, or the like from external of the patient into esophagus 24 or stomach 21.

While system 10A is primarily discussed as being configured to deliver electrical stimulation, in some examples, system 10A may be configured to deliver other types of stimulation to the vagus nerve. For example, system 10A may be configured to deliver mechanical stimulation at relatively low frequency, such as through vibration, or at relatively higher frequencies, such as ultrasound. In such a case, rather than, or in addition to, having electrodes 34, expandable member 32 and/or elongated member 30 may include a vibration causing device, such as a haptic device, or an ultrasound device, which may be configured to deliver mechanical stimulation to the vagus nerve. In some examples, system 10A may be configured to deliver thermal stimulation to the vagus nerve. In such a case, rather than, or in addition to, having electrodes 34, expandable member 32 and/or elongated member 30 may include a thermal device configured to deliver heating or cooling toward the vagus nerve to stimulate the vagus nerve. In some examples, system 10A may be configured to deliver chemical or pharmaceutical stimulation to the vagus nerve. In such a case, rather than, or in addition to, having electrodes 34, expandable member 32 and/or elongated member 30 may include a device which may be configured to release a bolus of one or more chemicals of pharmaceuticals under the control of controller 28.

Expandable member 32 may be configured to expand from a non-expanded or collapsed state to a size approximately equal to the circumference of an internal wall of esophagus 24 thereby causing electrodes 34 to make physical contact with the internal wall of esophagus 24. In some examples, expandable member 32 may be configured to expand to distend the internal wall of esophagus 24. In some examples, expandable member 32 may include a balloon or other expandable structure, such as a mechanically expandable structure that includes struts and/or linkages that enables expansion (e.g., similar to a stent or cage). In some examples, expandable member 32 may include one or more of a spiral, a helix, a partial spiral, a plurality of spirals, a plurality of helixes, or a plurality of partial spirals.

In some examples, an additional expandable member 36 may be included in transesophageal neurostimulation system 10A. Expandable member 36 may be configured to expand in stomach 21 of patient 14, under the control of a clinician, in such a manner as to position electrodes 34 in a position to stimulate a target location in patient 14, such as one or more branches of the vagus nerve. For example, a clinician may desire to position electrodes 34 relative to a lower esophageal sphincter separating esophagus 24 from stomach 21. For example, esophagus 24 may be relatively thick and muscular at the lower esophageal sphincter, so it may be desirable to stimulate the vagus nerve cranially of the lower esophageal sphincter. In some examples, transesophageal neurostimulation system 10A may be configured such that electrodes 34 are located in the range of about 2 cm to about 12 cm from an upper shoulder of expandable member 36 or from the z-line. The z-line is a term for a faint zig-zag impression at the gastro-esophageal junction. This impression demarcates the transition between the stratified squamous epithelium in the esophagus and the intestinal epithelium of the gastric cardia (e.g., the squamo-columnar junction). In some examples, expandable member 36 may include a balloon or other expandable structure, such as a mechanically expandable structure that includes struts and/or linkages that enables expansion (e.g., similar to a stent or cage).

In some examples, system 10A may include sensor 7 which may be positioned on expandable member 36, or in the example where system 10A does not include an expandable member 36, at or near a distal end of elongated member 30 (for example, distal to expandable member 32). Sensor 7 may be configured to generate a signal indicative the entry of sensor 7 into stomach 21 or entry into the lower esophageal sphincter of patient 14. In this manner, electrodes 34 (or other stimulation device) may be placed at an appropriate location for stimulation within esophagus 24 of patient 14 without a need to use fluoroscopy. For example, sensor 7 may include a pressure sensor. A pressure of esophagus 24, stomach 21, and the lower esophageal sphincter may be characteristically different. In this manner, controller 28 may determine when sensor 7 enters into stomach 21 or into the lower esophageal sphincter of patient 14. Sensor 7 may include a pH sensor. Sensor 7 may generate a signal indicative of a pH in patient 14. For example, the pH of esophagus 24 may typically be around 7.0, while a pH of stomach 21 may typically be in the range of 1.5 to 3.5. In this manner controller 28 may determine when sensor 7, and the distal portion of elongated member 30, enters into stomach 21. In some examples, based on the controller 28 determining that sensor 7 has entered into stomach 21, controller 28 may initiate stimulation and/or expansion of expandable member(s) 32 and/or 36.

Elongated member 30 and expandable members 32 and/or 36 may be sized in the range of from 8 to 18 French when expandable members 32 and/or 36 are in a non-expanded or collapsed state to enable relatively easy introduction of elongated member 30 and expandable members 32 and/or 36 within nasal cavity 16 or mouth 12 of patient 14. In some examples, in order to reduce sliding friction between system 10A and patient 14 during insertion of a portion of system 10A into patient 14, elongated member 30, expandable member 32, and/or expandable member 36 may be lubricated. In some examples, the lubrication may be contained within packaging that encloses at least a portion of system 10A, may be pre-lubricated, or, in some examples, system 10A may be configured to self-lubricate. For example, controller 28 may include a lubrication pump that pump lubricant onto an exterior surface of elongated member 30, expandable member 32, and/or expandable member 36. In some examples, elongated member 30, expandable member 32, and/or expandable member 36 may define a lubricating lumen which may carry lubricant from the lubrication pump to an exterior surface of elongated member 30, expandable member 32, and/or expandable member 36 via lubrication openings. In other examples, a lubrication lumen of elongated member 30, expandable member 32, and/or expandable member 36 may be prefilled with lubricant and the pressure exerted upon elongated member 30, expandable member 32, and/or expandable member 36 by esophagus 24 during insertion of elongated member 30 into esophagus 24 may cause the prefilled lubricant to be discharged via the lubrication openings to the exterior surface of elongated member 30. In other examples, a coating may be applied to elongated member 30, expandable member 32, and/or expandable member 36 which may become lubricious when in contact with saliva or mucus of patient 14.

In some examples, in addition to, or alternatively, in order to reduce patient discomfort caused by system 10A, elongated member 30, expandable member 32, and/or expandable member 36 may be pre-coated with a local anesthetic such as lidocaine. In some examples, the local anesthetic may be included in the packaging that encloses at least a portion of system 10A. In some examples, the local anesthetic may be combined with a lubricant.

Transesophageal neurostimulation system 10A may deliver electrical stimulation to patient 14 by generating and delivering a programmable electrical stimulation signal (e.g., in the form of electrical pulses or an electrical waveform) to a target a therapy site near electrodes 34 disposed, in some examples, on an outer surface of expandable member 32. The distal end of transesophageal neurostimulation system 10A may be inserted into patient 14 in such a manner as to locate electrodes 34 near the vagus nerve of patient 14. Elongated member 30, expandable member 32, and expandable member 36 may be constructed of biocompatible materials.

Electrodes 34 may be configured to be circumferentially separated from each other on an outer surface of expandable member 32. In some examples, transesophageal neurostimulation system 10A may be configured to deliver a stimulation signal to the vagus nerve of patient 14 via electrodes 34 in a cycled manner. For example, the delivery of the stimulation signal may move over time between different electrode combinations of electrodes 34, such as delivering stimulation via electrode 34A and electrode 34B, then delivering stimulation via electrode 34B and another electrode, and so on. In this manner, a clinician may not need to circumferentially align any particular electrodes of electrodes 34 with branches of the vagus nerve. In some examples, electrodes 34 may operate in a bipolar or multi-polar configuration. For example, one or more electrodes of electrodes 34 may be configured as anodes and one or more of electrodes 34 may be configured as cathodes. Such a configuration is different than a unipolar configuration which would include an electrode located at a position relatively remote from the vagus nerve. In other examples, electrodes 34 may operate in unipolar configuration. In such a case, the return electrode(s) may be located on a portion of elongated member 30 in esophagus 24, distant from expandable member 32 (e.g., return electrode 37), or a return pad on the skin of the patient (e.g., like external electrode 46 of FIG. 4). The return pad on the skin may be placed on the abdomen near the lower esophagus to steer the current on a path the goes through the vagus nerve.

While electrodes 34 are depicted arranged in an array circumferentially separated from each other, the illustrated numbers and configurations of electrodes 34 are merely exemplary. Other configurations, e.g., numbers and positions of electrodes, are also contemplated. For example, in other implementations, expandable member 32 may include between 2 and 16 electrodes, inclusively. In some examples, the electrodes may be used for delivering different stimulation therapies or other electrical stimulations to respective stimulation sites within patient 14 or for monitoring at least one physiological marker of patient 14. For example, a set of electrodes may deliver stimulation at a first frequency to a first branch of the vagus nerve while a different set of electrodes may deliver stimulation at a second frequency to a second branch of the vagus nerve. In another example, a set of electrodes may deliver stimulation at a first frequency to a first location of first branch of the vagus nerve while a different set of electrodes may deliver stimulation at a second frequency to a second location of the first branch of the vagus nerve. This may allow for directional stimulation, such as blocking in a distal direction and stimulating in a proximal direction for an afferent stimulation. In some examples, the first frequency may be on the order of 1 Hz to 200 Hz for delivery of therapy (e.g., about 20 Hz) and the second frequency may be on the order of 1 kHz to 50 kHz for creating a nerve block (e.g., between about 10 kHz to about 20 kHz). In some examples, there may be separate electrodes of electrodes 34 for delivering blocking and stimulating, and these separate electrodes may be arranged along a transesophageal neurostimulation device rather than, or in addition to, circumferentially around the device.

In some examples, two or more of electrodes 34 may be used to measure an impedance of tissue to determine a location of a target stimulation location, such as branches of the vagus nerve and to indicate if the electrodes are in good contact with the tissue. To measure the impedance of tissue, transesophageal neurostimulation system 10A may source an electrical signal, such as current, to one electrode of electrodes 34, while another electrode of electrodes 34 sinks the electrical signal. Transesophageal neurostimulation system 10A may then determine the voltage between these two electrodes. Transesophageal neurostimulation system 10A may then determine the impedance of the tissue between the electrodes using a known value of the electrical signal sourced the determined voltage. For example, there may be different effects of stimulating the anterior and posterior branches of the vagus nerve. Therefore, it may be desirable to selectively stimulate both branches, or only a specific branch of the vagus nerve, such as only the posterior branch to avoid stimulating the heart. In some examples, transesophageal neurostimulation system 10A may be configured to detect branches of the vagus nerve, such as through the use of sensed impedances, and select the desired branch(es) to stimulate. Transesophageal neurostimulation system 10A may also be configured to select the appropriate electrode combination of electrodes 34 and/or other stimulation parameters to stimulate the desired branch(es).

In some examples, transesophageal neurostimulation system 10A may include sensors, such as sensor 6 shown disposed on the surface of expandable member 32, or be communicatively coupled to sensors, such as sensor 8, which may monitor one or more physiological parameters of patient 14. In some examples, sensor 6 and/or sensor 8 may be configured to monitor vital signs of patient 14 such as an electrocardiogram (ECG). Controller 28 may monitor the vital signs of patient 14 based on signals from sensor 6 and/or sensor 8 and provide an alarm or alert based on such monitoring when the vital signs depart from a predetermined range by more than a predetermined amount.

Transesophageal neurostimulation system 10A may change stimulation parameters, terminate stimulation, or initiate stimulation, based on the sensed parameter(s). Such parameters may include heart rate, heart rate variability, respiration rate, vagus nerve sensed activity, temperature, Electromyography (EMG), activity level of patient 14, pH of stomach 21 or esophagus 24, pressure in stomach 21 or esophagus 24, or other physiological parameters of patient

14. In this manner, transesophageal neurostimulation system 10A may be configured to operate as a closed-loop system using data from one or more sensors to adjust delivered electrical stimulation.

In some examples, transesophageal neurostimulation system 10A may automatically begin to deliver stimulation with minimal user input. For example, transesophageal neurostimulation system 10A may start stimulation in response to determining that a measured impedance is below a predetermined threshold, when expandable member 32 or expandable member 36 is inflated or otherwise expanded, or when a signal from sensor 7 is indicative of sensor 7 being in stomach 21 of patient 14.

Figure 3:
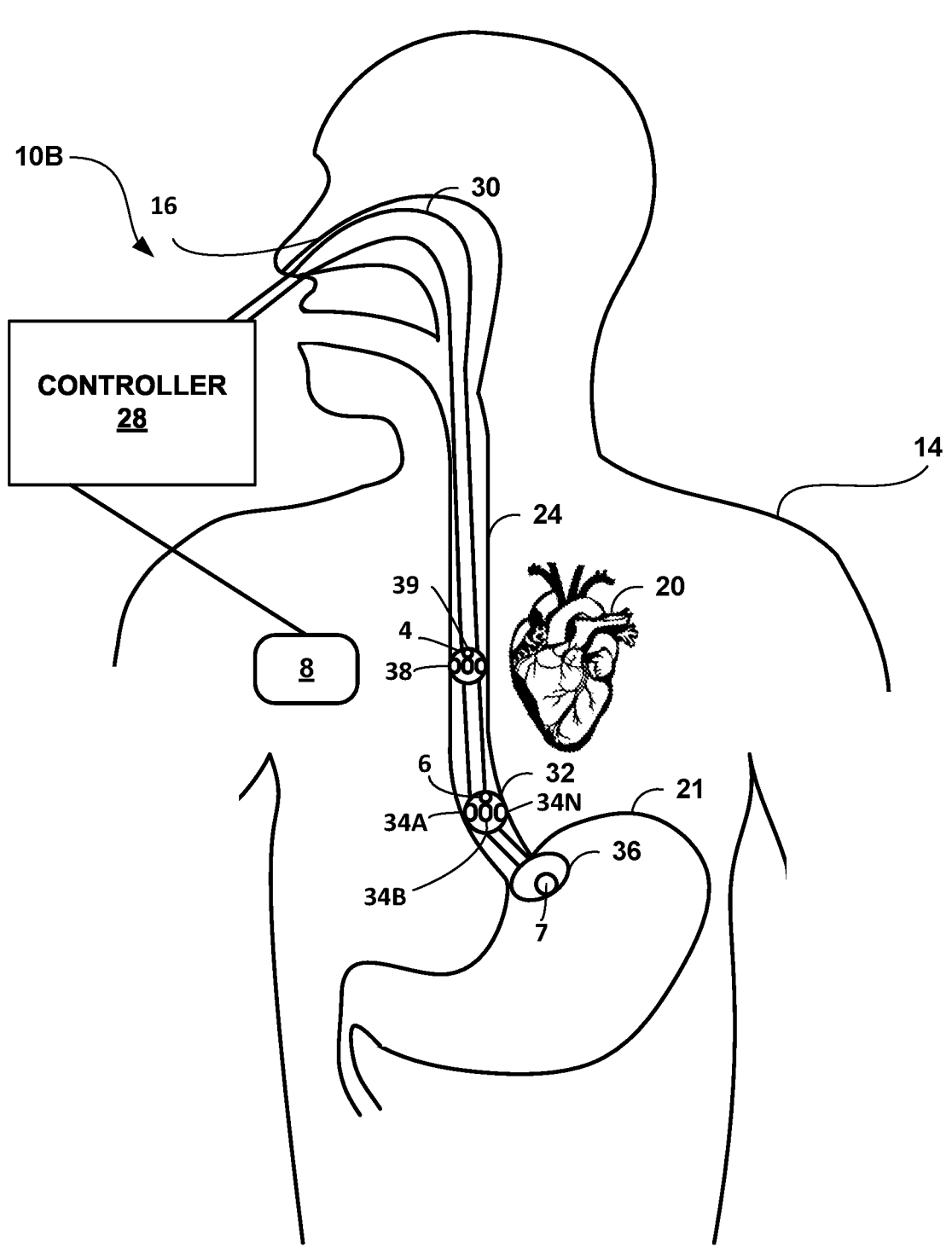
FIG. 3 is a conceptual diagram illustrating another example transesophageal neurostimulation system according to the techniques of this disclosure.

FIG. 3 is a conceptual diagram illustrating another example transesophageal neurostimulation system 10B according to the techniques of this disclosure. Transesophageal neurostimulation system 10B is similar to transesophageal neurostimulation system 10A of FIG. 2, except transesophageal neurostimulation system 10B also includes another expandable member 39. Expandable member 39 may function similarly to expandable member 32. In some examples, expandable member 39 includes one or more sensors, such as sensor 4 and/or a one or more electrodes, such as electrodes 38 which may be disposed on an outer surface of expandable member 39 or be located elsewhere. Electrodes 38 may be used to pace heart 20 while transesophageal neurostimulation system 10B is delivering stimulation to the vagus nerve via electrodes 34. As stimulation to the vagus nerve may lower a heart rate of patient 14, pacing heart 20 while delivering stimulation to the vagus nerve may offer some protection against the heart rate being lowered. For example, sensor 4 may sense a heart rate of patient 14 and transmit a signal indicative of the heart rate to controller 28. Controller 28 may determine whether the heart rate is below a predetermined threshold based on the signal from sensor 4. When the heart rate falls below the predetermined threshold, controller 28 may control electrodes 38 to begin pacing a chamber of heart 20 with a pacing electrical signal.

In some examples, transesophageal neurostimulation system 10B may use different electrical stimulation amplitudes to pace heart 20 than to stimulate the vagus nerve. For example, transesophageal neurostimulation system 10B may use a higher current to pace the heart than to stimulate the vagus nerve. In some examples, transesophageal neurostimulation system 10B may use different pulse widths to pace heart 20 than to stimulate the vagus nerve. For example, transesophageal neurostimulation system 10B may pace the heart using a stimulation signal with a pulse width in the range from about 2 ms to about 10 ms, and stimulate the vagus nerve with a stimulation signal with a pulse width in the range from about 50 μS to about 1000 μS. In some examples, transesophageal neurostimulation system 10B may use different frequencies to pace heart 20 than to stimulate the vagus nerve. For example, transesophageal neurostimulation system 10B may pace heart 20 using a stimulation signal with a frequency in the range of about 0.5 Hz to about 3 Hz and stimulate the vagus nerve using a stimulation signal with a frequency in the range of about 5 Hz to about 100 Hz.

Figure 4:
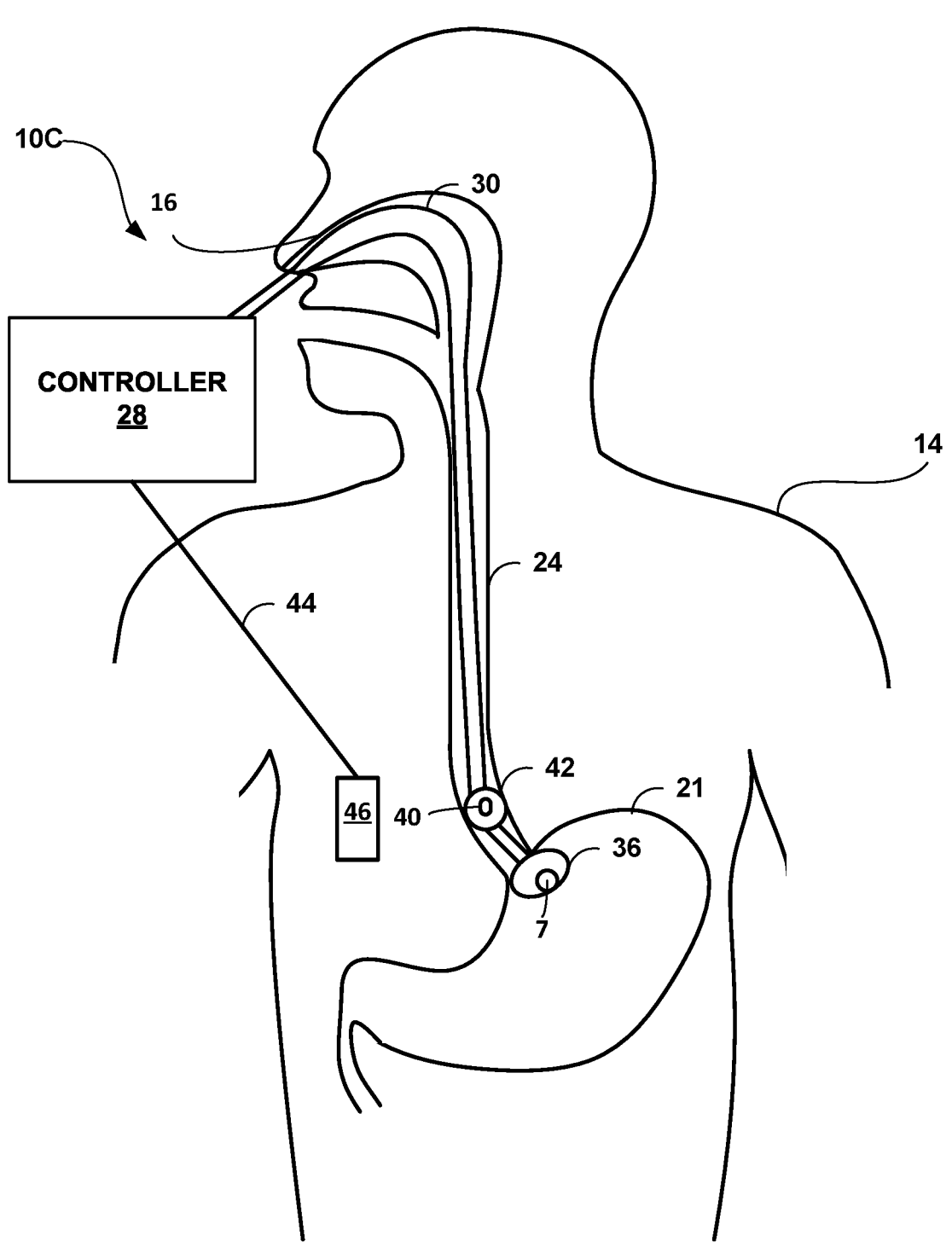
FIG. 4 is a conceptual diagram illustrating another example transesophageal neurostimulation system according to the techniques of this disclosure.

FIG. 4 is a conceptual diagram illustrating another example transesophageal neurostimulation system 10C according to the techniques of this disclosure. Transesophageal neurostimulation system 10C is similar to transesophageal neurostimulation system 10A of FIG. 2, except rather than having a plurality of electrodes (e.g., electrodes 34) disposed on the surface of expandable member 32, transesophageal neurostimulation system 10C, as shown, includes a single electrode 40 disposed on the surface of expandable member 42. In other examples, transesophageal neurostimulation system 10C may include more than one electrode disposed on the surface of expandable member 42, but may only activate a single of such electrodes at a time. In some examples, expandable member 42 may have more than one electrode which may be disposed on its surface or located elsewhere. In some examples, each of such electrodes may not form a closed loop so as reduce the risk of entanglement with another nasogastric tube, should another nasogastric tube be introduced or be already introduced into esophagus 24. Transesophageal neurostimulation system 10C also includes external electrode 46 configured to be deployed external to patient 14, such as on the exterior surface of skin of patient 14. Transesophageal neurostimulation system 10C may thus deliver stimulation in a unipolar manner with external electrode 46 acting as a return electrode. External electrode 46 may be communicatively coupled to controller 28 via a connection 44. Connection 44 may be a wired connection, such as an electrically conductive connection. In other examples, a return electrode may be located on elongated member 30 at a position distant from expandable member 42, but in esophagus 24.

In some examples, the electrode configuration of FIG. 4 may be used to pace the heart instead of the electrode configuration shown in FIG. 3.

Figure 5:
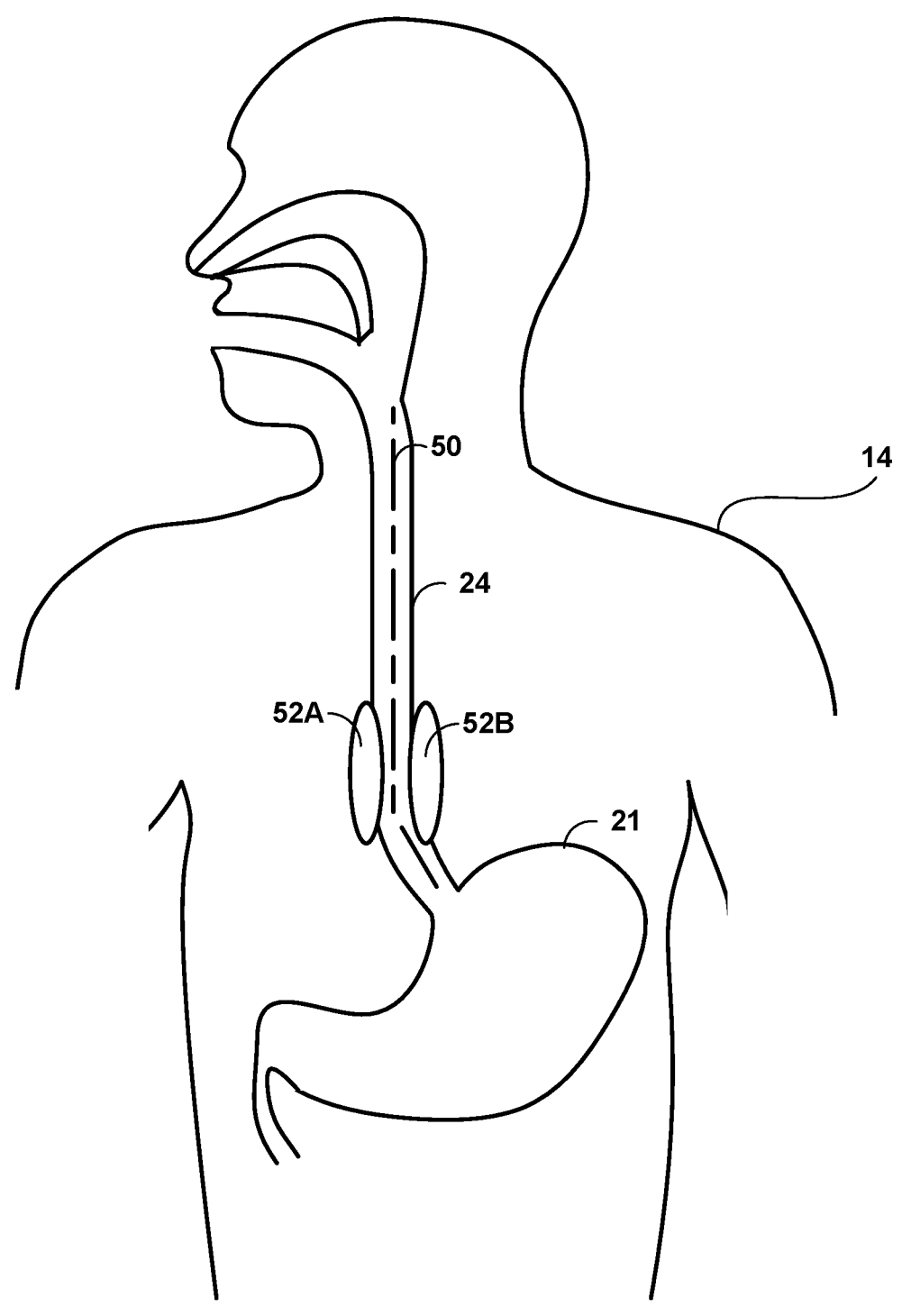
FIG. 5 is a conceptual diagram illustrating the esophageal axis and example stimulation fields which may be formed by a transesophageal neurostimulation system according to the techniques of this disclosure.

FIG. 5 is a conceptual diagram illustrating the esophageal axis and example stimulation fields which may be formed by a transesophageal neurostimulation system according to the techniques of this disclosure. In the example of FIG. 5, the transesophageal neurostimulation system is not shown for simplicity purposes. Longitudinal axis 50 of esophagus 24 is shown running the length of esophagus 24. In some examples, longitudinal axis 50 is an imaginary line through the center of esophagus 24 that runs the length of esophagus 24 from the pharynx (e.g., throat) to the stomach. In some examples, a transesophageal neurostimulation system (e.g., transesophageal neurostimulation system 10A, 10B, and/or 10C) may be configured to generate and deliver stimulation patterns that form fields predominantly aligned with axis 50 of esophagus 24. For example, a transesophageal neurostimulation system may generate and deliver stimulation patterns that form field 52A and/or field 52B (collectively "fields 52"). Such fields 52 may be predominantly longitudinal along axis 50 (e.g., more longitudinal than latitudinal) as shown in the example of FIG. 5.

Figure 6:
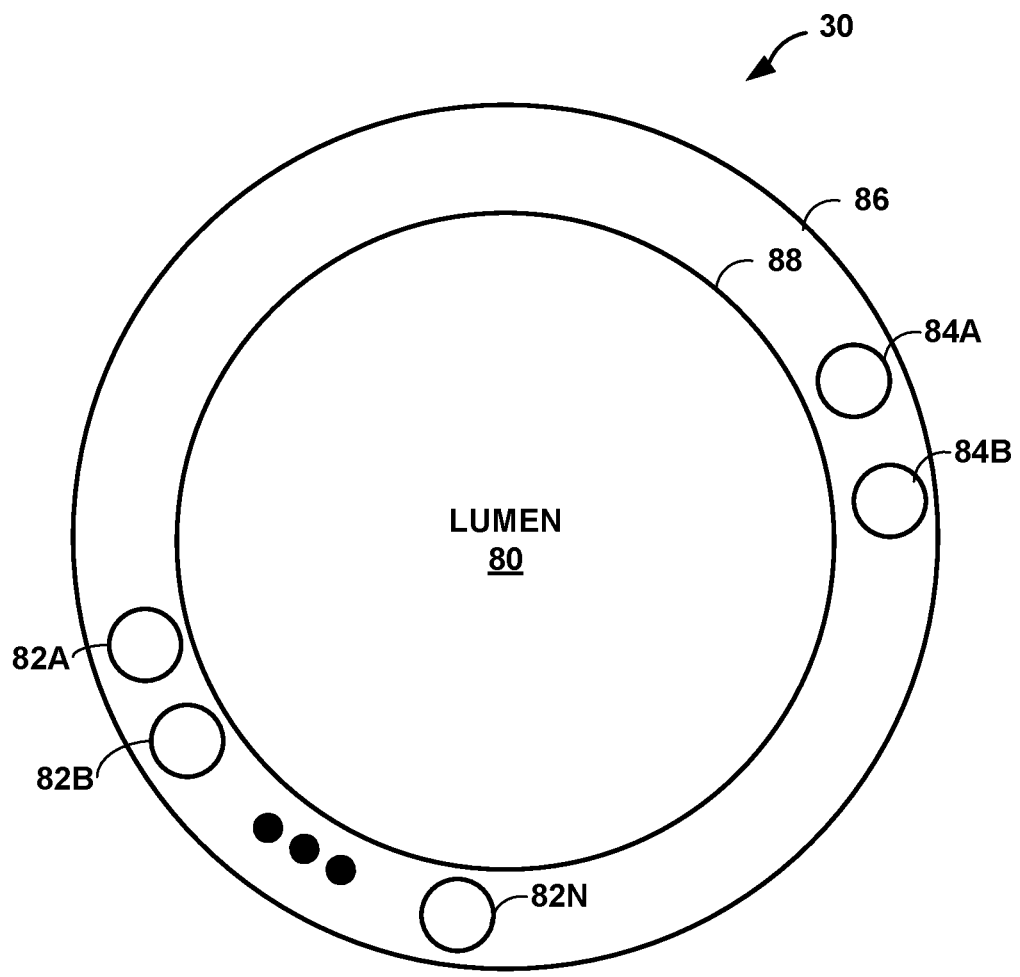
FIG. 6 is a conceptual diagram illustrating a cross section of elongated member 30 of FIGS. 2-4 according to the techniques of this disclosure.

FIG. 6 is a conceptual diagram illustrating a cross section of elongated member 30 of any of FIGS. 2-4 according to the techniques of this disclosure. In the example of FIG. 6, elongated member 30 includes an outer wall 86 and an inner wall 88 defining lumen 80. Lumen 80 may be configured to facilitate the introduction or removal of substances from esophagus 24 or stomach 21 of patient 14 (all of FIGS. 1-4). Elongated member 30 may also include one or more electrical conductors, such as conductors 82A, 82B, 82N, etc. (referred to hereinafter collectively as conductors 82). For example, elongated member 30 may include a conductor communicatively coupled to each of the electrodes disposed on expandable member 32 (FIG. 2), expandable members 32 and 39 (FIG. 3), or expandable member 42 (FIG. 4) and/or one or more conductors communicatively coupled to telemetry circuitry disposed in a portion of transesophageal neurostimulation system 10A or 10B intended to be internal to patient 14 when delivering stimulation. In some examples, electrical conductors 82 may each be configured to conduct electrical signals, such as a stimulation signal or a sensed signal between controller 28 and an associated electrode.

Elongated member 30 may also define lumen 84A and/or lumen 84B. Lumen 84A may be configured to carry a substance or to house a mechanism for expanding expandable member 32 or expandable member 42. Lumen 84B may be configured to be coupled to an external inflation source and carry a substance, or to house a mechanism for expanding expandable member 36. For example, the substance may include air, saline, or any other gas or liquid which may be capable of inflating a balloon in examples where expandable members 32, 39, 42 or 36 include balloons and elongated member 30 may include at least one fluid opening for injecting or removing such substance which may be fluidically coupled to lumen 84A and/or lumen 84B. In examples in which expandable members 32, 39, 42, or 36 do not include balloons, lumen 84A and/or lumen 84B may be configured to receive a deployment mechanism (e.g., a pull wire or a push wire) for deploying an expandable structure. In such a case, elongated member 30 may include an access opening to provide the clinician with access to the deployment mechanism. In some examples, rather than elongated member 30 defining lumen 84A and/or 54B, a distal portion of elongated member 30 and expandable members 32, 39, 42 or 36 may be configured to be contained within a removeable sheath that may be removed by a clinician after a portion of elongated member 30 is inserted into esophagus 24 which may cause any expandable members to expand.

Figure 7:
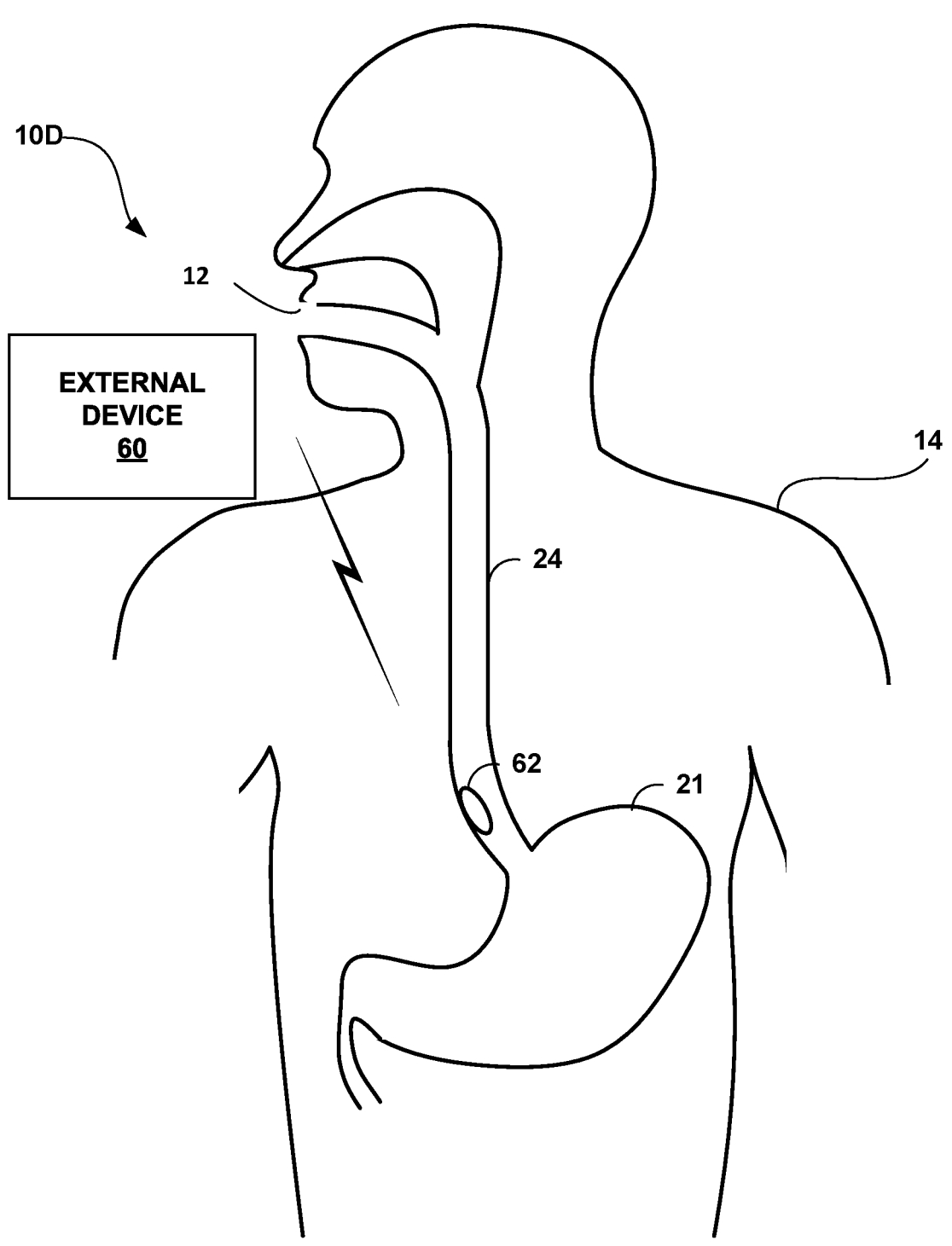
FIG. 7 is a conceptual diagram illustrating another example transesophageal neurostimulation system according to the techniques of this disclosure.

FIG. 7 is a conceptual diagram illustrating another example transesophageal neurostimulation system 10D according to the techniques of this disclosure. In the example of FIG. 7, transesophageal neurostimulation system 10D includes external device 60 and transesophageal neurostimulation device 62. Transesophageal neurostimulation device 62 may include one or more electrodes configured to deliver stimulation and/or sense one or more parameters of interest in esophagus 24 of patient 14. Transesophageal neurostimulation device 62 may be sized such that transesophageal neurostimulation device 62 is relatively easily swallowable via mouth 12 of patient 14 or deliverable via an insertion device into esophagus 24 of patient 14. In some examples, transesophageal neurostimulation device 62 and/or the insertion device may be biased, such as being bent or weighted, in such a manner as to position electrodes of transesophageal neurostimulation system 10D at locations more likely to be near the vagus nerve, such as anterior branch 26A and/or posterior branch 26B (both of FIG. 1). In some examples, transesophageal neurostimulation device 62 maybe a steerable or deflectable device (via external device 60 and/or an insertion device) and be configured to indent or penetrate electrodes of transesophageal neurostimulation device 62 into an inner wall of esophagus 24. For example, the insertion device may be flexible for insertion into patient 14, but include a bias to a shaft of the insertion device and/or a direction of deflection that facilitates the positioning of the electrodes of transesophageal neurostimulation device 62 at locations more likely to be near the vagus nerve.

Transesophageal neurostimulation device 62 may be configured to be attached temporarily to a wall of esophagus 24 of patient 14. For example, transesophageal neurostimulation device 62, an external device, an insertion device (which may be configured to insert transesophageal neurostimulation device 62 into esophagus 24), or implantation device may be configured to apply a relatively mild suction force to pull in a mucosal flap (not shown) of esophagus 24 and transesophageal neurostimulation device 62 or the insertion device may then attach transesophageal neurostimulation device 62 to the mucosal flap of esophagus 24. In such a case, transesophageal neurostimulation device 62 may remain attached for a few days or so, and then detach from the mucosal flap of esophagus 24. In another example, an insertion device or implantation device may place transesophageal neurostimulation device 62 in a sub-mucosal pocket (between the mucosa and the muscle layers). In another example, a stent-like structure may be used that biodegrades over time. For example, transesophageal neurostimulation device 62 may include the stent-like structure or the stent-like structure may be configured to house transesophageal neurostimulation device 62. This stent-like structure may be configured to attach transesophageal neurostimulation device 62 to an internal wall of esophagus 24. In another example, transesophageal neurostimulation device 62 may include a balloon that self-deflates or an expandable structure that is digested over a certain amount of time which is configured to hold transesophageal neurostimulation device 62 in place within esophagus 24 for the certain amount of time.

In some examples, transesophageal neurostimulation device 62 may be configured to be attached temporarily to a wall of esophagus 24 of patient 14 via techniques described in U.S. Pat. No. 6,754,536, granted on Jun. 22, 2004, entitled "Implantable medical device affixed internally within the gastrointestinal tract"; U.S. Pat. No. 6,689,056, granted on Feb. 10, 2004, entitled "Implantable monitoring probe"; U.S. Pat. No. 7,580,751, granted on Aug. 25, 2009, entitled "Intra-luminal device for gastrointestinal stimulation"; U.S. Pat. No. 8,216,158, granted on Jul. 10, 2021, entitled "Implantation of a medical device within a lumen"; or U.S. Pat. No. 8,301,265, granted on Oct. 30, 2012, entitled "Selective depth electrode deployment for electrical stimulation", each of which is hereby incorporated by reference in its entirety.

Transesophageal neurostimulation device 62 may deliver neurostimulation to a target location within patient 14, such as one or more branches of a vagus nerve of patient 14. Transesophageal neurostimulation device 62 may also be configured to detach itself from the wall of esophagus 24 and pass through the remainder of a digestive system of patient 14. For example, transesophageal neurostimulation device 62 may be a disposable device that may pass from patient 14 in stool of patient 14.

Transesophageal neurostimulation device 62 may be self-powered (e.g., include a battery) and controlled or may be externally powered and controlled. In some examples, transesophageal neurostimulation device 62 may attach itself to the wall of esophagus 24 in response to receiving a command signal from external device 60. In some examples, transesophageal neurostimulation device 62 may attach itself to the wall of esophagus 24 in response to sensed parameters, such as sensed impedances of tissue of patient 14 being indicative of transesophageal neurostimulation device 62 being within a predetermined distance of a target location within patient 14. In some examples, transesophageal neurostimulation device 62 may attach itself to the wall of esophagus 24 in response to a first predetermined time period having passed.

In some examples, transesophageal neurostimulation device 62 may detach itself from the wall of esophagus 24 in response to receiving a command signal from external device 60. In some examples, transesophageal neurostimulation device 62 may detach itself from the wall of esophagus 24 in response to one or more sensed parameters being indicative of the health of patient 14 having improved. For example, transesophageal neurostimulation device 62 may compare one or more sensed parameters to one or more thresholds and determine whether to detach itself from the wall of esophagus 24 based on the comparison(s). In some examples, transesophageal neurostimulation device 62 may detach itself from the wall of esophagus 24 in response to a second predetermined time period having passed.

Transesophageal neurostimulation device 62 may have a biocompatible housing, which may be formed from titanium, stainless steel, a liquid crystal polymer, polymer or the like, and include one or more electrodes integrated onto an exterior surface of transesophageal neurostimulation device 62.

Transesophageal neurostimulation system 10D may also include an external device 60, as shown in FIG. 7. External device 60 may be an example of a computing device. In some examples, external device 60 may be a clinician programmer or patient programmer. In some examples, external device 60 may be a device for inputting stimulation programs or stimulation parameters into transesophageal neurostimulation device 62. In some examples, external device 60 may be a wearable communication device, with a therapy request input integrated into a key fob or a wristwatch, handheld computing device, smart phone, computer workstation, or networked computing device. External device 60 may include a user interface that is configured to receive input from a user (e.g., patient 14, a caretaker, or a clinician). In some examples, the user interface includes, for example, a keypad and a display, which may for example, be a liquid crystal display (LCD) or light emitting diode (LED) display. In some examples, the user interface may include a turnable knob or a representation of a turnable knob. The keypad may take the form of an alphanumeric keypad or a reduced set of keys associated with particular functions. External device 60 may additionally or alternatively include a peripheral pointing device, such as a mouse, via which a user may interact with the user interface. In some examples, a display of external device 60 may include a touch screen display, and a user may interact with external device 60 via the display.

A user may also interact with external device 60 to communicate with transesophageal neurostimulation device 62. Such a user may interact with external device 60 to retrieve physiological or diagnostic information from transesophageal neurostimulation device 62. The user may also interact with external device 60 to program transesophageal neurostimulation device 62, e.g., select values for the stimulation parameter with which transesophageal neurostimulation device 62 generates and delivers stimulation and/or the other operational parameters of transesophageal neurostimulation device 62, such as magnitudes of stimulation energy, user requested periods for stimulation or periods to prevent stimulation, or any other such user customization of therapy.

For example, the user may use external device 60 to retrieve information from transesophageal neurostimulation device 62 relating to a heartrate of patient 14, a heart rate variability over time, respiration rate, vagus nerve sensed activity, temperature, EMG, activity level of patient 14, or the like. As another example, the user may use external device 60 to retrieve information from transesophageal neurostimulation device 62 relating to the performance or integrity of transesophageal neurostimulation device 62. In some examples, this information may be presented to the user as an alert if a system condition that may affect the efficacy of therapy is detected.

Patient 14 or a clinician may, for example, use a keypad or touch screen of external device 60 to request transesophageal neurostimulation device 62 to deliver or terminate the electrical stimulation. For example, patient 14 may use external device 60 to provide a therapy request to control the delivery of the electrical stimulation "on demand," e.g., when patient 14 deems the second stimulation therapy desirable. This request may be a therapy trigger event used to terminate electrical stimulation.

External device 60 may provide a notification to patient 14 or a clinician when the electrical stimulation is being delivered or notify patient 14 of the prospective termination of the electrical stimulation. In such examples, external device 60 may display a visible message, emit an audible alert signal or provide a somatosensory alert (e.g., by causing a housing of external device 60 to vibrate). In other examples, the notification may indicate when therapy is available (e.g., a countdown in minutes, or indication that therapy is ready).

Transesophageal neurostimulation device 62 and external device 60 may communicate via wireless communication using any techniques known in the art. Examples of communication techniques may include, for example, low frequency or radiofrequency (RF) telemetry, but other techniques are also contemplated. In some examples, external device 60 may include a programming lead that may be placed proximate to the patient's body near the transesophageal neurostimulation device 62 in order to improve the quality or security of communication between transesophageal neurostimulation device 62 and external device 60.

In some examples, in addition to being a swallowable device or alternatively, transesophageal neurostimulation device 62 may be an implantable device that may be implanted sub-mucosally and/or between the layers of longitudinal and circumferential muscle layers of esophagus 24.

Figures 8A, 8B, 8C:
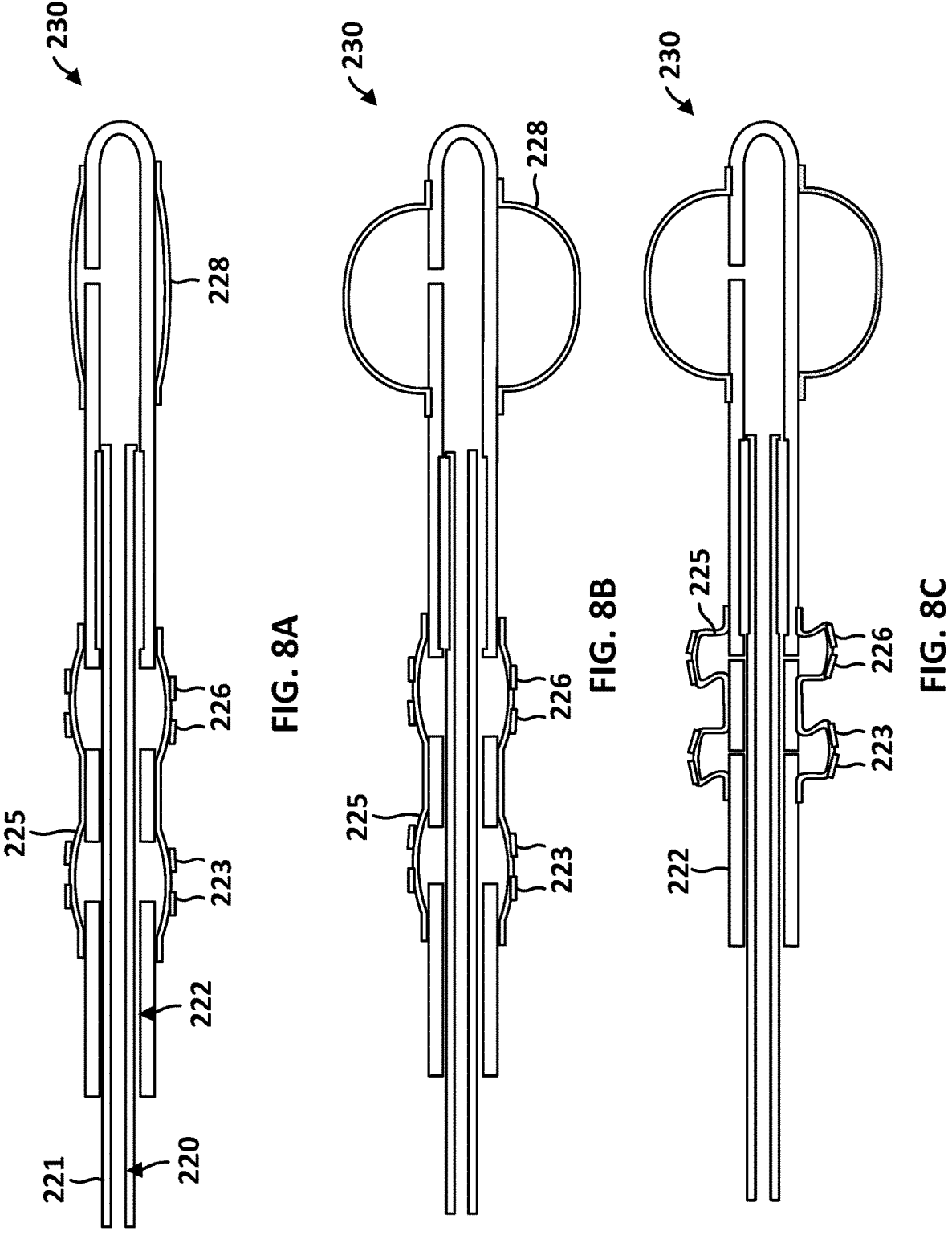
FIGS. 8A-8C are conceptual diagrams illustrating three views of different configurations of a respective portion of an example transesophageal neurostimulation system according to the techniques of this disclosure.

FIGS. 8A-8C are conceptual diagrams illustrating three views of a respective portion of an example transesophageal neurostimulation system 230 according to the techniques of this disclosure. FIG. 8A depicts a portion of transesophageal neurostimulation system 230. An elongated member 221 of transesophageal neurostimulation system 230 may define an inner inflation lumen 220 which may be fluidically coupled to expandable member 228. Inflation lumen 220 may be configured to carry a substance to, or pressurize the substance within, expandable member 228 from a pump or other reservoir in fluid communication with inflation lumen 220. For example, the substance may include air, saline, or any other gas or liquid which may be capable of inflating a balloon in examples where expandable member 228 includes a balloon. Elongated member 221 of transesophageal neurostimulation system 230 may include at least one fluid opening for injecting or removing such substance which may be fluidically coupled to inflation lumen 220. While shown as a balloon in the example of FIG. 8A, in some examples, expandable member 228 may be another structure configured to expand in stomach 21 of patient 14. In such examples, lumen 220 may house a mechanism for expanding expandable member 228. In examples in which expandable member 228 does not include a balloon, lumen 220 may be configured to receive a deployment mechanism (e.g., a pull wire or a push wire) for deploying an expandable structure. In such a case, elongated member 221 may include an access opening to provide the clinician with access to the deployment mechanism. Transesophageal neurostimulation system 230 may also include an outer electrode actuator 222 configured to expand membrane 225 to move proximal electrodes 223 and/or distal electrodes 226 from the state shown in FIG. 8A outward toward the tissue of or to contact the tissue of esophagus 24 of patient 14 when mechanically manipulated, for example, by a clinician or device.

For example, with transesophageal neurostimulation system 230 in the state of FIG. 8A (proximal electrodes 223, distal electrodes 226, and expandable member 228 in a non-expanded state), a clinician may pass the distal end of transesophageal neurostimulation system 230 through nasal cavity 16 or mouth 12 of patient until expandable member 228 is located in stomach 21 of patient 14. The position of expandable member 228 may be confirmed to be in stomach 21 of patient 14 through a pH sensor, pressure sensor, x-ray, fluoroscopy, sampling of fluid, auscultation, and/or through other techniques. The clinician may then expand expandable member 228, for example, by inflating expandable member 228 with a gas or liquid. Such a state is depicted in FIG. 8B.

The clinician may then manipulate transesophageal neurostimulation system 230, for example, by pulling transesophageal neurostimulation system 230 retrograde to position expandable device 228 so that expandable device 228 is inside stomach 21 at the entrance to stomach 21. If desired, the clinician may secure the location of expandable device 228 by securing an external portion of transesophageal neurostimulation system 230 to patient 14 or to something else external to patient 14 using tape or other techniques.

The clinician may then manipulate outer electrode actuator 222, for example, by pushing or twisting outer electrode actuator 222 toward the distal end of transesophageal neurostimulation system 230 to expand membrane 225 and extend proximal electrodes 223 and/or distal electrodes 226 outward toward the tissue of or to contact the tissue of esophagus 24. Such a state is depicted in FIG. 8C. In some examples, proximal electrodes 223 and or distal electrodes 226 may comprise flex circuits or be electrodes disposed on flexible material, such as membrane 225. By manipulating outer electrode actuator 222, the clinician may move outer electrode actuator 222 in such a manner as to effectively close the gaps in outer electrode actuator 222 forcing proximal electrodes 223 and/or distal electrodes 226 outward with respect to transesophageal neurostimulation system 230.

In the example of FIGS. 8A-8C, each flexible section is shown as having two electrodes disposed thereon. However, in some examples, one or more of such flexible sections may have a single or more than two electrodes. If three electrodes are present, in some examples, the outer electrodes could be electrically connected to improve the delivery of stimulation or to improve sensing. For example, the middle electrode may be a cathode and the outer two electrodes may be anodes in a guarded cathode electrode combination. In some examples, the flexible sections completely surround the gaps in outer electrode actuator 222. In some examples, rather than completely surround the gaps in outer electrode actuator 222, each area having at least one flexible section may have between one and ten flexible sections so as to cover only a portion of the gaps in outer electrode actuator 222.

In the example of FIGS. 8A-8C, two areas having gaps and electrodes are shown. In some examples, there may be only one such area. In other examples, there may be more than two such areas, for example there may be three or four such areas.

As shown in FIGS. 8A-8C, outer electrode actuator 222 includes three portions. The distal portion is coupled to expandable member 228, the middle portion is disposed between proximal electrodes 223 and distal electrodes 226 (when in an unexpanded state), and the proximal portion extends proximally out of patient 14. For example, proximal electrodes 223 and distal electrodes 226 may be extended by pushing the proximal section of outer electrode actuator 222 distally until all sections of outer electrode actuator 222 are adjacent to each other. Proximal electrodes 223 and distal electrodes 226 may be retracted by pulling the proximal portion proximally. In this manner, when removing the distal end of transesophageal neurostimulation system 230 from patient 14, proximal electrodes 223 and distal electrodes 226 may be automatically retracted due to the pulling or twisting (e.g., in a reverse direction) force exerted on outer electrode actuator.

In some examples, rather than outer electrode actuator 222 having a plurality of distinct and separate sections, outer electrode actuator 222 may include a single piece having compressible sections which may allow for proximal electrodes 223 and distal electrodes 226 to be extended. In some examples, such compressible sections may be continuous or interrupted spiral cut. In some examples, transesophageal neurostimulation system 230 may include sensors to guide stimulation, such as accelerometers or other sensors described herein.

Figures 9A, 9B, 9C:
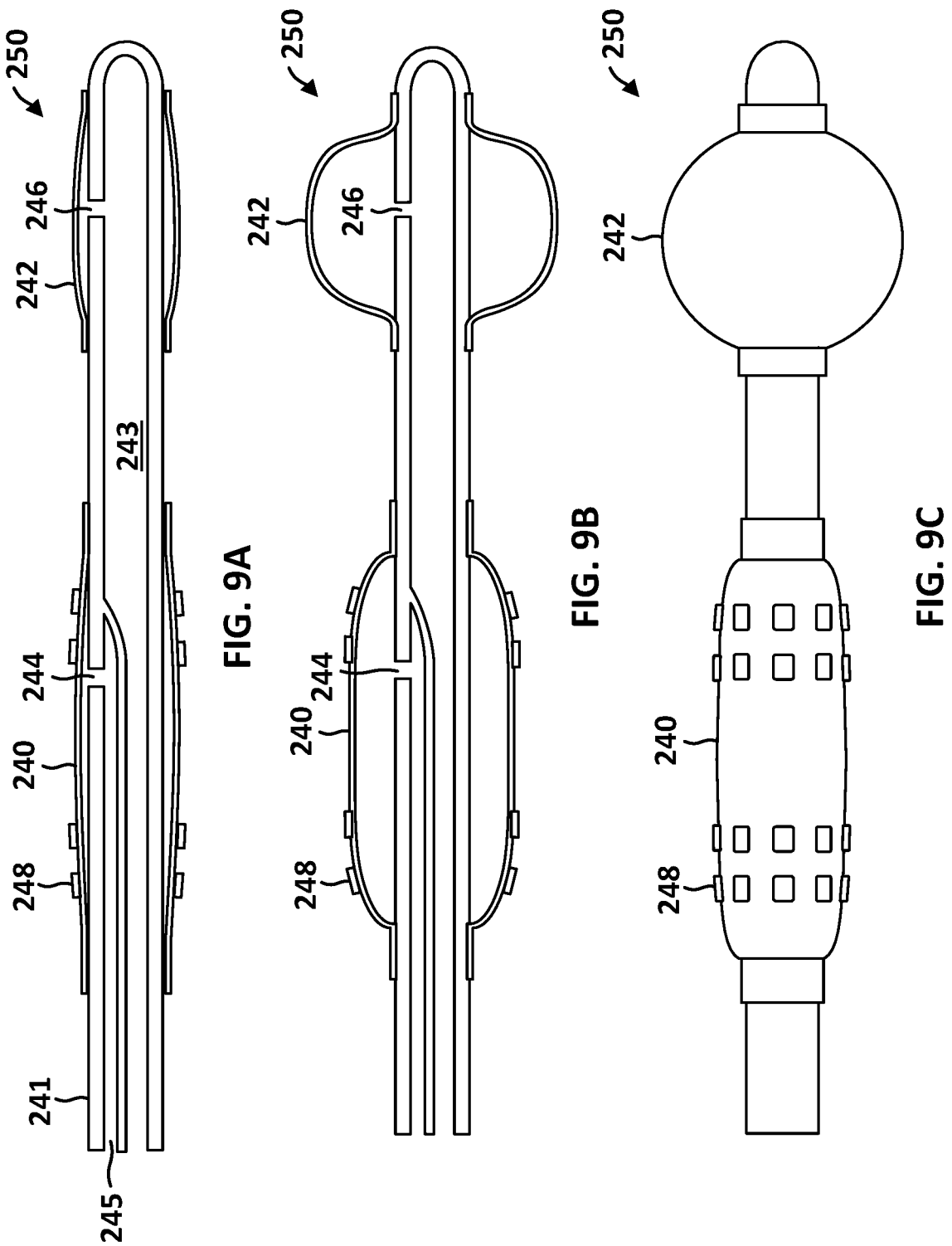
FIGS. 9A-9C are conceptual diagrams illustrating three views of a respective portion of another example transesophageal neurostimulation system according to the techniques of this disclosure.

FIGS. 9A-9C are conceptual diagrams illustrating three views of a respective portion of another example transesophageal neurostimulation system 250 according to the techniques of this disclosure. FIG. 9A depicts transesophageal neurostimulation system 250 in an unexpanded state. Transesophageal neurostimulation system 250 includes expandable member 242, which is shown as a balloon, but may be any type of expandable member. Elongated member 241 may define lumen 243 and lumen 245. Opening 246 may be fluidically coupled to lumen 243 which may be configured to transport a liquid or gas which may be used to expand expandable member 242. Expandable member 242 may be configured to anchor transesophageal neurostimulation system 250 to patient 14 when expanded, for example, in stomach 21 of patient 14. Expandable member 240 may have one or more electrodes 248 disposed on an external surface of expandable member 240. Expandable member 240 is shown as a balloon, but may be any type of expandable member. Opening 244 may be fluidically coupled to lumen 245 which may be configured to transport a liquid or gas which may be used to expand expandable member 240. Expandable member 240 may be configured to expand moving one or more electrodes 248 outward towards the walls of esophagus 24 of patient 14. In some examples, one or more electrodes 248 may be flat or approximately flat against the outer surface of expandable member 240. In some examples, one or more electrodes 248 may protrude from the outer surface of expandable member 240. By including lumen 245, opening 244, lumen 243, and opening 246, expandable member 240 and expandable member 242 may be separately expandable, facilitating independent control of anchoring and electrode expansion. FIG. 9B shows transesophageal neurostimulation system 250 in an expanded state. FIG. 9C shows an external view of transesophageal neurostimulation system 250 in an expanded state.

In the example where expandable member 240 is a balloon, transesophageal neurostimulation system 250 may be easier to assemble, manufacture, and/or use than transesophageal neurostimulation system 230 of FIGS. 8A-8C. Transesophageal neurostimulation system 250 may also provide for an even and controllable radial force when expandable member 240 is being expanded. In some examples, expandable member 240 may be expanded in a variety of shapes.

Figures 10A, 10B, 10C:
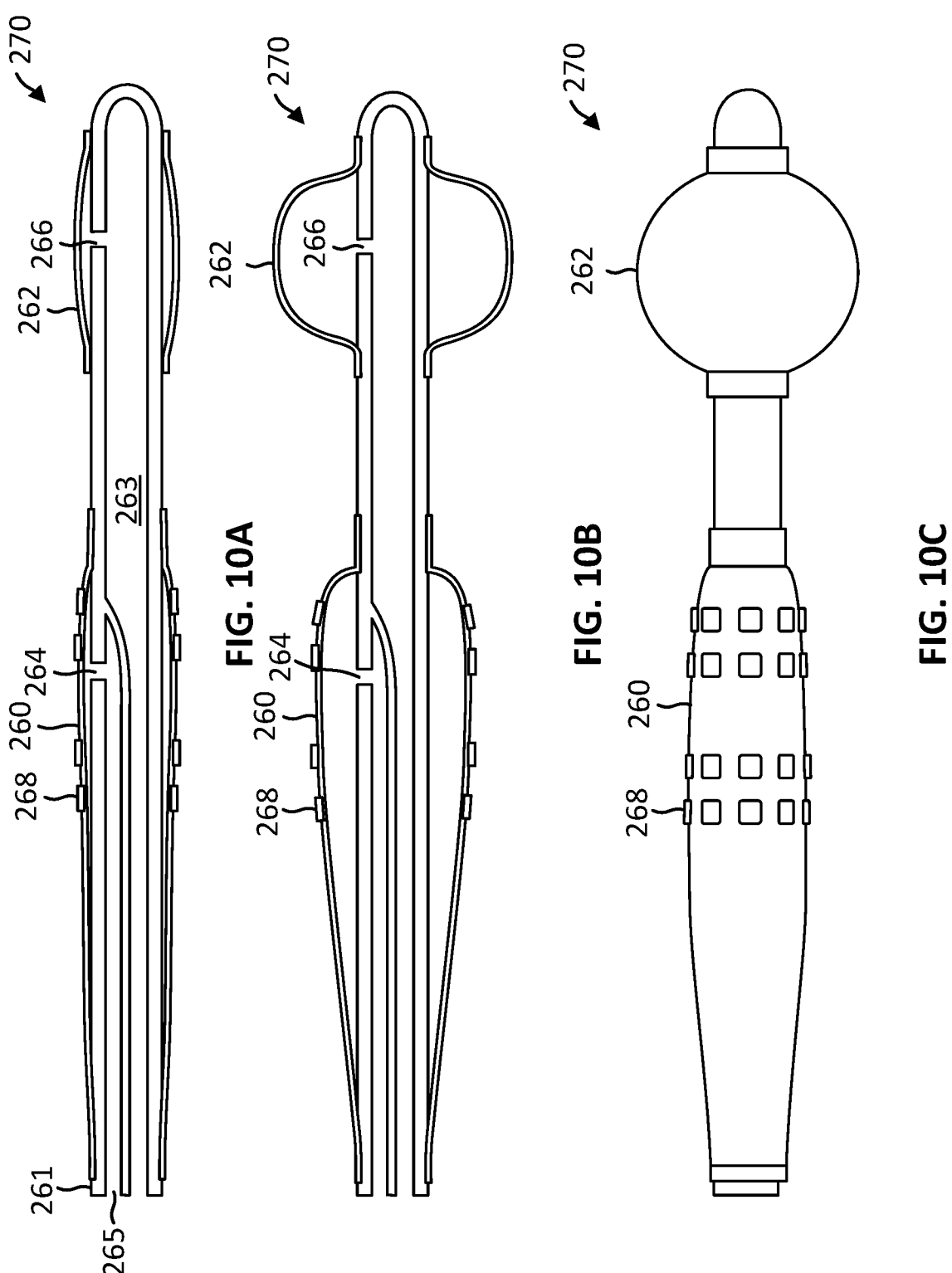
FIGS. 10A-10C are conceptual diagrams illustrating three views of a respective portion of another example transesophageal neurostimulation system according to the techniques of this disclosure.

FIGS. 10A-10C are conceptual diagrams illustrating three views of a respective portion of another example transesophageal neurostimulation system 270 according to the techniques of this disclosure. FIG. 10A depicts transesophageal neurostimulation system 270 in an unexpanded state. Transesophageal neurostimulation system 270 includes expandable member 262, which is shown as a balloon, but may be any type of expandable member. Elongated member 261 may define lumen 263 and lumen 265. Opening 266 may be fluidically coupled to lumen 265 which may be configured to transport a liquid or gas which may be used to expand expandable member 262. Expandable member 262 may be configured to anchor transesophageal neurostimulation system 270 to patient 14 when expanded, for example, in stomach 21 of patient 14. Expandable member 260 may have one or more electrodes 268 disposed on an external surface of expandable member 260. In some examples, one or more electrodes 268 may be flat or approximately flat against the outer surface of expandable member 260. In some examples, one or more electrodes 268 may protrude from the outer surface of expandable member 260. Expandable member 260 is shown as a balloon, but may be any type of expandable member. Opening 264 may be fluidically coupled to lumen 263 which may be configured to transport a liquid or gas which may be used to expand expandable member 260. Expandable member 260 may be configured to expand moving one or more electrodes 268 outward towards the walls of esophagus 24 of patient 14. By including lumen 265, opening 264, lumen 263, and opening 266, expandable member 260 and expandable member 262 may be separately expandable, facilitating independent control of anchoring and electrode expansion. Expandable member 260 may be gradually tapered towards the proximal edge as shown in FIGS. 10B-10C. In this manner, transesophageal neurostimulation system 270 may reduce the peristaltic force from esophagus 24 compared to transesophageal neurostimulation system 250 of FIGS. 9A-9C that may otherwise propel a portion of transesophageal neurostimulation system 270 further into stomach 21 of patient 14. FIG. 10B shows transesophageal neurostimulation system 270 in an expanded state. FIG. 10C shows an external view of transesophageal neurostimulation system 270 in an expanded state.

Figures 11A, 11B, 11C:
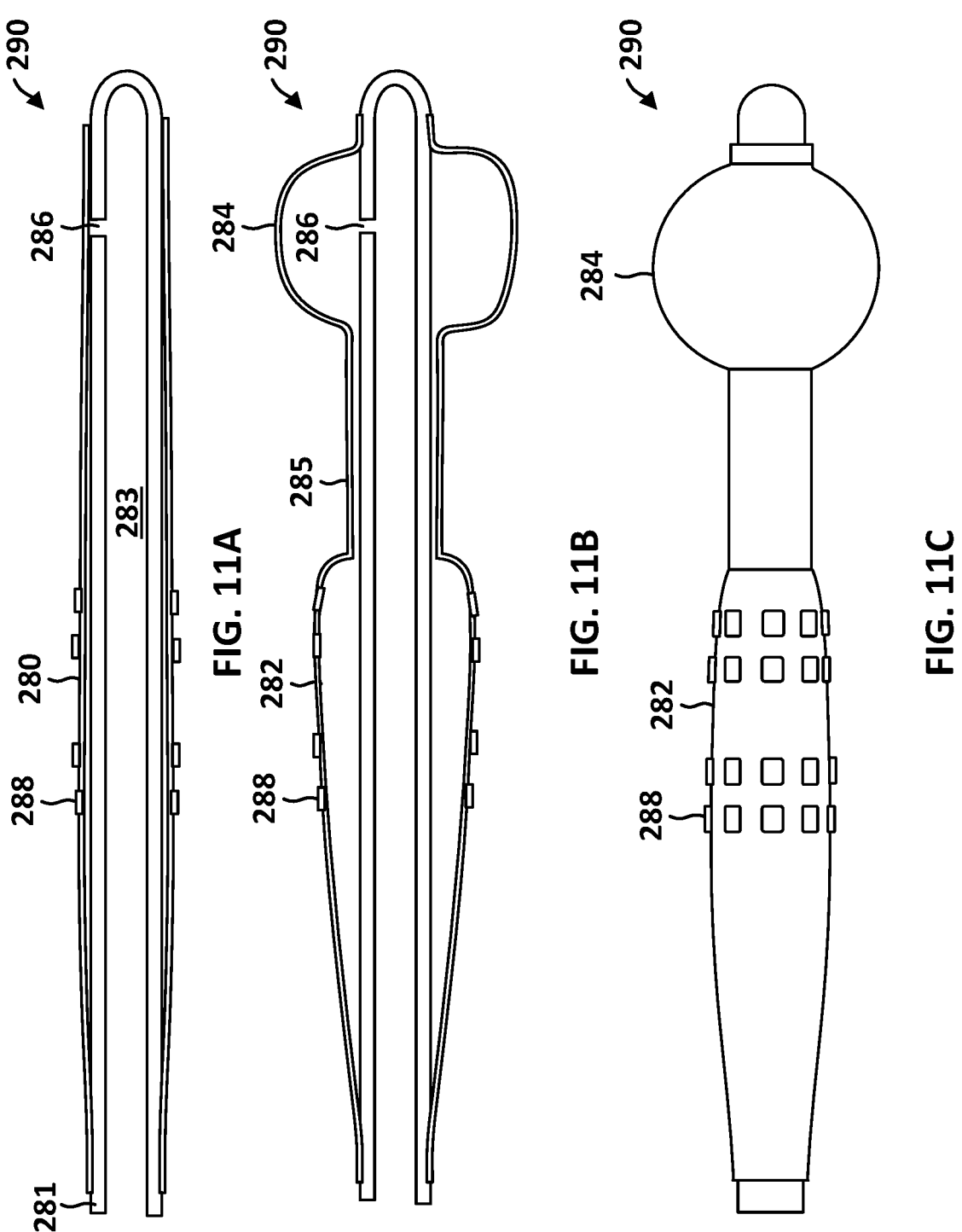
FIGS. 11A-11C are conceptual diagrams illustrating three views of a respective portion of another example transesophageal neurostimulation system according to the techniques of this disclosure.

FIGS. 11A-11C are conceptual diagrams illustrating three views of a respective portion of another example transesophageal neurostimulation system according to the techniques of this disclosure. FIG. 11A depicts transesophageal neurostimulation system 290 in an unexpanded state. Transesophageal neurostimulation system 290 includes expandable member 280, which is shown as a balloon, but may be any type of expandable member. Rather than having two openings and two lumens to separately control the expansion of two different expandable members, transesophageal neurostimulation system 290 includes one lumen 283 and one opening 286. For example, elongated member 281 may define lumen 283. Opening 286 may be fluidically coupled to lumen 283 which may be configured to transport a liquid or gas which may be used to expand expandable member 280. Expandable member 280 may have one or more electrodes 288 disposed on an external surface of expandable member 280. In some examples, one or more electrodes 288 may be flat or approximately flat against the outer surface of expandable member 280. In some examples, one or more electrodes 288 may protrude from the outer surface of expandable member 280. FIG. 11B shows transesophageal neurostimulation system 290 in an expanded state. Expandable member 280 may have a first portion 284 which may be configured to anchor transesophageal neurostimulation system 290 to patient 14. First portion 284 may be located in stomach 21 of patient 14 when expanded to anchor transesophageal neurostimulation system 290 to patient 14. Second portion 282 may be configured to expand moving one or more electrodes 288 outward towards the walls of esophagus 24 of patient 14. Third portion 285 may be adhered to elongated member 281 or may be constructed of a different material than second portion 282 or first portion 284, such as a material that is more rigid than the material of second portion 282 or first portion 284. First portion 284 and second portion 282 may be constructed of the same material or different materials, for example, of different rigidities to allow for different amounts of expansion. Second portion 282 may be gradually tapered towards the proximal edge as shown in FIGS. 11B-11C. In this manner, transesophageal neurostimulation system 290 may reduce the peristaltic force from esophagus 24 compared to transesophageal neurostimulation system 250 of FIGS. 9A-9C that may otherwise propel a portion of transesophageal neurostimulation system 290 further into stomach 21 of patient 14. FIG. 11C shows an external view of transesophageal neurostimulation system 290 in an expanded state.

Figures 12A, 12B, 13A, 13B, 14A, 14B, 15A, 15B:
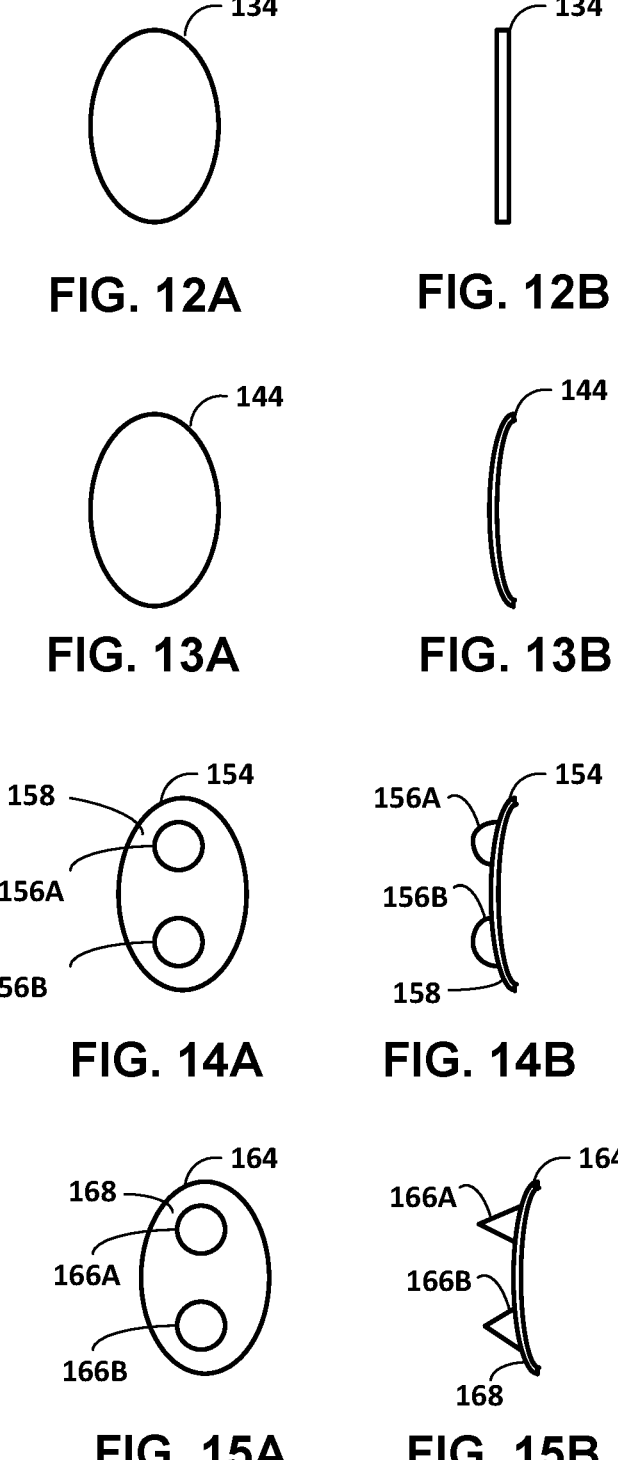
FIGS. 12A and 12B are conceptual diagrams illustrating a top view and side view, respectively, of an example electrode according to the techniques of this disclosure.
FIGS. 13A and 13B are conceptual diagrams illustrating a top view and side view, respectively, of another example electrode according to the techniques of this disclosure.
FIGS. 14A and 14B are conceptual diagrams illustrating a top view and side view, respectively, of another example electrode according to the techniques of this disclosure.
FIGS. 15A and 15B are conceptual diagrams illustrating a top view and side view, respectively, of another example electrode according to the techniques of this disclosure.

FIGS. 12A and 12B are conceptual diagrams illustrating a top view and side view, respectively, of an example electrode 134 according to the techniques of this disclosure. In FIG. 12A, the top view of electrode 134 is shown as being oval shaped, but may be of any shape. In FIG. 12B, the side view of electrode 134 is shown as being planar, e.g., not a closed loop. Electrode 134 may be an example of any of electrodes 34 (FIGS. 2-3), electrodes 38 (FIG. 3), electrode 40 (FIG. 4), external electrode 46 (FIG. 4), electrodes of transesophageal neurostimulation device 62 (FIG. 7), proximal electrodes 223 or distal electrodes 226 (FIGS. 8A-8C), one or more electrodes 248 (FIGS. 9A-9C), one or more electrodes 268 (FIGS. 10A-10C), one or more electrodes 288 (FIGS. 11A-11C) or other electrodes of this disclosure.

FIGS. 13A and 13B are conceptual diagrams illustrating a top view and side view, respectively, of another example electrode 144 according to the techniques of this disclosure. In FIG. 13A, the top view of electrode 144 is shown as being oval shaped, but may be of any shape. In FIG. 13B, the side view of electrode 144 is shown as being non-planar, such as curved in shape. For example, electrode 144 may be configured to conform to a shape of an expandable member, such as expandable members 32 (FIGS. 2-3), 39 (FIG. 3), 42 (FIG. 4) to a shape of an internal wall of esophagus 24, or, in the event electrode 144 represents external electrode 46, to a shape of a body of patient 14. Electrode 144 may be an example of any of electrodes 34 (FIGS. 2-3), electrodes 38 (FIG. 3) electrode 40 (FIG. 4), external electrode 46 (FIG. 4), electrodes of transesophageal neurostimulation device 62 (FIG. 7), proximal electrodes 223 or distal electrodes 226 (FIGS. 8A-8C) one or more electrodes 248 (FIGS. 9A-9C), one or more electrodes 268 (FIGS. 10A-10C), one or more electrodes 288 (FIGS. 11A-11C), or other electrodes of this disclosure.

FIGS. 14A and 14B are conceptual diagrams illustrating a top view and side view, respectively, of another example electrode 154 according to the techniques of this disclosure. In FIG. 14A, the top view of electrode 154 is shown as being oval shaped, but may be of any shape. In FIG. 14B, the side view of electrode 154 is shown as being non-planar, such as curved in shape. For example, electrode 154 may be configured to conform to a shape of an expandable member, such as expandable members 32 (FIGS. 2-3), 39 (FIG. 3) or 42 (FIG. 4), to a shape of an internal wall of esophagus 24, or, in the event electrode 154 represents external electrode 46, to a shape of a body of patient 14. Electrode 154 may be an example of any of electrodes 34 (FIGS. 2-3), electrodes 38 (FIG. 3) electrode 40 (FIG. 4), external electrode 46 (FIG. 4), electrodes of transesophageal neurostimulation device 62 (FIG. 7), proximal electrodes 223 or distal electrodes 226 (FIGS. 8A-8C), one or more electrodes 248 (FIGS. 9A-9C), one or more electrodes 268 (FIGS. 10A-10C), or one or more electrodes 288 (FIGS. 11A-11C), or other electrodes of this disclosure.

While electrode 154 is shown as being curved in shape, electrode 154 may alternatively be flat or of a different shape.

Electrode 154 includes one or more protrusions, e.g., protrusion 156A and protrusion 156B extending from a surface 158 of electrode 154. Protrusions 156A and 156B may be configured to indent a wall of esophagus 24. By indenting the wall of esophagus 24, protrusions 156A and 156B may facilitate electrode 154 providing neurostimulation to the vagus nerve of patient 14 at a location closer to the vagus nerve than when merely touching the wall of esophagus 24. In some examples, protrusions 156A and 156B may be configured to apply pressure to an inner surface of esophagus 24, but not penetrate the mucosa or esophageal wall inner surface of esophagus 24. In such a case, electrode 154 may be referred to as a non-penetrating electrode.

FIGS. 15A and 15B are conceptual diagrams illustrating a top view and side view, respectively, of another example electrode 164 according to the techniques of this disclosure. In FIG. 15A, the top view of electrode 164 is shown as being oval shaped, but may be of any shape. In FIG. 15B, the side view of electrode 164 is shown as being non-planar, such as curved in shape. For example, electrode 164 may be configured to conform to a shape of an expandable member, such as expandable members 32 (FIGS. 2-3), 39 (FIG. 3) or 42 (FIG. 4), to a shape of an internal wall of esophagus 24, or, in the event electrode 164 represents external electrode 46, to a shape of a body of patient 14. Electrode 164 may be an example of any of electrodes 34 (FIGS. 2-3), electrodes 38 (FIG. 3) electrode 40 (FIG. 4), external electrode 46 (FIG. 4), electrodes of transesophageal neurostimulation device 62 (FIG. 7), proximal electrodes 223 or distal electrodes 226 (FIGS. 8A-8C), one or more electrodes 248 (FIGS. 9A-9C), one or more electrodes 268 (FIGS. 10A-10C), one or more electrodes 288 (FIGS. 11A-11C), or other electrodes of this disclosure.

While electrode 164 is shown as being curved in shape, electrode 164 may alternatively be flat or of a different shape.

Electrode 164 includes one or more protrusions, such as protrusion 166A and protrusion 166B extending from a surface 168 of electrode 164. Protrusions 166A and 166B may be configured to puncture or pierce a wall of esophagus 24. By puncturing the wall of esophagus 24, protrusions 166A and 166B may facilitate electrode 164 providing neurostimulation to the vagus nerve of patient 14 at a location closer to the vagus nerve than when merely touching the wall of esophagus 24. Additionally, by puncturing the wall of esophagus 24, protrusions 166A and 166B may be configured to attach to the wall of esophagus 24, such as when electrode 164 is an electrode of transesophageal neurostimulation device 62. In some examples, protrusions 166A and 166B may be configured to puncture through the wall of esophagus 24. In other examples, protrusions 166A and 166B may be configured to partially puncture the wall of esophagus 24.

While specific shapes of electrodes are discussed with respect to FIGS. 12A-15B, in some examples, electrodes discussed herein may shaped and/or sized based on an anatomy of an esophagus, such as esophagus 24. For example, electrodes discussed herein may be shaped and/or sized to make contact with the esophageal wall when providing stimulation.

Figures 16A, 16B, 16C, 16D:
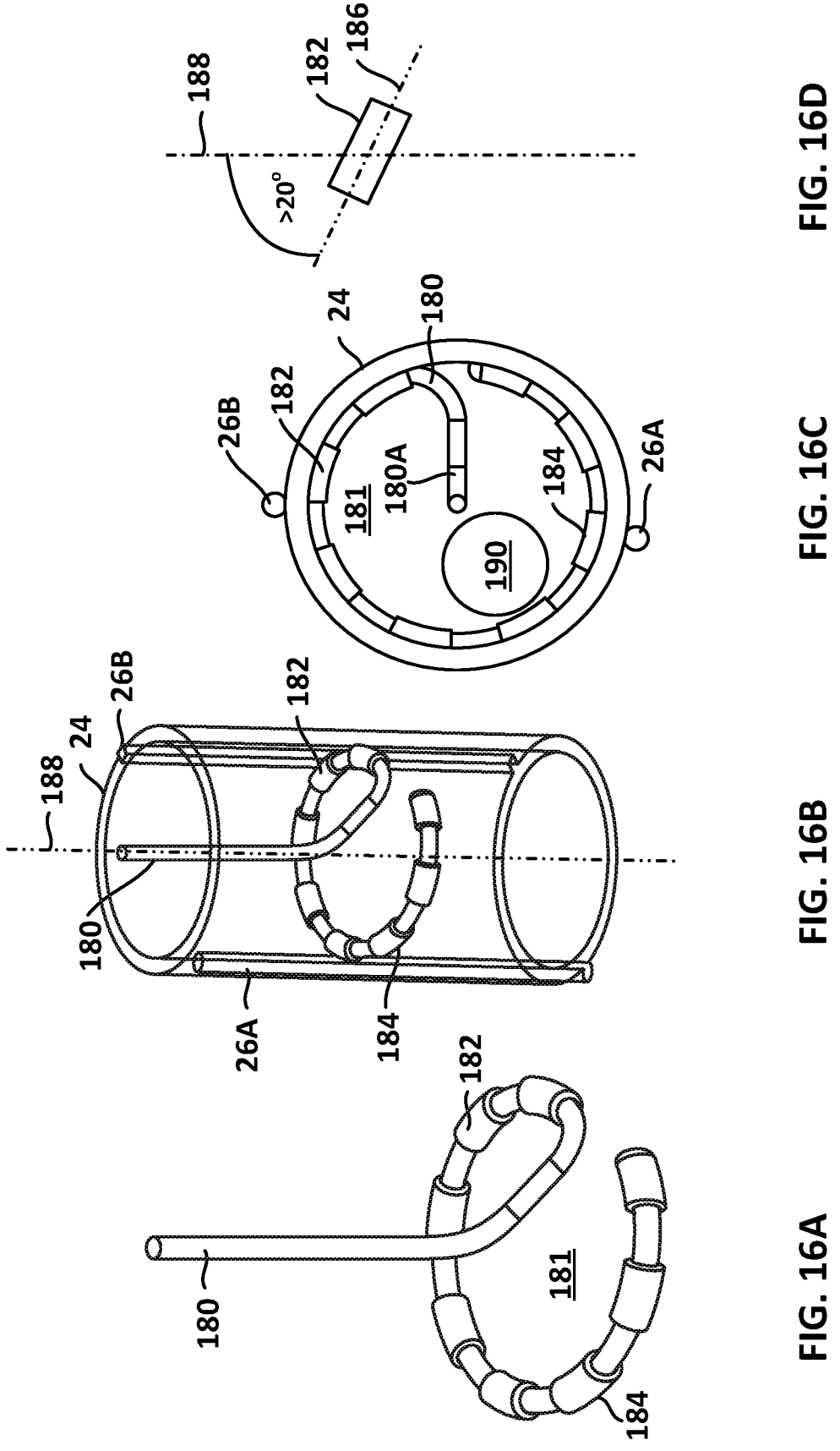
FIGS. 16A-16D are conceptual diagrams of a transesophageal neurostimulation lead which may be coupled to a controller to deliver transesophageal neurostimulation.

FIGS. 16A-16D are conceptual diagrams of a transesophageal neurostimulation lead which may be coupled to a controller to deliver transesophageal neurostimulation. In the example of FIGS. 16A-16D rather than including elongated member 30 (FIGS. 2-4 and 6), a transesophageal neurostimulation system may include one or more leads such as lead 180. FIG. 16A is a side view of lead 180. At least a distal portion of lead 180 may be configured in a generally helix shape around a central longitudinal axis. In this manner, distal portion of lead 180 may form a noncontinuous loop or an open loop. By configuring lead 180 in a generally helix shape around a central longitudinal axis, space 181 is created which may facilitate the insertion of a nasogastric tube into patient 14 when lead 180 is being used for transesophageal neurostimulation, while minimizing a risk of entangling the nasogastric tube with lead 180. A lead or other transesophageal neurostimulation device having a continuous loop, closed loop, or portion that may extend away from a main body of the device while being coupled to the device at both ends of the extended portion may be more susceptible to entanglement with a nasogastric tube than lead 180. Space 181 may also facilitate patient 14 swallowing when lead 180 is at least partially inserted into esophagus 24.

Lead 180 may include a plurality of electrodes, such as electrode 182. In some examples, electrode 182 may be a cylindrically shaped electrode and have a diameter larger than a diameter of lead 180, which may facilitate better contact with the inner sidewall of esophagus 24. A proximal end of lead 180 (not shown for simplicity purposes) may be configured to be connected to controller 28 (FIGS. 2-4), such that controller 28 may generate and deliver stimulation through one or more electrodes of lead 180 (e.g., electrode 182 and/or electrode 184). For example, lead 180 may include conductors electrically coupling the electrodes of lead 180 to controller 28. In some examples, there may be one conductor for each electrode of lead 180. In other examples, at least one conductor of lead 180 may be electrically coupled to more than one electrode of lead 180. While lead 180 is shown as a single helix, in some examples, lead 180 may include more than one helix (e.g., a dual helix).

FIG. 16B depicts a side view of lead 180 inserted into esophagus 24, as well as anterior branch 26A of the vagus nerve and posterior branch 26B of the vagus nerve. The helix shape of the distal portion of lead 180 may enable the electrodes of lead 180 (e.g., electrode 182) to be positioned generally against the inner wall of esophagus 24. For example, the diameter of the helix may be approximately equal to the inner diameter of esophagus 24. As mentioned above, the use of such a helix shaped lead may facilitate the insertion of nasogastric tubes into esophagus 24 and reduce or avoid the risk that the insertion of a nasogastric tube into esophagus 24 would entangle the nasogastric tube with lead 180. FIG. 16B also depicts a longitudinal axis 188 which may represent longitudinal axis 50 (FIG. 5) of esophagus 24 or a central longitudinal axis of lead 180.

FIG. 16C depicts a cross-section of esophagus 24 with lead 180 inserted therein. As seen in FIG. 16C, electrode 182 is positioned near posterior branch 26B of the vagus nerve and may be used to deliver stimulation to posterior branch 26B, while electrode 184 is positioned near anterior branch 26A of the vagus nerve and may be used to deliver stimulation to anterior branch 26A. While portion 180A of lead 180 proximal to the electrodes is depicted as generally coming up the middle of esophagus 24, in some examples, portion 180A may be located elsewhere in esophagus 24, such as against an inner sidewall of esophagus 24. Nasogastric tube 190 may also be inserted into esophagus 24 due to space 181.

FIG. 16D depicts a relationship between an axis of an electrode of lead 180 and an axis of esophagus 24 when lead 180 is inserted into esophagus 24 or a longitudinal axis of lead 180. Electrode 182 has a longitudinal axis 186. In the example of FIG. 16D, longitudinal axis 182 is greater than 20 degrees from longitudinal axis 188 which may represent longitudinal axis 50 (FIG. 5) of esophagus 24 or a longitudinal axis of lead 180. In some examples, each electrode of lead 180 has a longitudinal axis that is greater than 20 degrees from longitudinal axis 188.

Figures 17A, 17B, 17C:
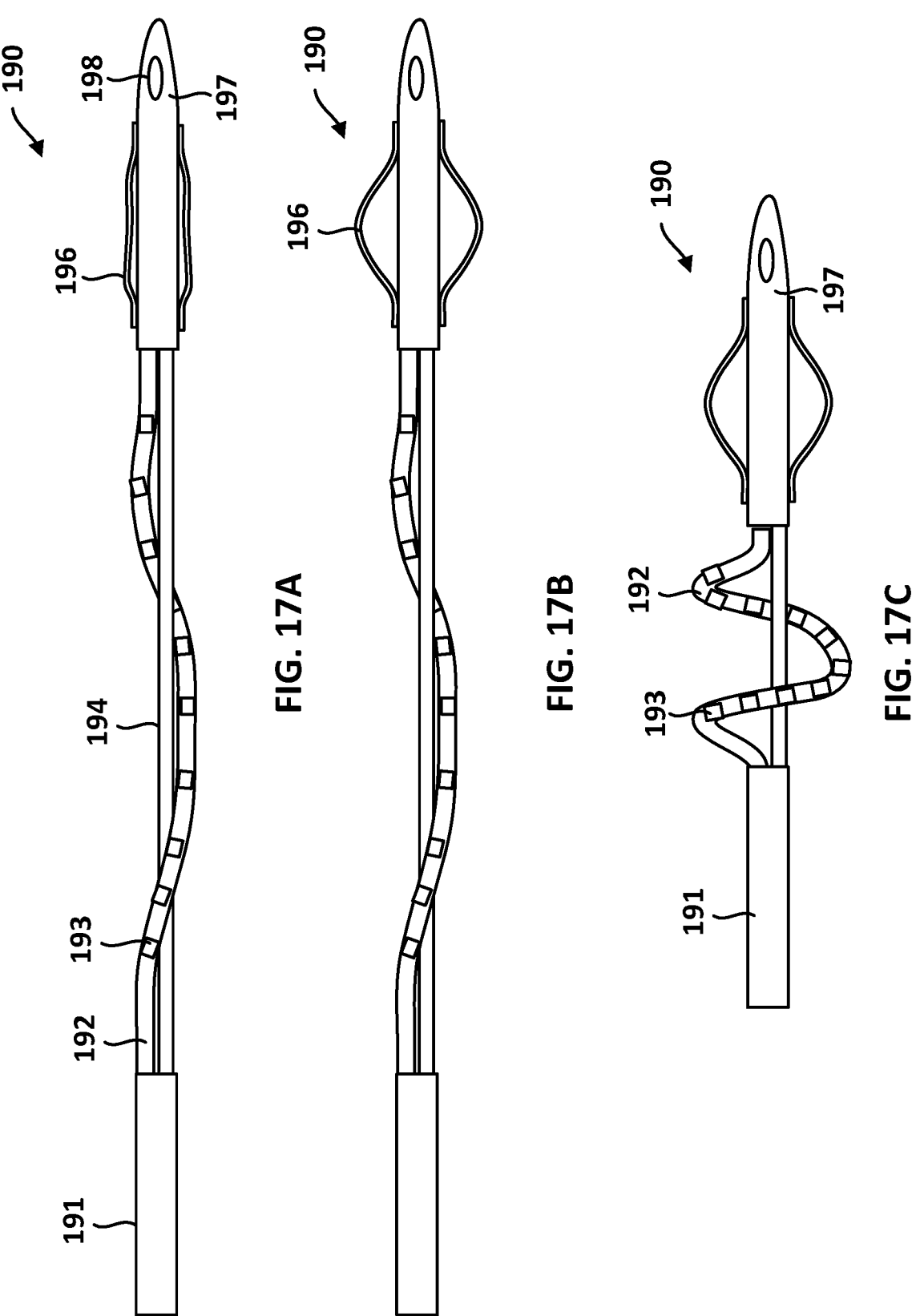
FIGS. 17A-C are conceptual diagrams illustrating three views of a respective portion of another example transesophageal neurostimulation system according to the techniques of this disclosure.

FIGS. 17A-C are conceptual diagrams illustrating three views of a respective portion of another example transesophageal neurostimulation system according to the techniques of this disclosure. FIG. 17A depicts transesophageal neurostimulation system 190 in an unexpanded state. Transesophageal neurostimulation system 190 includes expandable member 196, which is shown as a balloon, but may be any type of expandable member. Transesophageal neurostimulation system 190 also includes a proximal portion 191 and distal portion 197. Distal portion 197 includes an opening 198 fluidically coupled to a lumen in section 194. A proximal end of section 194 may include an opening (not shown) which may be accessible to a clinician. The proximal opening and opening 198 may be used by a clinician to inject a substance into patient 14 or to sample tissue or a substance from patient 14. Transesophageal neurostimulation system 190 also includes lead 192 which may be configured to spiral around section 194. Lead 192 may include a plurality of electrodes, such as electrode 193. The plurality of electrodes may be configured to deliver electrical stimulation to patient 14.

Section 194 may also include a lumen fluidically coupled to expandable member 196. This lumen may be configured to transport a liquid or gas which may be used to expand expandable member 196. Expandable member 196 may be located in stomach 21 of patient 14 when transesophageal neurostimulation system 190 is in use and may be expanded to anchor transesophageal neurostimulation system 190 to patient 14. FIG. 17B shows expandable member 196 in an expanded state.

Once expandable member 196 is expanded, anchoring transesophageal neurostimulation system 190 to patient 14, a clinician may move proximal portion 191 in a distal direction. Such movement may cause proximal portion 191 to move toward distal portion 197. By moving proximal portion 191 towards distal portion 197, lead 192 may move outward, away from section 194 which may cause the electrodes of lead 192 (e.g., electrode 193) to move closer to or to contact the inner wall of esophagus 24, thereby facilitating stimulation of the vagus nerve.

Figure 18A:
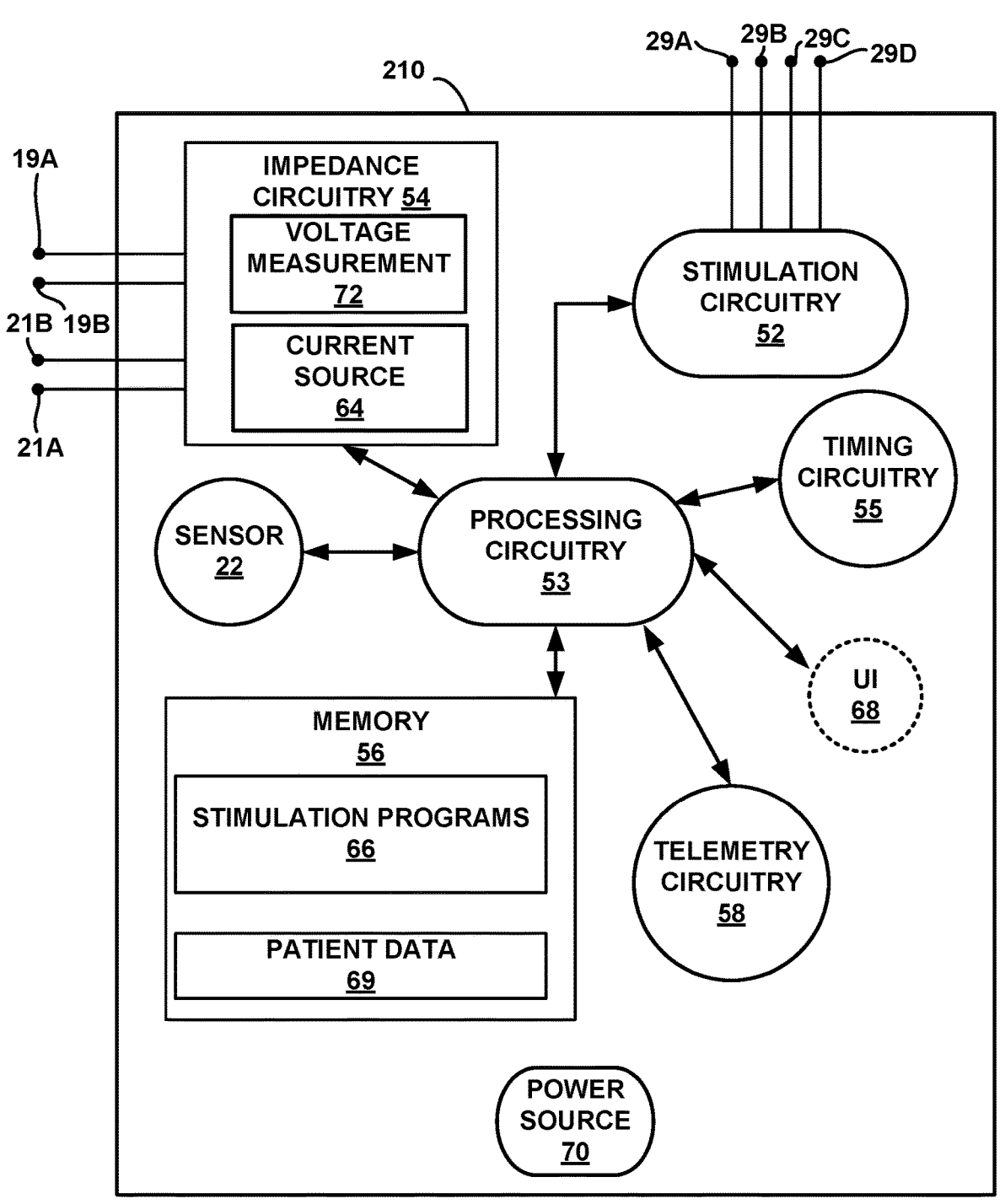
FIGS. 18A-18C are block diagrams of example transesophageal neurostimulation systems that may be configured to perform techniques of this disclosure.
Figure 18B:
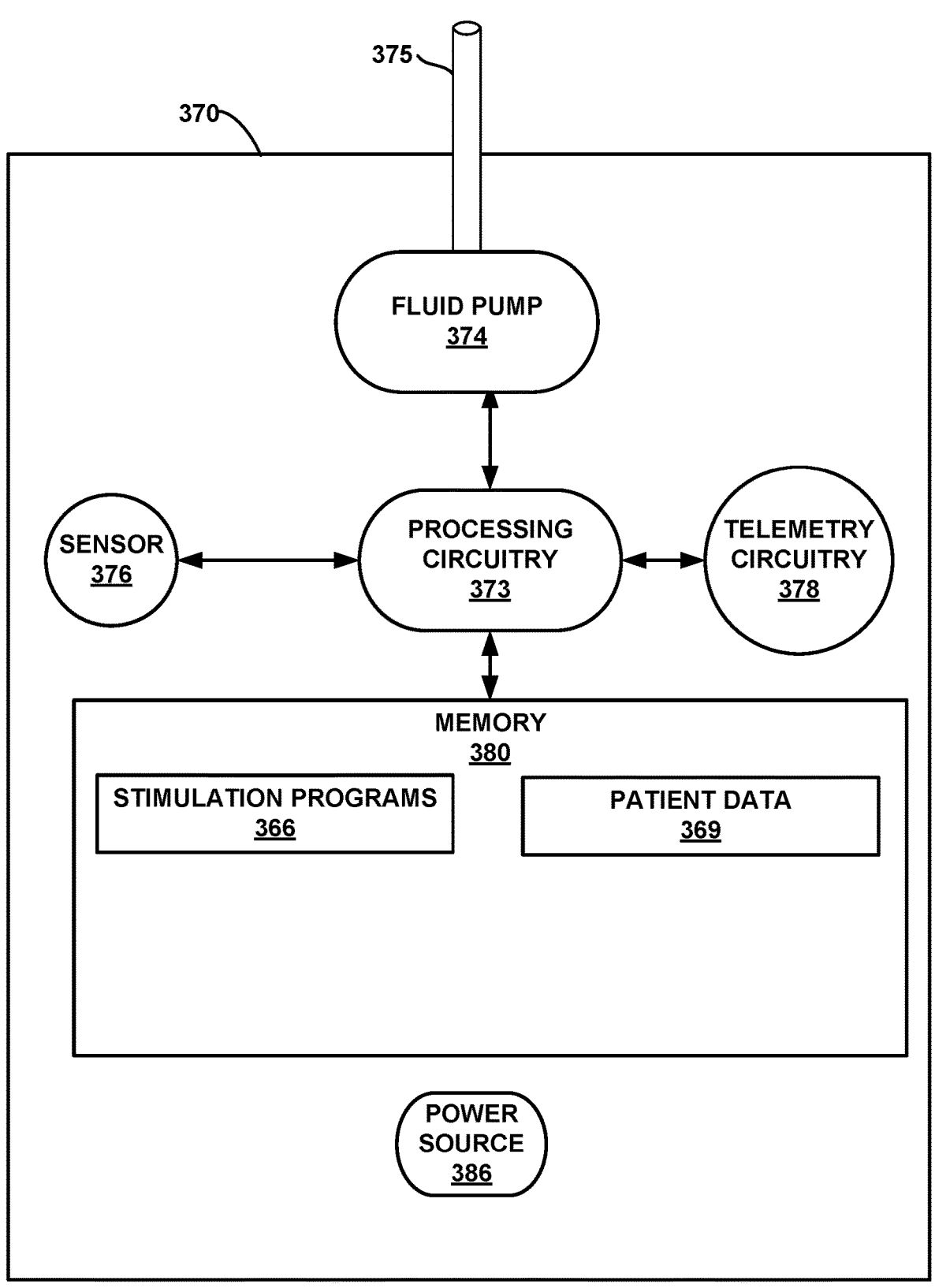
Figure 18C:
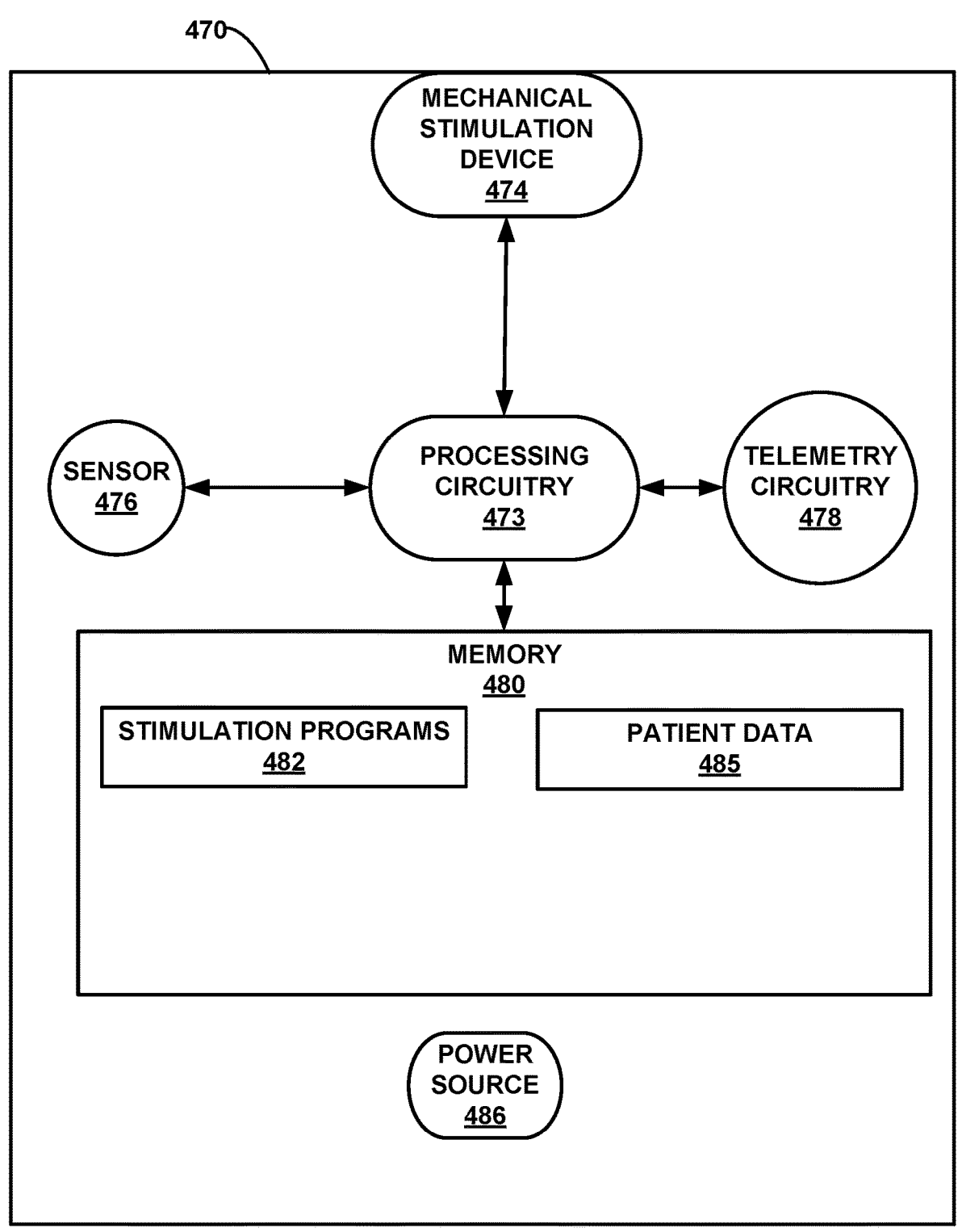

FIGS. 18A-18C are block diagrams of example transesophageal neurostimulation systems that may be configured to perform techniques of this disclosure. In some examples, each of the transesophageal neurostimulation systems of FIGS. 18A-18C may be one device, such as transesophageal neurostimulation device 62 of FIG. 7. In other examples, each of the transesophageal neurostimulation systems of FIGS. 18A-18C may represent more than one device or a collection of devices, such as transesophageal neurostimulation system 10A (FIG. 2) or 10B (FIG. 3).

In the example of FIG. 18A, transesophageal neurostimulation system 210 may include stimulation circuitry 52 configured to generate a stimulation signal, processing circuitry 53, telemetry circuitry 58, timing circuitry 55, memory 56, sensor 22 (which may be an example of sensor 6 (FIGS. 2-3), sensor 4 (FIG. 3), sensor 8 (FIG. 2-3), and impedance circuitry 54. Transesophageal neurostimulation system 210 may also include one or more electrodes, such as electrodes 29A-29D (collectively referred to hereinafter as electrodes 29), electrodes 19A-19B, and electrodes 21A-21B. Electrodes 29, 19A-19B, and 21A-21B, may be examples of electrodes 34 (FIGS. 2-3), electrode 40 (FIG. 4), external electrode 46 (FIG. 4), electrodes of transesophageal neurostimulation device 62 (FIG. 7), electrode 134 (FIGS. 12A-12B), electrode 144 (FIGS. 13A-13B), electrode 154 (FIGS. 14A-14B), electrode 164 (FIGS. 15A-15B), electrode 182 or electrode 184 (FIGS. 16A-16D) or electrode 193 (FIGS. 17A-17C). In some examples, transesophageal neurostimulation system 210 may also include a user interface (UI 68) which may function similarly to user interface 94 of FIG. 19 described in more detail in the discussion of FIG. 19 below.

Sensor 22 may comprise a patient motion sensor that generates a signal indicative of patient posture state, orientation, or activity level. In some examples, transesophageal neurostimulation system 210 may use sensor 22 (which may include an accelerometer) to identify posture states of patient 14. Processing circuitry 53 may use the posture state to determine a position of one or more electrodes 29 and may use the position to determine which electrode combination or other stimulation parameters to use for stimulation. For example, stimulation programs 66 may include predetermined programs for supine, prone, lateral, or other common surgical positions. By knowing the surgical position, the likely position of the vagus branches on patient 14, and the orientation of the electrodes of transesophageal neurostimulation system 210, processing circuitry 53 may automatically select the electrodes to be used for stimulation. Transesophageal neurostimulation system 210 may also operate in a closed-loop manner by controlling stimulation parameters and the delivery of stimulation is response to sensed physiologic parameters such as heart rate, heart rate variability, respiration rate, vagus nerve sensed activity, temperature, EMG, activity level of patient 14, or other measures. These physiological parameters may be sensed by sensor 22 and/or impedance circuitry 54. For example, processing circuitry 53 may control stimulation circuitry 52 to titrate and optimize the neurostimulation therapy based on the sensed physiological parameters.

In some examples, the neurostimulation could be delivered to the vagus nerve (in neck, chest, or abdomen). While the target tissue for the delivery of stimulation is primarily discussed herein as being the vagus nerve, other potential locations of interest may include the sacral nerve, the pudendal nerve, the splenic nerve, the splanchnic nerve, tibial nerve, or other peripheral nerves.

In some examples, the physiological parameters may be sensed by external devices, such as pulse oximetry sensors, Near Infrared Spectroscopy (NIRS), Bispectral Index processed electroencephalogram (EEG), EMG electrodes, EEG electrodes, wearable activity tracker, cameras, depth-sensing cameras, or other sensors. In some examples, physiological parameters may be measured by anesthesia equipment such as a multi-parameter monitor (MPM) or respirator. In some examples, the physiological parameters may be sensed by an implantable sensor such as in a pacemaker or cardiac monitor. By using sensed physiological parameters to control the stimulation, processing circuitry 53 may maximize, optimize, or otherwise improve the stimulation of the cholinergic anti-inflammatory pathway (CAP). CAP has been shown to reduce excessive inflammation and would be useful for treating a variety of illness including, but not limited to: surgical or non-surgical acute kidney injury, postoperative ileus, postoperative cognitive decline or Postoperative delirium; asthma; sepsis; bleeding control; myocardial infarction reduction; dysmotility and obesity. Treating any of these diseases may improve patient outcomes by shortening hospital length of stays and reducing costs.

According to some examples, processing circuitry 53 identifies changes to the patient's physiological state that are relevant to desired changes in neurostimulation. For example, processing circuitry 53 may control stimulation circuitry 52 to generate a stimulation signal that is gated to the respiratory cycle or heartbeat. Vagus nerve stimulation may be more effective when gated to certain physiological activities. For example, it may enhance the potency of the vagus nerve stimulation if the stimulation is gated to be during a phase of respiration, such as the exhalation phase of respiration. For example, the respiration cycle of patient 14 may be accurately detected with pulse oximetry signal analysis or an accelerometer in the device. In some examples, processing circuitry 53 may use other physiologic activities to gate the stimulation. For example, processing circuitry 53 may determine heart rate or circadian rhythms and gate the stimulation signal based on the heart rate, phase of a cardiac cycle, or a phase of a circadian rhythm.

Monitoring other physiological parameters may also serve to enhance safety. For example, stimulating the cervical vagus may depress the heart rate of patient 14. Processing circuitry 53 may be configured to control stimulation circuitry 52 to stop stimulation or lower a stimulation intensity if the heart declined below a threshold. Similarly, processing circuitry 53 may monitor sensed vital signs to monitor pain in an unconscious person. Processing circuitry 53 may be configured to control stimulation circuitry 52 to stop stimulation or lower a stimulation intensity if processing circuitry 53 determines that increasing pain is not associated with surgery or changes in anesthesia. In some examples, processing circuitry 53 may use one or more of the sensed parameters to balance between a parasympathetic and sympathetic tone in patient 14.

In some examples, transesophageal neurostimulation system 210 may be configured to stimulate muscles or motor neurons and to determine an upper limit of stimulation amplitude through one or more feedback techniques, such as a sensed EMG. Other potential feedback techniques which transesophageal neurostimulation system 210 may employ include sensed resulting evoked compound action potential (ECAP) for each stimulation, an accelerometer signal indicative of whether muscular movement is occurring, or patient reported sensations. For example, transesophageal neurostimulation system 210 may include a device, such as a hand held device, which patient 14 may provide, through a user interface, an indication of a sensory threshold or discomfort threshold for various electrode combinations.

For example, transesophageal neurostimulation system 210 may sense the EMG through any of electrodes 29. In some examples, the electrodes sensing the EMG may be the same electrodes or different electrodes than those providing the stimulation. In some examples, muscular activation may be detected mechanically via an accelerometer or pressure sensor.

For example, processing circuitry 53 may be configured to determine a respective upper limit of stimulation amplitude prior muscular activity being detected for each possible combination of electrodes 29. For example, an EMG signal may be indicative of a stimulation amplitude approaching an amplitude at which muscular activity in response to the stimulation may occur. Such information may be used to determine a respective maximum stimulation amplitude for each combination of electrodes 29 that does not stimulate muscular activity, as that stimulating muscular activity may be uncomfortable to patient 14 or may cause undesired movement of transesophageal neurostimulation system 210.

Alternatively, or additionally, processing circuitry 53 may be configured to determine a respective upper limit of stimulation amplitude based on patient input. For example, a clinician may adjust a stimulation amplitude upward from a relatively low amplitude or zero amplitude (e.g., via controller 28) until patient 14 indicates to the clinician or via controller 28 that the stimulation is painful, uncomfortable, perceived, or paresthesia is reached. In the event that patient 14 provides the indication to the clinician, the clinician may in turn enter an indication via controller 28. Processing circuitry 53 may then set the respective maximum stimulation amplitude at or below the stimulation amplitude that was being used when the patient provided the indication.

Processing circuitry 53 may store such maximum stimulation amplitudes associated with each possible combination of electrodes 29 in patient data 69 and use such maximum stimulation amplitudes to limit the amplitude of stimulation such that the stimulation does not cause muscular activity of patient 14, or pain or discomfort to patient 14.

In some examples, processing circuitry 53 may monitor for a resulting ECAP for each stimulation. Once the maximum stimulation amplitude without stimulating undesirable muscular activity has been determined, processing circuitry 53 may determine the more ideal electrodes and amplitude(s) for each electrode combination for a given position of transesophageal neurostimulation system 210, for example, based on the ECAPs, the EMG, the accelerometer signal, and/or patient reported sensations. This technique may be repeated if movement of transesophageal neurostimulation system 210 is detected, at regular time intervals, or on demand, via UI 68, controller 28, or external device 60. For example, processing circuitry 53 may determine the more ideal electrode combination as the electrode combination having the highest ECAP, or the highest maximum stimulation amplitude without eliciting muscular activity.

In general, transesophageal neurostimulation system 210 may comprise any suitable arrangement of hardware, alone or in combination with software and/or firmware, to perform the techniques attributed to transesophageal neurostimulation system 210 and processing circuitry 53, stimulation circuitry 52, impedance circuitry 54, and telemetry circuitry 58 of transesophageal neurostimulation system 210. In various examples, transesophageal neurostimulation system 210 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. Transesophageal neurostimulation system 210 also, in various examples, may include a memory 56, such as random access memory (RAM), read only memory (ROM), programmable read only memory (PROM), erasable programmable read only memory (EPROM), electronically erasable programmable read only memory (EE-PROM), flash memory, comprising executable instructions for causing the one or more processors to perform the actions attributed to them. Moreover, although processing circuitry 53, stimulation circuitry 52, impedance circuitry 54, and telemetry circuitry 58 are described as separate circuitry, in some examples, processing circuitry 53, stimulation circuitry 52, impedance circuitry 54, and telemetry circuitry 58 are functionally integrated. In some examples, processing circuitry 53, stimulation circuitry 52, impedance circuitry 54, and telemetry circuitry 58 correspond to individual hardware units, such as microprocessors, ASICs, DSPs, FPGAs, or other hardware units. In further examples, any of processing circuitry 53, stimulation circuitry 52, impedance circuitry 54, and telemetry circuitry 58 may correspond to multiple individual hardware units such as microprocessors, ASICs, DSPs, FPGAs, or other hardware units.

Memory 56 stores stimulation programs 66 that specify stimulation parameter values for the electrical stimulation provided by transesophageal neurostimulation system 210. Stimulation programs 66 may also store information relating to determining and using physiological parameters, such as threshold values. In some examples, transesophageal neurostimulation system 210 may deliver stimulation therapy based on one or more physiological markers. In other examples, transesophageal neurostimulation system 210 may deliver stimulation therapy that is not based on one or more physiological markers. In some examples, memory 56 also stores patient data 69 which may include sensed physiological parameters. Patient data 69 may also include timing information which may be associated with the sensed physiological parameters.

Generally, stimulation circuitry 52 generates and delivers electrical stimulation under the control of processing circuitry 53. In some examples, processing circuitry 53 controls stimulation circuitry 52 by accessing memory 56 to selectively access and load at least one of stimulation programs 66 to stimulation circuitry 52. For example, in operation, processing circuitry 53 may access memory 56 to load one of stimulation programs 66 to stimulation circuitry 52. In other examples, stimulation circuitry 52 may access memory 56 and load one of the stimulation programs 66. In some examples, the electrical stimulation signal generated and delivered by stimulation circuitry 52 may be above around 10 Hz to avoid activating muscular contraction.

In some examples, stimulation programs 66 may include stimulation programs that are configured to facilitate different effects. For example, stimulation circuitry may use different stimulation programs to generate different electrical stimulation signals to cause different effects. In some examples, stimulation circuitry 52 may generate an electrical stimulation signal in the range of about 1 to 200 Hz to reduce inflammation in patient 14 (e.g., around 20 Hz) or generate an electrical stimulation signal in the range of about 1 kHz to about 50 kHz to block and increase an inflammatory response (e.g., between about 10 kHz to about 20 kHz).

By way of example, processing circuitry 53 may access memory 56 to load one of stimulation programs 66 to stimulation circuitry 52 for delivering the electrical stimulation to patient 14. A clinician or patient 14 may select a particular one of stimulation programs 66 from a list using a programming device, such as external device 60 (FIG. 7) or controller 28 (FIGS. 2-4). Processing circuitry 53 may receive the selection via telemetry circuitry 58. Stimulation circuitry 52 delivers the electrical stimulation to patient 14 according to the selected program for an extended period of time, such as minutes, hours, days, or until patient 14 or a clinician manually stops or changes the program.

Stimulation circuitry 52 delivers electrical stimulation according to stimulation parameters. In some examples, stimulation circuitry 52 delivers electrical stimulation in the form of electrical pulses. In such examples, relevant stimulation parameters may include a voltage amplitude, a current amplitude, a pulse rate, a pulse width, a duty cycle, a duty cycle of the stimulation ON/OFF periods, or the combination of electrodes 29 that stimulation circuitry 52 uses to deliver the stimulation signal. In other examples, stimulation circuitry 52 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 29 stimulation circuitry 52 uses to deliver the stimulation signal.

In the example illustrated in FIG. 18A, impedance circuitry 54 includes voltage measurement circuitry 72 and current source 64, and may include an oscillator (not shown) or the like for producing an alternating signal. In some examples, impedance circuitry 54 may use a four-wire, or Kelvin, arrangement. As an example, processing circuitry 53 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy the vagus nerve, e.g., sub-threshold signals, due to, for example, the amplitudes or widths of such signals and/or the timing of delivery of such signals. Impedance circuitry 54 may also include a switching circuitry (not shown) for selectively coupling electrodes 19A, 19B, 21A, and 21B to current source 64 and voltage measurement circuitry 72. Voltage measurement circuitry 72 may measure the voltage between electrodes 19B and 21B. Voltage measurement circuitry 72 may include sample and hold circuitry or other suitable circuitry for measuring voltage amplitudes. Processing circuitry 53 may determine an impedance value from the measure voltage values received from voltage measurement circuitry 72.

In some examples, processing circuitry 53 may control stimulation circuitry 52 to deliver or terminate the electrical stimulation based on patient or clinician input received via telemetry circuitry 58. Telemetry circuitry 58 includes any suitable hardware, firmware, software or any combination thereof for communicating with another device, such as external device 60 (FIG. 7) or another device external to transesophageal neurostimulation system 210. Under the control of processing circuitry 53, telemetry circuitry 58 may receive communications, e.g., patient or clinician input, from and send communications, e.g., an alert, to external device 60. In the example, where transesophageal neurostimulation system 210 is representative of transesophageal neurostimulation system 10C, external device 60 may use an antenna (not shown) when communicating, which may be internal and/or external. Processing circuitry 53 may provide the data to be sent to external device 60 and the control signals for the telemetry circuit within telemetry circuitry 58, and receive data from telemetry circuitry 58.

Generally, processing circuitry 53 may control telemetry circuitry 58 to exchange information with external device 60 or another device external to transesophageal neurostimulation system 210 wirelessly or wired. Processing circuitry 53 may transmit operational information and patient data 69 and receive stimulation programs or stimulation parameter adjustments via telemetry circuitry 58. Also, in some examples, transesophageal neurostimulation system 210 may communicate with other devices, such as stimulators, control devices, or sensors, via telemetry circuitry 58.

In some examples, power source 70 delivers operating power to the components of transesophageal neurostimulation system 210. In some examples, power source 70 may include a battery and a power generation circuit to produce the operating power. In some examples, the battery may be rechargeable to allow extended operation. Recharging may be accomplished through proximal inductive interaction between an external charger and an inductive charging coil within transesophageal neurostimulation system 210. In other examples, an external inductive power supply may transcutaneously power transesophageal neurostimulation system 210 whenever electrical stimulation is to occur. In some examples, power source 70 may be coupled to an external power source, such as an outlet on a hospital wall.

A stimulation program of stimulation programs 66 may define various parameters of the stimulation waveform and electrode configuration which result in a predetermined stimulation intensity being delivered to the targeted vagus nerve. In some examples, the stimulation program defines parameters for at least one of a current or voltage amplitude of the stimulation signal, a frequency or pulse rate of the stimulation, the shape of the stimulation waveform, a duty cycle of the stimulation, a pulse width of the stimulation, a duty cycle of the stimulation ON/OFF periods, and/or the combination of electrodes 34 and respective polarities of the subset of electrodes 34 used to deliver the stimulation. Together, these stimulation parameter values may be used to define the stimulation intensity (also referred to herein as a stimulation intensity level). In some examples, if stimulation pulses are delivered in bursts, a burst duty cycle also may contribute to stimulation intensity. Also, independent of intensity, a particular pulse width and/or pulse rate may be selected from a range suitable for causing the desired therapeutic effect after stimulation is terminated and, optionally, during stimulation. In addition, as described herein, a period during which stimulation is delivered may include on and off periods (e.g., a duty cycle or bursts of pulses) where even the short inter-pulse durations of time when pulses are not delivered are still considered part of the delivery of stimulation. A period during which transesophageal neurostimulation system 210 withholds stimulation delivery is a period in which no stimulation program is active for transesophageal neurostimulation system 210 is not tracking pulse durations or inter-pulse durations that occur as part of the electrical stimulation delivery scheme). In addition to the above stimulation parameters, the stimulation may be defined by other characteristics, such as a time for which stimulation is delivered, a time for which stimulation is terminated, and times during which stimulation is withheld.

As shown in FIG. 18B, transesophageal neurostimulation system 370 is similar to transesophageal neurostimulation system 210 of FIG. 18A, but transesophageal neurostimulation system 370 delivers neurostimulation to patient 14 in the form of chemicals and/or pharmaceuticals instead of electrical stimulation. Transesophageal neurostimulation system 370 includes processing circuitry 373 (e.g., similar to processing circuitry 53 of FIG. 18A), fluid pump 374 coupled to catheter 375, sensor 376 (e.g., a pressure sensor, accelerometer, or other sensor (which may be similar to sensor 22 of FIG. 18A), telemetry circuitry 378 (e.g., similar to telemetry circuitry 58 of FIG. 18A), memory 380 (e.g., similar to memory 56 of FIG. 18A), and power source 386 (e.g., similar to power source 70 of FIG. 18A). Although, in the example of FIG. 18B, transesophageal neurostimulation system 370 does not include impedance circuitry like impedance circuitry 54 in the example of FIG. 18A, this or other circuitry may be provided in some examples.

Fluid pump 374 may include a chemical and/or pharmaceutical reservoir and a chemical and/or pharmaceutical pump that moves the chemical and/or pharmaceutical from the reservoir, through catheter 375, and out to patient 14. In some examples, fluid pump 374 may move a chemical and/or pharmaceutical from a reservoir external to transesophageal neurostimulation system 370. In some examples, transesophageal neurostimulation system 370 may include both a chemical and/or pharmaceutical reservoir, pump, and electrical stimulation generator. Memory 380 may include stimulation programs 382 and patient data 369. Stimulation programs 382 may include instructions for chemical and/or pharmaceutical delivery. In some examples, such instructions may cause the delivery of stimulation in a closed-loop manner such that delivery of stimulation is based on physiological parameters of patient 14. Patient data 369 may include sensed physiological parameters of the patient or the like. Processing circuitry 373 may control fluid pump 374 to deliver a bolus of one or more chemicals and/or one or more pharmaceuticals to patient 14 based on a stimulation program of stimulation programs 366.

As shown in FIG. 18C, transesophageal neurostimulation system 470 is similar to transesophageal neurostimulation system 210 of FIG. 18A, but transesophageal neurostimulation system 470 delivers neurostimulation to patient 14 mechanically, e.g., in the form of low frequency mechanical stimulation (e.g., vibration) and/or in the form of high frequency mechanical stimulation (e.g., ultrasound). Transesophageal neurostimulation system 470 includes processing circuitry 473 (e.g., similar to processing circuitry 53 of FIG. 18A), mechanical stimulation device 474, sensor 476 (e.g., a pressure sensor, accelerometer, or other sensor (which may be similar to sensor 22 of FIG. 18A), telemetry circuitry 478 (e.g., similar to telemetry circuitry 58 of FIG. 18A), memory 480 (e.g., similar to memory 56 of FIG. 18A), and power source 486 (e.g., similar to power source 70 of FIG. 18A). Although, in the example of FIG. 18C, transesophageal neurostimulation system 470 does not include impedance circuitry like impedance circuitry 54 in the example of FIG. 18A, this or other circuitry may be provided in some examples.

Mechanical stimulation device 474 may include a device configured to deliver mechanical stimulation to patient 14 at a relatively low frequency, such as a haptic device, and/or a device configured to deliver mechanical stimulation to patient 14 at a relatively high frequency, such as an ultrasound emitter. In some examples, mechanical stimulation device 474 may deliver mechanical stimulation via a transducer (not shown) extending from the housing of transesophageal neurostimulation system 470 or from a surface of the housing of transesophageal neurostimulation system 470.

In some examples, transesophageal neurostimulation system 470 may include a low frequency mechanical stimulation device and/or high frequency mechanical stimulation device, as well as a pharmaceutical reservoir, pump, and/or an electrical stimulation generator. Memory 480 may include stimulation programs 482 and patient data 469. Stimulation programs 482 may include instructions for delivery of mechanical. In some examples, such instructions may cause the delivery of stimulation in a closed-loop manner such that delivery of stimulation is based on physiological parameters of patient 14. Patient data 469 may include sensed physiological parameters of the patient or the like. Processing circuitry 473 may control mechanical stimulation device 474 to deliver mechanical stimulation to patient 14 based on a stimulation program of stimulation programs 366.

Figure 19:
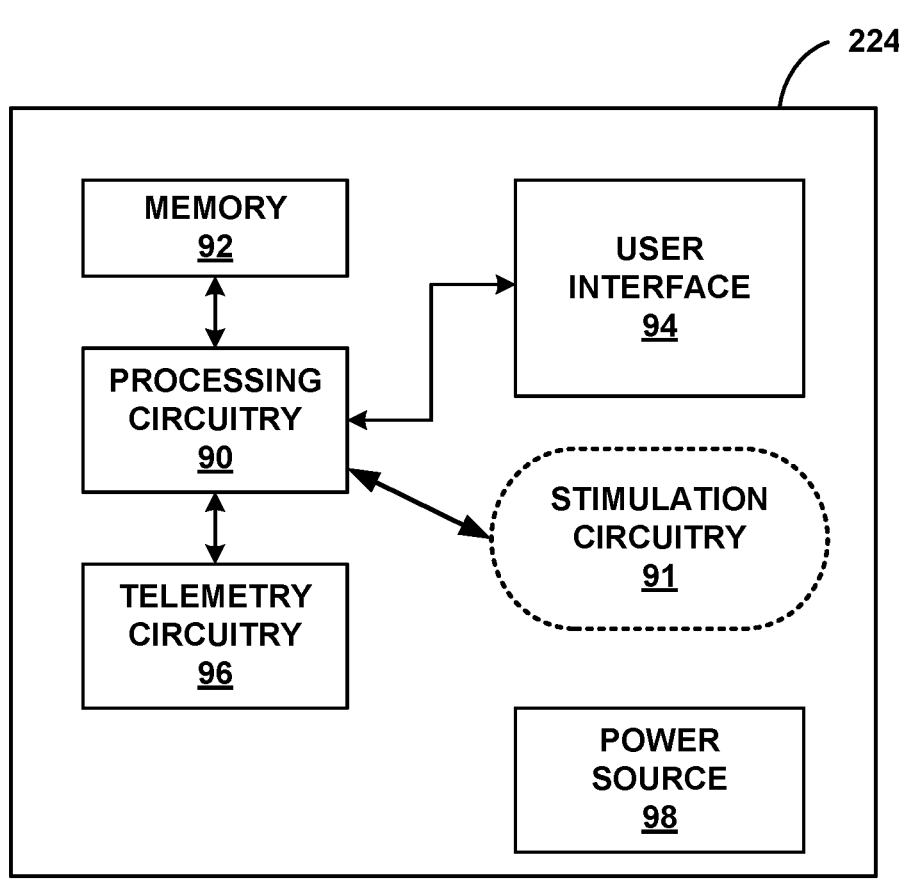
FIG. 19 is a block diagram illustrating an example configuration of a computing device according to the techniques of this disclosure.

FIG. 19 is a block diagram illustrating an example configuration of a computing device. Computing device 224 may be an example of external device 60 or controller 28. Computing device 224 may include notebook computer, a smart phone, a workstation, a key fob, or a wearable device, for example. As illustrated in FIG. 19, computing device 224 may include a processing circuitry 90, memory 92, user interface 94, telemetry circuitry 96, and power source 98. Memory 92 may store program instructions that, when executed by processing circuitry 90, cause processing circuitry 90 and computing device 224 to provide the functionality ascribed to external device 60 or controller 28 throughout this disclosure. In some examples, such as where computing device 224 represents controller 28, computing device 224 may include stimulation circuitry 91 which may function similarly to stimulation circuitry 52 of FIG. 18A. In general, computing device 224 comprises any suitable arrangement of hardware, alone or in combination with software and/or firmware, to perform the techniques attributed to computing device 224, and processing circuitry 90, user interface 94, and telemetry circuitry 96 of computing device 224. In various examples, computing device 224 may include one or more processors, such as one or more microprocessors, DSPs, ASICs, FPGAs, or any other equivalent integrated or discrete logic circuitry, as well as any combinations of such components. Computing device 224 also, in various examples, may include a memory 92, such as RAM, ROM, PROM, EPROM, EEPROM, flash memory, a hard disk, a CD-ROM, comprising executable instructions for causing the one or more processors to perform the actions attributed to them. Moreover, although processing circuitry 90 and telemetry circuitry 96 are described as separate circuitry, in some examples, processing circuitry 90 and telemetry circuitry 96 are functionally integrated. In some examples, processing circuitry 90 and telemetry circuitry 96 and telemetry circuitry 58 correspond to individual hardware units, such as microprocessors, ASICs, DSPs, FPGAs, or other hardware units. In other examples, any of processing circuitry 90 and telemetry circuitry 96 and telemetry circuitry 58 may correspond to multiple individual hardware units, such as microprocessors, ASICs, DSPs, FPGAs, or other hardware units.

Memory 92 may store program instructions that, when executed by processing circuitry 90, cause processing circuitry 90 and computing device 224 to provide the functionality ascribed to computing device 224 throughout this disclosure. In some examples, memory 92 may further include program information, e.g., stimulation programs defining the neurostimulation, similar to those stored in memory 56 of transesophageal neurostimulation system 210. The stimulation programs stored in memory 92 may be downloaded into memory 56 of transesophageal neurostimulation system 210.

In certain examples, computing device 224 includes a user interface 94 that allows the patient to provide input. Patient 14 may, additionally or alternatively, request a change in stimulation program or settings through user interface 94.

User interface 94 may include a button or keypad, lights, a speaker for voice commands, a turnable knob, a display, such as a liquid crystal (LCD), light-emitting diode (LED), or cathode ray tube (CRT). In some examples the display may be a touch screen. As discussed in this disclosure, processing circuitry 90 may present and receive information relating to electrical stimulation and resulting therapeutic effects via user interface 94. For example, processing circuitry 90 may receive patient input via user interface 94. The input may be, for example, in the form of pressing a button on a keypad or selecting an icon from a touch screen.

Processing circuitry 90 may also present information to the patient in the form of alerts related to delivery of the electrical stimulation to patient 14 or a caregiver via user interface 94. Although not shown, computing device 224 may additionally or alternatively include a data or network interface to another computing device, to facilitate communication with the other device, and presentation of information relating to the electrical stimulation and therapeutic effects after termination of the electrical stimulation via the other device.

Telemetry circuitry 96 supports wireless or wired communication between transesophageal neurostimulation system 210 and computing device 224 under the control of processing circuitry 90. Telemetry circuitry 96 may also be configured to communicate with another computing device via wireless communication techniques, or direct communication through a wired connection. In some examples, telemetry circuitry 96 may be substantially similar to telemetry circuitry 58 of transesophageal neurostimulation system 210 described above, providing wireless communication via an RF or proximal inductive medium. In some examples, telemetry circuitry 96 may include an antenna, which may take on a variety of forms, such as an internal or external antenna.

Examples of local wireless communication techniques that may be employed to facilitate communication between computing device 224 and another computing device include RF communication according to the 802.11 or Bluetooth specification sets, infrared communication, e.g., according to the IrDA standard, or other standard or proprietary telemetry protocols. In this manner, other external devices may be capable of communicating with computing device 224 without needing to establish a secure wireless connection.

Power source 98 delivers operating power to the components of computing device 224. Power source 98 may include a battery and a power generation circuit to produce the operating power. In some examples, the battery may be rechargeable to allow extended operation.

Figure 20A:
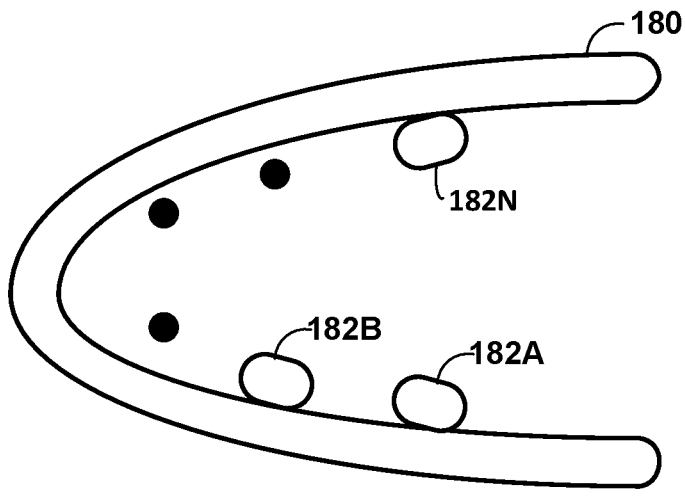
FIGS. 20A and 20B are conceptual diagrams illustrating an example configuration of an expandable member in an unexpanded state and an expanded state, respectively, according to the techniques of this disclosure.
Figure 20B:
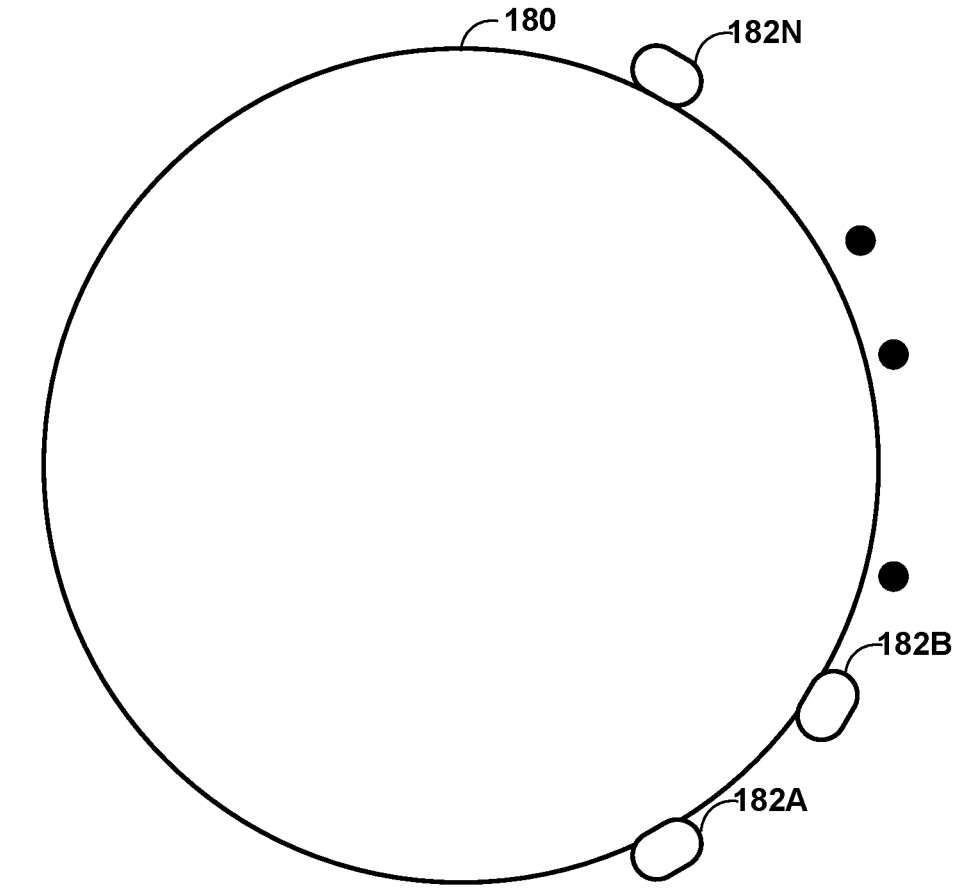

FIGS. 20A and 20B are conceptual diagrams illustrating an example configuration of an expandable member 180 in an unexpanded state and an expanded state, respectively, according to the techniques of this disclosure. In FIGS. 20A-20B, expandable member 180 is depicted having a plurality of electrodes 182A, 182B to 182N (hereinafter electrodes 182). Expandable member 180 may be an example of any of expandable member 32 (FIGS. 2-3), expandable member 39 (FIG. 3), or expandable member 42 (FIG. 4, in which case expandable member 180 may include a single electrode). Electrodes 182 may be an example of electrodes 34 (FIGS. 2-3), electrodes 38 (FIG. 3), electrode 40 (FIG. 4), electrodes 223 and/or 226 (FIGS. 8A-8C), electrodes 248 (FIGS. 9A-9C), electrodes 268 (FIGS. 10A-10C), electrodes 288 (FIGS. 11A-11C), electrode 134 (FIGS. 12A-12B), electrode 144 (FIGS. 13A-13B), electrode 154 (FIGS. 14A-14B), or electrode 164 (FIGS. 15A-15B).

As shown in FIG. 20A, when in an unexpanded state, expandable member 180 may be configured to take a U shape as shown. Electrodes 182 may be disposed on the inner sides of the U shape, while still being on the outer surface of expandable member 180. In this manner when expandable member 180 is inserted into esophagus 24 of patient 14, electrodes 182 may not be in contact with the inner wall of esophagus 24 until expandable member 180 is expanded into an expanded state. This may protect the integrity of electrodes 182 and protect the inner wall of esophagus 24 from being damaged by electrodes 182 during transit to the target location.

As shown in FIG. 19B, when in an expanded state, expandable member 180 may be spherical or another shape which may be configured to place electrodes 182 in contact with the inner wall of esophagus 24.

Figure 21:
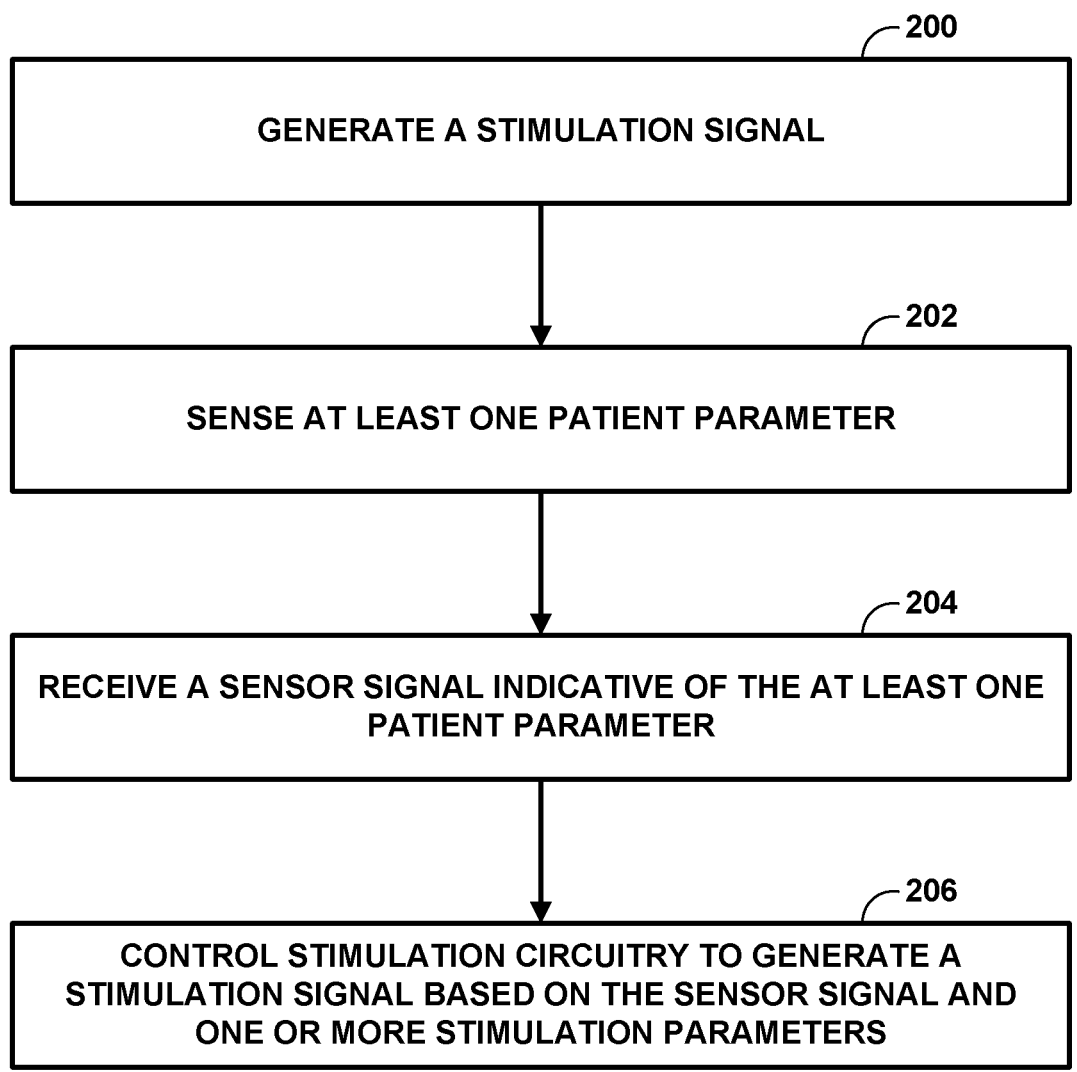
FIG. 21 is a flow diagram illustrating example techniques of the present disclosure.

FIG. 21 is a flow diagram illustrating example techniques according to the present disclosure. While discussed primarily with respect to transesophageal neurostimulation system 210 of FIG. 18A, the techniques of FIG. 21 may be performed by other transesophageal neurostimulation systems. Stimulation circuitry 52 may generate a stimulation signal (200). For example, stimulation circuitry 52 may generate an electrical signal based on stimulation parameters stored in stimulation programs 66 to be used to stimulate the vagus nerve of patient 14 under the control of processing circuitry 53 or processing circuitry 90.

Processing circuitry 53 or processing circuitry 90 may receive a sensor signal indicative of the at least one patient parameter (202). For example, processing circuitry 53 or processing circuitry 90 may receive a signal from sensor 22 and/or impedance circuitry 54 indicative of at least one patient parameter. For example, the at least one patient parameter may include physiological parameters of patient 14, such as an impedance of tissue, a heart rate, a heart rate variability over time, a respiration rate, sensed activity of the vagus nerve, EMG, activity level of patient 14, a temperature, or the like.

Processing circuitry 53 or processing circuitry 90 may control the stimulation circuitry to generate the stimulation signal based on the sensor signal and one or more stimulation parameters (204). For example, if a sensed signal indicates a heart rate or respiration rate of patient 14 is relatively low, processing circuitry 53 or processing circuitry 90 may decrease an intensity of the stimulation signal or cease to generate the stimulation signal.

In some examples, transesophageal neurostimulation system 210 includes a detachable neurostimulation device (e.g., transesophageal neurostimulation device 62 of FIG. 7) configured to be attached to a wall of esophagus 24 without a tether and to detach from the wall of esophagus 24. In some examples, transesophageal neurostimulation system 210 device includes an array of radially divided electrodes (e.g., electrodes 34) configured to deliver the stimulation signal to a target location in a patient in a cycled manner. In some examples, processing circuitry 53 or processing circuitry 90 is further configured to determine locations of anterior branch 26A of the vagus nerve or posterior branch 26B of the vagus nerve (both of FIG. 1) based on impedance sensed by at least one electrode (e.g., electrode 21A or 21B of FIG. 18A). In some examples, the sensor circuitry (e.g., sensor 22 of FIG. 18A) includes an accelerometer configured to sense a posture of the patient, wherein processing circuitry 53 or processing circuitry 90 is configured to control stimulation circuitry 52 based on the posture of the patient. In some examples, the sensor signal is indicative of one or more of a heart rate variability over time or respiration rate. In some examples, processing circuitry 53 or processing circuitry 90 is further configured to control stimulation circuitry 52 to begin a stimulation sequence automatically. In some examples, transesophageal neurostimulation device 62 (FIG. 7) is configured to be inserted sub-mucosally or between layers of longitudinal and circumferential muscles. In some examples, transesophageal neurostimulation system 210 includes detachable controller 28. In some examples, processing circuitry 53 or processing circuitry 90 is further configured to control stimulation circuitry 52 to deliver stimulation at one frequency to one branch of the vagus nerve and at a different frequency to another branch of the vagus nerve.

In some examples, transesophageal neurostimulation system includes a nasogastric device (e.g., elongated member 30 of FIGS. 2-4, 6) defining a lumen (e.g., lumen 80) configured for at least one of injecting substances to or removing the substances from patient 14. In some examples, transesophageal neurostimulation system 210 includes an external electrode (e.g., external electrode 46 of FIG. 4) configured to be deployed on an external skin surface of patient 14. In some examples, transesophageal neurostimulation system 210 includes an expandable member (e.g., expandable member 32 (FIGS. 2-3), expandable member 39 (FIG. 3), or expandable member 42 (FIG. 4) configured to distend esophagus 24 of patient 14.

In some examples, transesophageal neurostimulation system 210 includes an expandable member (e.g., expandable member 36 of FIGS. 2-4) configured to position electrodes at a desired position within the esophagus. In some examples, the expandable member comprises a balloon.

In some examples, transesophageal neurostimulation system 210 includes at least one electrode (e.g., electrodes 29) configured to deliver the stimulation signal to a target tissue within the patient. In some examples, the target tissue is at least one branch of a vagus nerve (e.g., anterior branch 26A of the vagus nerve or posterior branch 26B of the vagus nerve).

In some examples, the array of electrodes (e.g., electrodes 34 of FIGS. 2-3) includes between 2 and 16 electrodes, inclusively. In some examples, the at least one electrode is disposed on an exterior surface of an expandable member (e.g., expandable member 32, expandable member 39, or expandable member 42). In some examples, the at least one electrode includes at least one of a planar electrode (e.g., electrode 134 of FIGS. 12A-12B), a non-planar electrode (e.g., electrode 144 of FIGS. 13A-13B), an indenting electrode comprising at least one protrusion extending from a surface of the indenting electrode, the at least one protrusion being configured to indent a wall of esophagus 24 (e.g., electrode 154 of FIGS. 14A-14B), or a puncturing electrode comprising at least one protrusion extending from a surface of the puncturing electrode, the at least one protrusion being configured to puncture the wall of the esophagus. (e.g., electrode 164 of FIGS. 15A-15B).

In some examples, the sensor signal is a first sensor signal and processing circuitry 53 or processing circuitry 90 is further configured to receive a second sensor signal indicative of one or more of a sensed heart rate, a sensed vagus nerve activity, or a sensed temperature and change, based on the second sensor signal, at least one stimulation parameter that defines the stimulation signal. In some examples, the second sensor signal is received from one of the sensor circuitry (e.g., sensor 22) or a sensor external to the device (e.g., sensor 8).

In some examples, transesophageal neurostimulation system 210 includes a battery (e.g., power source 70 of FIG.

18A) configured to power the device or the system. In some examples, processing circuitry 53 or processing circuitry 90 is configured to determine that at least one of an impedance is below a predetermined threshold or an expandable member (e.g., expandable member 32, expandable member 42, or expandable member 36) has been expanded, and responsive to the determination, control stimulation circuitry 52 to begin generating the stimulation signal.

In some examples, processing circuitry 53 or processing circuitry 90 is further configured to control stimulation circuitry 52 to generate a sub-sensory stimulation signal responsive to determining that patient 14 is conscious and generate a supra-sensory stimulation signal responsive to determining patient 14 is unconscious.

FIG. 22 is a flow diagram illustrating additional example transesophageal neurostimulation techniques. While discussed primarily with respect to transesophageal neurostimulation system 210 of FIG. 18A, the techniques of FIG. 22 may be performed by other transesophageal neurostimulation systems. Stimulation circuitry 52 may generate a transesophageal stimulation signal (500). For example, stimulation circuitry 52 may generate an electrical signal based on stimulation parameters stored in stimulation programs 66 to be used to stimulate the vagus nerve of patient 14 under the control of processing circuitry 53 or processing circuitry 90.

Processing circuitry 53 or processing circuitry 90 may determine a maximum transesophageal stimulation amplitude value that is below a threshold amplitude value (502). For example, processing circuitry 53 or processing circuitry 90 may determine the threshold amplitude value based on at least one of a transesophageal stimulation amplitude that elicits muscular activity in response to delivery of the stimulation signal via a combination of electrodes or patient input in response to delivery of the stimulation signal via the combination of electrodes. For example, processing circuitry 53 or processing circuitry 90 may titrate up, or ramp up, the amplitude of the stimulation signal delivered via one or more electrodes until muscular activity is sensed, for example, through an EMG, ECAP, accelerometer, or another sensor, or until a patient provides input such as the stimulation is painful, uncomfortable, sensed, or paresthesia is reached.

Processing circuitry 53 or 90 may then select the amplitude value of the amplitude used to deliver the last stimulation signal that did not induce detectable muscular activity (e.g., under a threshold amplitude value that defines a stimulation amplitude that does elicit muscular activity). Processing circuitry 53 or 90 may determine this amplitude value just below the threshold amplitude value as the maximum stimulation amplitude for purposes or delivering stimulation. Processing circuitry 53 or processing circuitry 90 may control stimulation circuitry 52 to generate the transesophageal stimulation signal based at least in part on at least one of one or more of the stimulation parameters or the maximum transesophageal stimulation amplitude such that an amplitude of the transesophageal stimulation signal does not exceed the respective maximum transesophageal stimulation amplitude (504). For example, processing circuitry 53 or processing circuitry 90 may control stimulation circuitry 52 such that the amplitude of a stimulation signal does not exceed a respective maximum transesophageal stimulation amplitude for a given combination of stimulation electrodes.

In some examples, processing circuitry 53 or processing circuitry 90 may, prior to controlling stimulation circuitry 52 to generate the transesophageal stimulation signal, determine the combination of electrodes 29. For example, processing circuitry 53 or processing circuitry 90 may determine a respective maximum transesophageal stimulation amplitude value that is below the threshold amplitude value for a plurality of different electrode combinations (e.g., of electrodes 29) based on feedback. The feedback may include at least one of respective electromyogram signals, respective evoked compound action potentials (ECAPs), respective accelerometer signals, or respective patient reported sensations. Processing circuitry 53 or processing circuitry 90 may select, as the combination of electrodes, one of the plurality of different electrode combinations that has at least one of a highest ECAP or a highest respective maximum transesophageal stimulation amplitude value. In some examples, processing circuitry 53 or processing circuitry 90 may repeat the determining of the combination of electrodes in response to determining a device has moved, at a predetermined time interval, or in response to user input.

In some examples, processing circuitry 53 or processing circuitry 90 may determine a posterior direction, and control stimulation circuitry 52 to deliver the transesophageal stimulation signal in the posterior direction. In some examples, the determination of the posterior direction is based on at least one of one or more accelerometer signals, an inclinometer signal, or a signal indicative of an electrocardiogram.

In some examples, processing circuitry 53 or processing circuitry 90 may determine a physiological activity of the patient, and control stimulation circuitry 52 to gate the delivery of the transesophageal stimulation signal based on the physiological activity of the patient. In some examples, the physiological activity includes at least one of a phase of respiration, a heart rate, a phase of the cardiac cycle, or a phase of a circadian rhythm.

In some examples, stomach sensor 7 (FIG. 2) may generate a signal indicative of the stomach sensor being in a stomach of a patient. In some examples, stomach sensor 7 includes at least one of a pressure sensor or a pH sensor.

In some examples, at least a portion of the system (e.g., transesophageal neurostimulation system 210) is configured to be inserted into an esophagus of a patient and wherein the at least the portion of the system comprises at least one of a lubricant or local anesthetic.

The techniques of this disclosure may facilitate the stimulating the cervical, thoracic, or abdominal vagus branches in a manner that is relatively easy and quick to use, such as through transesophageal stimulation. Such techniques may be used for short-term stimulation, such as during an acute health problem, such as surgery or during an abrupt illness, such as sepsis, without having to undertake an invasive surgical procedure to implant a vagus nerve stimulation device.

It should be noted that the techniques described herein, may not be limited to treatment or monitoring of a human patient. In alternative examples, the techniques of this disclosure may be applied to non-human patients, e.g., primates, canines, equines, pigs, and felines. These other animals may undergo clinical or research therapies that my benefit from the subject matter of this disclosure.

Various examples are discussed relative to one or more stimulation devices. It is recognized that the stimulation devices may include features and functionality in addition to electrical stimulation. Many of these additional features are expressly discussed herein. A few example features include, but are not limited to, different types of sensing capabilities and different types of wireless communication capabilities. For ease of discussion, the present disclosure does not expressly recite every conceivable combination of the additional features, such as by repeating every feature each time different examples and uses of the stimulation devices are discussed.

The techniques of this disclosure may be implemented in a wide variety of computing devices, medical devices, or any combination thereof. Any of the described units, circuitry or components may be implemented together or separately as discrete but interoperable logic devices. Depiction of different features as circuitry or units is intended to highlight different functional aspects and does not necessarily imply that such circuitry or units must be realized by separate hardware or software components. Rather, functionality associated with one or more circuitry or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various circuitry and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processing circuitry" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, circuitry or components may be implemented together or separately as discrete but interoperable logic devices. Depiction of different features as circuitry or units is intended to highlight different functional aspects and does not necessarily imply that such circuitry or units must be realized by separate hardware or software components. Rather, functionality associated with one or more circuitry or units may be performed by separate hardware or software components, or integrated within common or separate hardware or software components. For example, any circuitry described herein may include electrical circuitry configured to perform the features attributed to that particular circuitry, such as fixed function processing circuitry, programmable processing circuitry, or combinations thereof.

In some examples, a computer-readable storage medium comprises non-transitory medium. The term "non-transitory" may indicate that the storage medium is not embodied in a carrier wave or a propagated signal. In certain examples, a non-transitory storage medium may store data that may, over time, change (e.g., in RAM or cache).

This disclosure includes the following non-limiting examples.

Example 1A. A system for delivering transesophageal neurostimulation, the system comprising: stimulation circuitry configured to generate a stimulation signal; memory configured to store stimulation parameters that at least partially define the stimulation signal; processing circuitry communicatively coupled to the memory, and the stimulation circuitry, the processing circuitry being configured to: control the stimulation circuitry to generate the stimulation signal based at least in part on one or more of the stimulation parameters; and wherein at least one of: a) the system comprises a detachable neurostimulation device configured to be attached to a wall of an esophagus without a tether and to detach from the wall of the esophagus, b) the system further comprises an array of radially divided electrodes configured to deliver the stimulation signal to a target location in a patient in a cycled manner, c) the processing circuitry is further configured to determine locations of an anterior branch of a vagus nerve or a posterior branch of a vagus nerve based on impedance sensed by at least one electrode, d) the system further comprises sensor circuitry comprising an accelerometer configured to sense a posture of the patient, wherein the processing circuitry is configured to control the stimulation circuitry further based on the posture of the patient, e) the processor circuitry is further configured to receive a sensor signal indicative of one or more of a heart rate variability over time or respiration rate, f) the processing circuitry is further configured to control the stimulation circuitry to begin a stimulation sequence automatically, g) at least a portion of the system is configured to be inserted sub-mucosally or between layers of longitudinal and circumferential muscles, h) the system further comprises a detachable controller, or i) the processing circuitry is further configured to control the stimulation circuitry to deliver stimulation at one frequency to one location of the vagus nerve and at a different frequency to location of the vagus nerve.

Example 2A. The system of example 1A, wherein the system comprises a nasogastric device defining a lumen configured for at least one of injecting substances to or removing the substances from the patient.

Example 3A. The system of example 1A or example 2A, further comprising an external electrode configured to be disposed on an external skin surface of the patient.

Example 4A. The system of any of examples 1A-3A, further comprising an expandable member configured to distend the esophagus of the patient.

Example 5A. The system of any of examples 1A-4A, further comprising an expandable member configured to position electrodes at a desired position within the esophagus.

Example 6A. The system of example 4A or example 5A, wherein the expandable member comprises a balloon.

Example 7A. The system of any of examples 1A-6A, further comprising at least one electrode configured to deliver the stimulation signal to a target tissue within the patient.

Example 8A. The system of example 7A, wherein the target tissue is at least one branch of a vagus nerve.

Example 9A. The system of any of examples 1A-8A, wherein the array of electrodes comprises between 2 and 16 electrodes, inclusively.

Example 10A. The system of any of examples 7A-9A, wherein the at least one electrode is disposed on an exterior surface of an expandable member.

Example 11A. The system of any of examples 7A-10A, wherein the at least one electrode comprises at least one of: a planar electrode; a non-planar electrode; an indenting electrode comprising at least one protrusion extending from a surface of the indenting electrode, the at least one protrusion being configured to indent a wall of the esophagus; or a puncturing electrode comprising at least one protrusion extending from a surface of the puncturing electrode, the at least one protrusion being configured to puncture the wall of the esophagus.

Example 12A. The system of any of examples 1A-11A, wherein the sensor signal is a first sensor signal, and wherein the processing circuitry is further configured to: receive a second sensor signal indicative of one or more of a sensed heart rate, a sensed vagus nerve activity, or a sensed temperature; and change, based on the second sensor signal, at least one stimulation parameter that defines the stimulation signal.

Example 13A. The system of example 12A, wherein the processing circuitry is configured to receive the second sensor signal from one of sensor circuitry of the system or a sensor external to the system.

Example 14A. The system of any of examples 1A-13A, further comprising a battery configured to power at least a portion of the system.

Example 15A. The system of any of examples 1A-14A, wherein the processing circuitry is configured to control the stimulation circuitry to: determine that at least one of an impedance is below a predetermined threshold or an expandable member has been expanded; and responsive to the determination, begin generating the stimulation signal.

Example 16A. The system of any of examples 1A-15A, wherein the processing circuitry is further configured to control the stimulation circuitry to generate a sub-sensory stimulation signal responsive to determining that the patient is conscious and generate a supra-sensory stimulation signal responsive to determining that the patient is unconscious.

Example 17A. The system of any of examples 1A-16A, wherein at least a portion of the system is configured to be implanted within the patient.

Example 18A. A method for delivering transesophageal neurostimulation, the method comprising: generating, by stimulation circuitry, a stimulation signal; controlling, by processing circuitry, the stimulation circuitry to generate the stimulation signal based at least in part on one or more stimulation parameters; and wherein at least one of: a) attaching, by a detachable neurostimulation device, to a wall of an esophagus without a tether and detaching, by the detachable neurostimulation device, from the wall of the esophagus, b) delivering via an array of radially divided electrodes the stimulation signal to a target location in a patient in a cycled manner, c) determining, by the processing circuitry, locations of an anterior branch of a vagus nerve or a posterior branch of a vagus nerve based on impedance sensed by at least one electrode, d) sensing, by an accelerometer of sensor circuitry, a posture of the patient and controlling, by the processing circuitry the stimulation circuitry further based on the posture of the patient, e) receiving, by the processing circuitry, a sensor signal is indicative of one or more of a heart rate variability over time or respiration rate, f) control, by the processing circuitry, the stimulation circuitry to begin a stimulation sequence automatically, g) inserting a neurostimulation device sub-mucosally or between layers of longitudinal and circumferential muscles, h) detaching, by a clinician, a detachable controller, or i) control, by the processing circuitry, the stimulation circuitry to deliver stimulation at one frequency to location of the vagus nerve and at a different frequency to another location of the vagus nerve.

Example 19A. The method of example 18A, further comprising at least one of injecting substances to or removing substances from the patient via a lumen defined by a nasogastric device.

Example 20A. The method of example 18A or example 19A, further comprising deploying an external electrode on an external skin surface of the patient.

Example 21A. The method of any of examples 18A-20A, further comprising expanding an expandable member to distend the esophagus of the patient.

Example 22A. The method of any of examples 18A-21A, further expanding an expandable member to position electrodes at a desired position within the esophagus.

Example 23A. The method of example 21A or example 22A, wherein the expandable member comprises a balloon.

Example 24A. The method of any of examples 18A-23A, further comprising delivering the stimulation signal to a target tissue within the patient via at least one electrode.

Example 25A. The method of example 24A, wherein the target tissue is at least one branch of a vagus nerve.

Example 26A. The method of any of examples 18A-25A, wherein the array of electrodes comprises between 2 and 16 electrodes, inclusively.

Example 27A. The method of any of examples 24A-26A, wherein the at least one electrode is disposed on an exterior surface of an expandable member.

Example 28A. The method of any of examples 24A-27A, wherein the at least one electrode comprises at least one of: a planar electrode; a non-planar electrode; an indenting electrode comprising at least one protrusion extending from a surface of the indenting electrode, the at least one protrusion being configured to indent a wall of the esophagus; or a puncturing electrode comprising at least one protrusion extending from a surface of the puncturing electrode, the at least one protrusion being configured to puncture the wall of the esophagus.

Example 29A. The method of any of examples 18A-28A, wherein the sensor signal is a first sensor signal and the method further comprises: receiving a second sensor signal indicative of one or more of a sensed heart rate, a sensed vagus nerve activity, or a sensed temperature; and changing, based on the second sensor signal, at least one stimulation parameter that defines the stimulation signal.

Example 30A. The method of example 29A, wherein the processing circuitry receives the second sensor signal from one of the sensor circuitry or a sensor external to the device.

Example 31A. The method of any of examples 18A-30A, further receiving, from a battery, power for a neurostimulation device.

Example 32A. The method of any of examples 18A-31A, further comprising: determining that at least one of an impedance is below a predetermined threshold or an expandable member has been expanded; and responsive to the determination, controlling, by the processing circuitry, the stimulation circuitry to begin generating the stimulation signal.

Example 33A. The method of any of examples 18A-32A, further comprising controlling, by the processing circuitry, the stimulation circuitry to generate a sub-sensory stimulation signal responsive to determining that the patient is conscious and generate a supra-sensory stimulation signal responsive to determining the patient is unconscious.

Example 34A. A non-transitory storage medium computer-readable storage medium encoded with instructions that, when executed, cause processing circuitry of a device to: control stimulation circuitry to generate the stimulation signal based at least in part on one or more stimulation parameters; and wherein at least one of: a) the device comprises a detachable neurostimulation device configured to be attached to a wall of an esophagus without a tether and to detach from the wall of the esophagus, b) the device comprises an array of radially divided electrodes configured to deliver the stimulation signal to a target location in a patient in a cycled manner, c) the instructions cause the processing circuitry to determine locations of an anterior branch of a vagus nerve or a posterior branch of a vagus nerve based on impedance sensed by at least one electrode, d) the device comprises sensor circuitry which comprises an accelerometer configured to sense a posture of the patient, wherein the instructions cause the processing circuitry to control the stimulation circuitry further based on the posture of the patient, e) the instructions cause the processing circuitry to receive a sensor signal indicative of one or more of a heart rate variability over time or respiration rate, f) the instructions cause the processing circuitry to control the stimulation circuitry to begin a stimulation sequence automatically, g) the device is configured to be inserted submucosally or between layers of longitudinal and circumferential muscles, h) the device further comprises a detachable controller, or i) the instructions cause the processing circuitry to control the stimulation circuitry to deliver stimulation at one location of the vagus nerve and at a different frequency to another location of the vagus nerve.

Example 1B. A system comprising: stimulation circuitry configured to generate a transesophageal stimulation signal; memory configured to store stimulation parameters that at least partially define the transesophageal stimulation signal; and processing circuitry communicatively coupled to the memory, and the stimulation circuitry, the processing circuitry being configured to: determine a maximum transesophageal stimulation amplitude value that is below a threshold amplitude value that defines a transesophageal stimulation amplitude that elicits muscular activity in response to delivery of the stimulation signal via a combination of electrodes; and control the stimulation circuitry to generate the transesophageal stimulation signal based at least in part on at least one of the stimulation parameters or the maximum transesophageal stimulation amplitude such that an amplitude of the transesophageal stimulation signal does not exceed the maximum transesophageal stimulation amplitude.

Example 2B. The system of example 1B, wherein the processing circuitry is further configured to, prior to controlling the stimulation circuitry to generate the transesophageal stimulation signal, determine the combination of electrodes, wherein as part of determining the combination of electrodes, the processing circuitry is configured to: determine a respective maximum transesophageal stimulation amplitude value that is below the threshold amplitude value for a plurality of different electrode combinations based on feedback, wherein the feedback comprises at least one of respective electromyogram signals, respective evoked compound action potentials (ECAPs), respective accelerometer signals, or respective patient reported sensations; and select, as the combination of electrodes, one of the plurality of different electrode combinations that has at least one of a highest ECAP or a highest respective maximum transesophageal stimulation amplitude value.

Example 3B. The system of example 2B, wherein the processing circuitry is further configured to repeat the determination of the combination of electrodes in response to determining a device has moved, at a predetermined time interval, or in response to user input.

Example 4B. The system of any combination of examples 1B-3B, wherein the processing circuitry is further configured to: determine a posterior direction; and control the stimulation circuitry to deliver the transesophageal stimulation signal in the posterior direction.

Example 5B. The system of example 4B, wherein the processing circuitry is configured to determine the posterior direction based at least one of on one or more accelerometer signals, an inclinometer signal, or a signal indicative of an electrocardiogram.

Example 6B. The system of any combination of examples 1B-5B, wherein the processing circuitry is further configured to: determine a physiological activity of a patient; and control the stimulation circuitry to gate the delivery of the transesophageal stimulation signal based on the physiological activity of the patient.

Example 7B. The system of example 6B, wherein the physiological activity comprises at least one of a phase of respiration, a heart rate, a phase of a cardiac cycle, or a phase of a circadian rhythm.

Example 8B. The system of any combination of examples 1B-7B, further comprising a stomach sensor configured to generate a signal indicative of the stomach sensor being in a stomach of a patient.

Example 9B. The system of example 8B, wherein the stomach sensor comprises at least one of a pressure sensor or a pH sensor.

Example 10B. The system of any combination of examples 1B-9B, wherein at least a portion of the system is configured to be inserted into an esophagus of the patient and wherein the at least the portion of the system comprises at least one of a lubricant or local anesthetic.

Example 11B. The system of any combination of examples 1B-10B, further comprising: an outer electrode actuator, the outer electrode actuator being configured to expand a membrane carrying one or more electrodes outward in response to manipulation.

Example 12B. A method comprising: generating, by stimulation circuitry, a transesophageal stimulation signal; determining, by processing circuitry, a maximum stimulation amplitude value that is below a threshold amplitude value that defines a transesophageal stimulation amplitude that elicits muscular activity in response to delivery of the stimulation signal via a combination of electrodes; and controlling, by the processing circuitry, the stimulation circuitry to generate the transesophageal stimulation signal based at least in part on at least one stimulation parameter or the maximum transesophageal stimulation amplitude prior to muscular activity such that an amplitude of the transesophageal stimulation signal does not exceed the maximum transesophageal stimulation amplitude.

Example 13B. The method of example 12B, further comprising: prior to controlling the stimulation circuitry to generate the transesophageal stimulation signal, determining the combination of electrodes, wherein determining the combination of electrodes comprises: determining a respective maximum transesophageal stimulation amplitude value that is below the threshold amplitude value for a plurality of different electrode combinations based on feedback, wherein the feedback comprises at least one of respective electromyogram signals, respective evoked compound action potentials (ECAPs), respective accelerometer signals, or respective patient reported sensations; and selecting, as the combination of electrodes, one of the plurality of different electrode combinations that has at least one of a highest ECAP or a highest respective maximum transesophageal stimulation amplitude value.

Example 14B. The method of example 13B, further comprising: repeating the determining of the combination of electrodes in response to determining a device has moved, at a predetermined time interval, or in response to user input.

Example 15B. The method of any combination of examples 12B-14B, further comprising: determining, by the processing circuitry, a posterior direction; and controlling, by the processing circuitry, the stimulation circuitry to deliver the transesophageal stimulation signal in the posterior direction.

Example 16B. The method of example 15B, wherein the determining the posterior direction is based on at least one of one or more accelerometer signals, an inclinometer signal, or a signal indicative of an electrocardiogram.

Example 17B. The method of any combination of examples 12B-16B, further comprising: determining, by the processing circuitry, a physiological activity of a patient; and controlling, by the processing circuitry, the stimulation circuitry to gate the delivery of the transesophageal stimulation signal based on the physiological activity of the patient.

Example 18B. The method of example 17B, wherein the physiological activity comprises at least one of a phase of respiration, a heart rate, a phase of a cardiac cycle, or a phase of a circadian rhythm.

Example 19B. The method of any combination of examples 12B-18B, further comprising: generating, by a stomach sensor, a signal indicative of the stomach sensor being in a stomach of a patient.

Example 20B. The method of example 19B, wherein the stomach sensor comprises at least one of a pressure sensor or a pH sensor.

Example 21B. The method of any combination of examples 12B-20B, further comprising inserting at least a portion of a device into an esophagus of a patient, wherein the at least a portion of the device comprises at least one of a lubricant or local anesthetic.

Example 22B. The method of any combination of examples 12B-21B, further comprising: expanding a membrane carrying one or more electrodes outward in response to manipulation of an outer electrode actuator.

Example 23B. A non-transitory storage medium computer-readable storage medium encoded with instructions that, when executed, cause processing circuitry of a device to: determine a maximum transesophageal stimulation amplitude value that is below a threshold amplitude value that defines a transesophageal stimulation amplitude that elicits muscular activity in response to delivery of a stimulation signal via a combination of electrodes, the transesophageal stimulation signal being at least partially defined by stimulation parameters; and control stimulation circuitry to generate the transesophageal stimulation signal based at least in part on at least one of the stimulation parameters or the maximum transesophageal stimulation amplitude such that an amplitude of the transesophageal stimulation signal does not exceed the maximum transesophageal stimulation amplitude.

Example 1C. A system comprising: stimulation circuitry configured to generate a transesophageal stimulation signal; memory configured to store stimulation parameters that at least partially define the transesophageal stimulation signal; and processing circuitry communicatively coupled to the memory, and the stimulation circuitry, the processing circuitry being configured to: determine a maximum transesophageal stimulation amplitude value that is below a threshold amplitude value; and control the stimulation circuitry to generate the transesophageal stimulation signal based at least in part on at least one of the stimulation parameters or the maximum transesophageal stimulation amplitude such that an amplitude of the transesophageal stimulation signal does not exceed the maximum transesophageal stimulation amplitude.

Example 2C. The system of example 1C, wherein the processing circuitry is further configured to determine the threshold amplitude value based on at least one of a transesophageal stimulation amplitude that elicits muscular activity in response to delivery of the stimulation signal via a combination of electrodes or patient input in response to delivery of the stimulation signal via the combination of electrodes.

Example 3C. The system of example 1C or example 2C, wherein the processing circuitry is further configured to, prior to controlling the stimulation circuitry to generate the transesophageal stimulation signal, determine a combination of electrodes, wherein as part of determining the combination of electrodes, the processing circuitry is configured to: determine a respective maximum transesophageal stimulation amplitude value that is below the threshold amplitude value for a plurality of different electrode combinations based on feedback, wherein the feedback comprises at least one of respective electromyogram signals, respective evoked compound action potentials (ECAPs), respective accelerometer signals, or respective patient reported sensations; and select, as the combination of electrodes, one of the plurality of different electrode combinations that has at least one of a highest ECAP or a highest respective maximum transesophageal stimulation amplitude value.

Example 4C. The system of example 3C, wherein the processing circuitry is further configured to repeat the determination of the combination of electrodes in response to determining a device has moved, at a predetermined time interval, or in response to user input.

Example 5C. The system of any combination of examples 1C-4C, wherein the processing circuitry is further configured to: determine a posterior direction; and control the stimulation circuitry to deliver the transesophageal stimulation signal in the posterior direction.

Example 6C. The system of example 5C, wherein the processing circuitry is configured to determine the posterior direction based at least one of on one or more accelerometer signals, an inclinometer signal, or a signal indicative of an electrocardiogram.

Example 7C. The system of any combination of examples 1C-6C, wherein the processing circuitry is further configured to: determine a physiological activity of a patient; and control the stimulation circuitry to gate the delivery of the transesophageal stimulation signal based on the physiological activity of the patient.

Example 8C. The system of example 7C, wherein the physiological activity comprises at least one of a phase of respiration, a heart rate, a phase of a cardiac cycle, or a phase of a circadian rhythm.

Example 9C. The system of any combination of examples 1C-8C, further comprising a stomach sensor configured to generate a signal indicative of the stomach sensor being in a stomach of a patient.

Example 10C. The system of example 9C, wherein the stomach sensor comprises at least one of a pressure sensor or a pH sensor.

Example 11C. The system of any combination of examples 1C-10C, wherein at least a portion of the system is configured to be inserted into an esophagus of the patient and wherein the at least the portion of the system comprises at least one of a lubricant or local anesthetic.

Example 12C. The system of any combination of examples 1C-11C, further comprising: an outer electrode actuator, the outer electrode actuator being configured to expand at least one of a membrane or a lead, the membrane or lead carrying one or more electrodes outward in response to manipulation.

Example 13C. The system of any combination of examples 1C-12C, further comprising a plurality of electrodes.

Example 14C. The system of example 13C, wherein the plurality of electrodes are arranged in a helix or spiral pattern on a lead around a longitudinal axis.

Example 15C. The system of example 14C, wherein the plurality of electrodes are cylindrical in shape and are configured such that a longitudinal axis of each of the plurality of electrodes is more than 20 degrees separated from a longitudinal axis of at least one of the lead or a longitudinal axis of an esophagus when in use.

Example 16C. The system of any combination of examples 13C-15C, wherein the plurality of electrodes are configured to contact an esophageal wall without penetrating mucosa or the esophageal wall.

Example 17C. The system of any combination of examples 1C-16C, wherein the transesophageal stimulation signal forms fields which are predominately aligned with a longitudinal axis of an esophagus.

Example 18C. The system of any of examples 1C-17C, wherein the system is configured such that a patient may swallow or a nasogastric tube may be inserted into the patient when the system is in use for the patient.

Example 19C. A method comprising: generating, by stimulation circuitry, a transesophageal stimulation signal; determining, by processing circuitry, a maximum stimulation amplitude value that is below a threshold amplitude value; and controlling, by the processing circuitry, the stimulation circuitry to generate the transesophageal stimulation signal based at least in part on at least one stimulation parameter or the maximum transesophageal stimulation amplitude prior to muscular activity such that an amplitude of the transesophageal stimulation signal does not exceed the maximum transesophageal stimulation amplitude.

Example 20C. A non-transitory storage medium computer-readable storage medium encoded with instructions that, when executed, cause processing circuitry of a device to: determine a maximum transesophageal stimulation amplitude value that is below a threshold amplitude value, the transesophageal stimulation signal being at least partially defined by stimulation parameters; and control stimulation circuitry to generate the transesophageal stimulation signal based at least in part on at least one of the stimulation parameters or the maximum transesophageal stimulation amplitude such that an amplitude of the transesophageal stimulation signal does not exceed the maximum transesophageal stimulation amplitude.

Example 21C. A transesophageal neurostimulation lead comprising: a distal portion, the distal portion being helix-shaped around a longitudinal axis; a plurality of electrodes, the plurality of electrodes being disposed on the distal portion and being configured to deliver transesophageal neurostimulation to a patient, wherein the distal portion forms an opening around the longitudinal axis such that the patient may swallow or a nasogastric tube may be introduced into an esophagus of the patient when the lead is at least partially within the esophagus of the patient.

Various examples have been described herein. Any combination of the described operations or functions is contemplated. These and other examples are within the scope of the following claims. Based upon the above discussion and illustrations, it is recognized that various modifications and changes may be made to the disclosed examples in a manner that does not require strictly adherence to the examples and applications illustrated and described herein. Such modifications do not depart from the true spirit and scope of various aspects of the disclosure, including aspects set forth in the claims.

What is claimed is:

1. A system comprising:

stimulation circuitry configured to generate a transesophageal stimulation signal;

memory configured to store stimulation parameters that at least partially define the transesophageal stimulation signal; and processing circuitry communicatively coupled to the memory, and the stimulation circuitry, the processing circuitry being configured to:

for each of a plurality of different electrode combinations of a plurality of electrodes, determine a corresponding threshold amplitude value based on a transesophageal stimulation amplitude that elicits muscular activity in response to delivery of the transesophageal stimulation signal via a corresponding combination of electrodes;

for each of the plurality of different electrode combinations, determine a corresponding maximum transesophageal stimulation amplitude value that is below the corresponding threshold amplitude value based on corresponding evoked compound action potentials (ECAPs);

select, as the combination of electrodes, one of the plurality of different electrode combinations that has at least one of a highest ECAP amplitude value or a highest respective maximum transesophageal stimulation amplitude value;

select the maximum transesophageal stimulation amplitude value associated with the combination of electrodes;

determine at least one of a phase of a cardiac cycle of a patient or a phase of a circadian rhythm of the patient;

control the stimulation circuitry to generate the transesophageal stimulation signal based at least in part on at least one of the stimulation parameters or the maximum transesophageal stimulation amplitude such that the transesophageal stimulation signal is delivered via the combination of electrodes and an amplitude of the transesophageal stimulation signal does not exceed the maximum transesophageal stimulation amplitude; and control the stimulation circuitry to gate the delivery of the transesophageal stimulation signal to be during the at least one of the phase of a cardiac cycle of the patient or the phase of a circadian rhythm of the patient.

2. The system of claim 1, wherein the processing circuitry is further configured to repeat the determination of the combination of electrodes in response to determining a device has moved, at a predetermined time interval, or in response to user input.

3. The system of claim 1, wherein the processing circuitry is further configured to:

determine a posterior direction; and control the stimulation circuitry to deliver the transesophageal stimulation signal in the posterior direction.

4. The system of claim 3, wherein the processing circuitry is configured to determine the posterior direction based on at least one of one or more accelerometer signals, an inclinometer signal, or a signal indicative of an electrocardiogram.

5. The system of claim 1, further comprising a stomach sensor configured to generate a signal indicative of the stomach sensor being in a stomach of the patient, wherein the processing circuitry is configured to control the stimulation circuitry to generate the transesophageal stimulation signal in response to the signal indicative of the stomach sensor being in the stomach of the patient.

6. The system of claim 5, wherein the stomach sensor comprises at least one of a pressure sensor or a pH sensor.

7. The system of claim 1, wherein at least a portion of the system is configured to be inserted into an esophagus of the patient and wherein the at least the portion of the system comprises at least one of a lubricant or local anesthetic configured to be disposed on an external surface of the at least the portion of the system during insertion of the at least the portion of the system into the esophagus.

8. The system of claim 1, further comprising an outer electrode actuator, the outer electrode actuator being configured to expand at least one of a membrane or a lead, the membrane or lead carrying one or more electrodes, outward in response to manipulation.

9. The system of claim 1, further comprising a plurality of electrodes.

10. The system of claim 9, wherein the plurality of electrodes are arranged in a helix or spiral pattern on a lead around a longitudinal axis.

11. The system of claim 10, wherein the plurality of electrodes are cylindrical in shape and are configured such that a longitudinal axis of each of the plurality of electrodes is more than 20 degrees separated from a longitudinal axis of at least one of the lead or a longitudinal axis of an esophagus when in use.

12. The system of claim 9, wherein the plurality of electrodes are configured to contact an esophageal wall without penetrating mucosa or the esophageal wall.

13. The system of claim 1, wherein the transesophageal stimulation signal forms fields which are predominately aligned with a longitudinal axis of an esophagus.

14. The system of claim 1, wherein the system is configured such that the patient may swallow or a nasogastric tube may be inserted into the patient when the system is in use for the patient.

15. A method comprising:

generating, by stimulation circuitry, a transesophageal stimulation signal, the transesophageal stimulation signal being at least partially defined by stimulation parameters;

determining, by processing circuitry and for each of a plurality of different electrode combinations of a plurality of electrodes, a corresponding threshold amplitude value based on at a transesophageal stimulation amplitude that elicits muscular activity in response to delivery of the transesophageal stimulation signal via a corresponding combination of electrodes;

determining, by the processing circuitry and for each of the plurality of different electrode combinations, a corresponding maximum transesophageal stimulation amplitude value that is below the corresponding threshold amplitude value based on corresponding evoked compound action potentials (ECAPs);

selecting, by the processing circuitry and as the combination of electrodes, one of the plurality of different electrode combinations that has at least one of a highest ECAP amplitude value or a highest respective maximum transesophageal stimulation amplitude value;

selecting, by the processing circuitry, the maximum stimulation amplitude value associated with the combination of electrodes;

determining, by the processing circuitry, at least one of a phase of a cardiac cycle of a patient or a phase of a circadian rhythm of the patient;

controlling, by the processing circuitry, the stimulation circuitry to generate the transesophageal stimulation signal based at least in part on at least one stimulation parameter or the maximum transesophageal stimulation amplitude such the transesophageal stimulation signal is delivered via the combination of electrodes and that an amplitude of the transesophageal stimulation signal does not exceed the maximum transesophageal stimulation amplitude; and controlling, by the processing circuitry, the stimulation circuitry to gate the delivery of the transesophageal stimulation signal to be during the at least one of the phase of a cardiac cycle of the patient or the phase of a circadian rhythm of the patient.

16. A system comprising:

stimulation circuitry configured to generate a transesophageal stimulation signal;

memory configured to store stimulation parameters that at least partially define the transesophageal stimulation signal; and processing circuitry communicatively coupled to the memory, and the stimulation circuitry, the processing circuitry being configured to:

determine a maximum transesophageal stimulation amplitude value that is below a threshold amplitude value;

determine a respective maximum transesophageal stimulation amplitude value that is below the threshold amplitude value for each of a plurality of different electrode combinations based on respective evoked compound action potentials (ECAPs);

select, as a combination of electrodes for delivery of the transesophageal stimulation signal, one of the plurality of different electrode combinations that has at least one of a highest ECAP amplitude value or a highest respective maximum transesophageal stimulation amplitude value; and control the stimulation circuitry to generate the transesophageal stimulation signal based at least in part on at least one of the stimulation parameters or the maximum transesophageal stimulation amplitude such that an amplitude of the transesophageal stimulation signal does not exceed the maximum transesophageal stimulation amplitude and deliver the transesophageal stimulation signal via the selected one of the plurality of different electrode combination.

* * * * *